United States Patent
Jin et al.

(10) Patent No.: US 12,065,666 B2
(45) Date of Patent: Aug. 20, 2024

(54) TARGETED GENE EDITING PLATFORM INDEPENDENT OF DNA DOUBLE STRAND BREAK AND USES THEREOF

(71) Applicant: Rutgers, the State University, New Brunswick, NJ (US)

(72) Inventors: Shengkan Jin, Belle Mead, NJ (US); Juan-Carlos Collantes, Princeton, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 769 days.

(21) Appl. No.: 16/475,412

(22) PCT Filed: Jan. 4, 2018

(86) PCT No.: PCT/US2018/012304
§ 371 (c)(1),
(2) Date: Jul. 2, 2019

(87) PCT Pub. No.: WO2018/129129
PCT Pub. Date: Jul. 12, 2018

(65) Prior Publication Data
US 2019/0330658 A1 Oct. 31, 2019

Related U.S. Application Data

(60) Provisional application No. 62/442,704, filed on Jan. 5, 2017.

(51) Int. Cl.
| | | |
|---|---|---|
| *A61K 31/7088* | (2006.01) | |
| *A61K 38/46* | (2006.01) | |
| *A61K 38/50* | (2006.01) | |
| *A61K 48/00* | (2006.01) | |
| *C12N 9/22* | (2006.01) | |
| *C12N 9/78* | (2006.01) | |
| *C12N 15/113* | (2010.01) | |
| *C12N 15/62* | (2006.01) | |
| *C12N 15/90* | (2006.01) | |

(52) U.S. Cl.
CPC .......... *C12N 15/90* (2013.01); *A61K 31/7088* (2013.01); *A61K 38/465* (2013.01); *A61K 38/50* (2013.01); *A61K 48/00* (2013.01); *C12N 9/22* (2013.01); *C12N 9/78* (2013.01); *C12N 15/113* (2013.01); *C12N 15/62* (2013.01); *C07K 2319/00* (2013.01); *C12N 2310/20* (2017.05); *C12N 2310/3519* (2013.01); *C12N 2800/80* (2013.01)

(58) Field of Classification Search
None
See application file for complete search history.

(56) References Cited

U.S. PATENT DOCUMENTS

| | | | |
|---|---|---|---|
| 8,697,359 B1 | 4/2014 | Zhang | |
| 10,550,372 B2 | 2/2020 | Konermann et al. | |
| 2011/0104787 A1 | 5/2011 | Church et al. | |
| 2014/0273226 A1 | 9/2014 | Wu | |
| 2014/0295556 A1 | 10/2014 | Joung et al. | |
| 2016/0177278 A1* | 6/2016 | Wolfe | C12N 9/22 435/199 |
| 2017/0073670 A1 | 3/2017 | Nishida et al. | |
| 2017/0121693 A1 | 5/2017 | Liu et al. | |
| 2017/0233762 A1 | 8/2017 | Zalatan et al. | |
| 2017/0240922 A1 | 8/2017 | Gill et al. | |
| 2020/0165587 A1 | 5/2020 | Tsai et al. | |

FOREIGN PATENT DOCUMENTS

| | | |
|---|---|---|
| EP | 3115457 A1 | 1/2017 |
| JP | 2016506541 A | 3/2016 |
| WO | 2014/144288 A1 | 9/2014 |
| WO | 2014144592 A2 | 9/2014 |
| WO | WO-2014/144288 A1 | 9/2014 |
| WO | 2014/204725 A1 | 12/2014 |
| WO | WO-2014/204725 A1 | 12/2014 |
| WO | 2015089406 A1 | 6/2015 |
| WO | WO-2015/089406 A1 | 6/2015 |
| WO | 2015133554 A1 | 9/2015 |
| WO | 2016/054106 A1 | 4/2016 |
| WO | WO-2016/054106 A1 | 4/2016 |
| WO | 2016/081923 A2 | 5/2016 |
| WO | WO-2016/081923 A2 | 5/2016 |
| WO | 2017011721 A1 | 1/2017 |
| WO | 2018129129 A1 | 7/2018 |
| WO | 2018/218166 A1 | 11/2018 |

OTHER PUBLICATIONS

Zalatan et al., Engineering Complex Synthetic Transcriptional Programs with CRISPR RNA Scaffolds Cell (2015) 160, 339-350 (Year: 2015).*

Mali et al., Cas9 as a versatile tool for engineering biology. Nature Methods (2013) 10:10, 957-963 (Year: 2013).*

Hess et al., Directed evolution using dCas9-targeted somatic hypermutation in mammalian cells. Nature Methods (2016), 13(12): 1036-1042 and Supplemental Material (Year: 2016).*

Plasmid #85416, pGH153_MS2-AIDΔ-Hygro. Retrieved from internet. https://www.addgene.org/85416/ [retrieved on Apr. 14, 2022] (Year: 2022).*

K-562. Retrieved from internet. https://www.atcc.org/products/ccl-243, [retrieved on Apr. 14, 2022] (Year: 2022).*

Komor et al., (2016) Programmable editing of a target base in genomic DNA without double-stranded DNA cleavage. Nature 533: 420-424 (Year: 2016).*

(Continued)

*Primary Examiner* — Celine X Qian
*Assistant Examiner* — Catherine Konopka
(74) *Attorney, Agent, or Firm* — FOX ROTHSCHILD LLP

(57) ABSTRACT

The present invention discloses systems for targeted gene editing and related uses.

20 Claims, 17 Drawing Sheets

Specification includes a Sequence Listing.

(56) References Cited

OTHER PUBLICATIONS

Zhu et al., The CRISPR/Cas9 system inactivates latent HIV-1 proviral DNA. Retrovirology (2015) 12(22): 1-7 (Year: 2015).*
Plasmid #85410, pGH220_wtGFP. https://www.addgene.org/85410 [retrieved on Aug. 24, 2022] (Year: 2022).*
Hess et al., Directed evolution using dCas9-targeted somatic hypermutation in mammalian cells. Nature Methods (2016), 13(12): 1036-1042 with additional Supplemental Material (Year: 2016).*
Peng et al., Potential pitfalls of CRISPR/Cas9-mediated genome editing. FEBS Journal (2016), 283: 1218-1231 (Year: 2016).*
Dahlman et al., Orthogonal gene knockout and activation with a catalytically active Cas9 nuclease. Nature Biotechnology (2015), 33:1159-1161 (Year: 2015).*
Kueh, et al: "The new editor-targeted genome engineering in the absence of homology-directed repair", Cell Death Discovery, Jun. 13, 2016, vol. 2. No. 1, pp. 1-2, XP055593859.
Makarova, et al: "Evolution and Classification of the CRISPR-Cas Systems", Nat Rev Microbiol., Jun. 2011, 9(6) 467-477. doi:10.1038/nrmicro2577.
Koonin, et al: "Diversity, classification and evolution of CRISPR-Cas Systems", Current Opinion in Microbiology, Jun. 2017, vol. 37, pp. 67-78.
Komor et al. "Programmable editing of a target base in genomic DNA without double-stranded DNA cleavage," Nature, Apr. 20, 2016 (20) vol. 533, No. 7603, pp. 420-424.
Zalatan, et al: "Engineering Complex Synthetic Transcriptional Programs with CRISPR RNA Scaffolds", Cell, Jan. 15, 2015, Cell, pp. 339-350.
Zalatan et al., "Engineering Complex Synthetic Transcriptional Programs with CRISPR RNA Scaffolds," Cell (Jan. 15, 2015); 160:339-350.
Maeder et al., "CRISPR RNA-guided activation of endogenous human genes," Nat Methods (2013); 10(10):977-979 (pp. 1-9).
Pefanis et al., "Noncoding RNA transcription targets AID to divergently transbribed loci in B cells," Nature (2014); 514(7522):389-393 (pp. 1-33).
Beerli, et al: "Toward Controlling Gene Expression at Will: Specific Regulation of the erbB-2/HER-2 Promoter by Using Polydactyl Zinc Finger Proteins Constructed from Modular Building Blocks", Proc. Natl. Acad. Sci., Dec. 1998, vol. 95, pp. 14628-14633.
Hiral et al: "Structure and Functions of Powerful Transactivators: VP16, MyoD and FoxA", Int. J. Dev. Biol., 2010, vol. 54, pp. 1589-1596.
Prochnow, et al: "The APOBEC-2 Crystal Structure and Functional Implications for the Deaminase AID", Nature, Jan. 25, 2007, vol. 445, pp. 447-451.
Komor, et al: "Programmable Editing of a Target Base in Genomic DNA Without Double-Stranded DNA Cleavage", Nature, 2016, 533(7603): 420-424, pp. 1-25.
Qi, et al: "Repurposing CRISPR as an RNA-Guided Platform for Sequence-Specific Control of Gene Expression", Cell, Feb. 28, 2013, vol. 152(5): 1173-1183, pp. 1-22.
Zetsche, BERND: Experimental Report, European Patent No. EP3322804, Rutgers, The State University of New Jersey, Beam Therapeutics Inc., pp. 1-16.
Zhu, et al: "The CRISPR/Cas9 inactivates latent HIV-1 proviral DNA", Retrovirology, 2015, 12(22): 1-7.
Abudayyeh, et al: "C2c2 is a single-component programmable RNA-guided RNA-targeting CRISPR effector", Science, Aug. 5, 2016, vol. 353, Issue 6299, pp. aaf5573-1-aaf5573-9.
ADDGENE: pCMV-BE3: Retrieved from internet: <URL: https://www.addgene.org/7301/> [retrieved on May 16, 2022].
Barker Brettell: Response to Written Opinion for European Patent Application No. 16825229.4 filed Jul. 2, 2019.
Barker Brettell: Response to Examination Report for European Patent Application No. 16825229.4 filed on May 11, 2020.
Chaudhuri et al: "Transcription-targeted DNA deamination by the AID antibody diversification enzyme", Nature, vol. 422, Apr. 17, 2003, pp. 726-730.

Collantes, et al: "Development and Characterization of a Modular CRISPR and RNA Aptamer Mediated Base Editing System", The CRISPR Journal, vol. 4, No. 1, 2021, pp. 58-68.
Collantes, et al: "Supplementary Sequences—Development and Characterization of a Modular CRISPR-RNA Aptamer-Mediated Base Editing System", pp. 35-43.
Cong, et al: "Multiplex Genome Engineering Using CRISPR/Cas Systems", Science, vol. 339, Feb. 15, 2013, pp. 819-823.
Conticello, Silvetro G.: "The AID/APOBEC family of nucleic acid mutators", Genome Biology, 2008, 9:229 (doi: 10.1186/gb-2008-9-6-229).
Cyranoski et al: "Chinese scientists genetically modify human embryos", Nature—News, Apr. 22, 2015 [retrieved from internet: <https://www.nature.com/news/chinese-scientists-genetically-modify-human-embryos-1.17378>.
Cryanoski et al: "International outcry over genome-edited baby claim", Nature, Nov. 29, 2018, vol. 563, pp. 607-608.
Cyranoski, David: "What's Next for CRISPR Babies?", Nature, Feb. 28, 2019, vol. 566, pp. 440-442.
Collantes Vela, Juan Carlos: "Dissertation—A Novel CRISPR/RNA-Aptamer-Medited Base Editing System with Potential Therapeutic Value", Rutgers, The State University of New Jersey, New Brunswick, NJ, Jan. 2019.
Doudna, et al: "The new frontier of genome engineering with CRISPR-Cas9", Science, Nov. 28, 2014, vol. 346, Issue 6213, pp. 1258096-1-1258096-9.
Gilbert et al: "CRISPR-Mediated Modular RNA-Guided Regulation of Transcription in Eukaryotes", Cell, Jul. 18, 2013, 154, pp. 442-451.
Gilbertson, Larry: "Cre-lox recombination: Cre-ative tools for plant biotechnology", Trends in Biotechnology, Dec. 2003, vol. 21, No. 12, pp. 550-555.
Heckl et al: "Toward Whole-Transcriptome Editing with CRISPR-Cas9", Molecular Cell, May 21, 2015, 58, pp. 560-562.
Hilton et al: "Epigenome editing by a CRISPR-Cas 9-based acetyltransferase activates genes from promoters and enhancers", Nature Biotechnology, May 2015, vol. 33, No. 5, pp. 510-517.
Hsu et al: "Development and Applications of CRISPR-Cas9 for Genome Engineering", Cell, Jun. 5, 2014, 157, pp. 1262-1278.
Hsu et al: "DNA targeting specificity of RNA-guided Cas9 nucleases", Nature Biotechnology, Sep. 2013, vol. 31, No. 9, pp. 827-832.
Jackson et al: "Conformational regulation of CRISPR-associated nucleases", Current Opinion in Microbiology, 2017, 37, pp. 110-119.
Jinek et al: A Programmable Dual-RNA-Guided DNA Endonuclease in Adaptive Bacterial Immunity, Science, Aug. 17, 2012, vol. 337, pp. 816-821.
Kearns et al: "Functional annotation of native enhancers with a Cas9-histone demethylase fusion", Nat Methods, May 2015, 12(5): pp. 1-13, doi:10.1038/nmeth.3325.
Konermann et al: "Genome-scale transcriptional activation by an engineered CRISPR-Cas9 complex", Nature, Jan. 29, 2015, vol. 517, pp. 583-588.
Koonin et al: "Diversity, classification and evolution of CRISPR-Cas systems", Current Opinion in Microbiology, 2017, 37, pp. 67-78.
Larson et al: "CRISPR interference (CRISPRi) for sequence-specific control of gene expression", Nat. Protoc., Nov. 2013, 8(11): pp. 2180-2196, doi:10.1038/nprot.2013.132.
Maeder et al: "Targeted DNA demethylation and activation of endogenous genes using programmable TALE-TET1 fusion proteins", Nature Biotechnology, Dec. 2013, vol. 31, No. 22, pp. 1137-1142.
Makarova et al: "Annotation and Classification of CRISPR-Cas Systems", Methods Mol Biol. 2015, 1311, pp. 47-75, doi:10.1007/978-1-4939-2687-9_4.
Mali et al: "CAS9 transcriptional activators for target specificity screening and paired nickases for cooperative genome engineering", Nature Biotechnology, 2013, 31, pp. 833-838.
Mali et al: "RNA-Guided Human Genome Engineering iva Cas9 and Supplementary Materials", Science, Feb. 15, 2013, vol. 339, pp. 823-826.

(56) References Cited

OTHER PUBLICATIONS

Perez-Pinera et al: "RNA-guided gene activation by CRISPR-Cas9-based transcription factors and Supplementary Information", Nature Methods, Oct. 2013, vol. 10, No. 10, pp. 973-976.
Shechner et al: "Multiplexable, locus-specific targeting of long RNAs with CRISPR-Display", Nature Methods, Jul. 2015, vol. 12, No. 7, pp. 664-670.
Stafforst et al: "An RNA-Deaminase Conjugate Selectively Repairs Point Mutations", Angew. Chem. Int. Ed, 2012, 51, pp. 11166-11169.
U.S. Appl. No. 62/192,876 entitled "Nuclease-Independent Targeted Gene Editing Platform and Uses Thereof", filed Jul. 15, 2015.
Yang et al: "Virion protein 16 induces demethylation of DNA integrated within chromatin in a novel mammalian cell model", Acta Biochim Biophys Sin, 2012, vol. 44, Issue 2, pp. 154-161.
Ying et al: "The kruppel-associated box repressor domain induces reversible and irreversible regulation of endogenous mouse genes by mediating different chromatin states", Nucleic Acids Research, 2015, vol. 43, No. 3, pp. 1549-1561, doi: 10.1093/narlgkv016.
Yu et al: "DNA Substrate Length and Surrounding Sequence Affect the Activation-induced Deaminase Activity at Cytidine", The Journal of Biological Chemistry, Feb. 20, 2004, vol. 279, No. 8, pp. 6496-6500.
Wenbing Yao., "Introduction to Biotechnology and Pharmacy", China Medical Science Press, Aug. 31, 2015, p. 253.
Li et al: "Base editing with a Cpf1-cytidine deaminase fusion", Nature Biotechnology, vol. 36, No. 4, Mar. 19, 2018, pp. 324-327, XP055579743, New York, ISSN: 1087-0156, DOI: 10.1038/nbt.4102.
Wang et al: "Enhanced base editing by co-expression of free uracil DNA glycosylase inhibitor", Cell Research, Aug. 29, 2017, vol. 27, No. 10, pp. 1289-1292, XP055579748.

\* cited by examiner

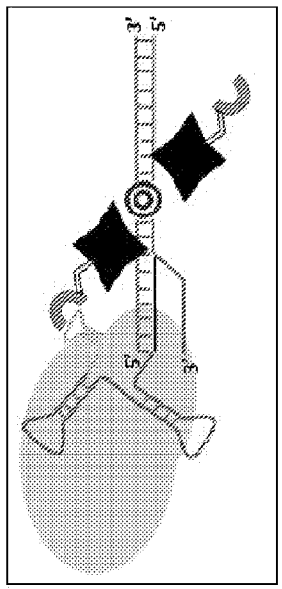
FIG. 1D
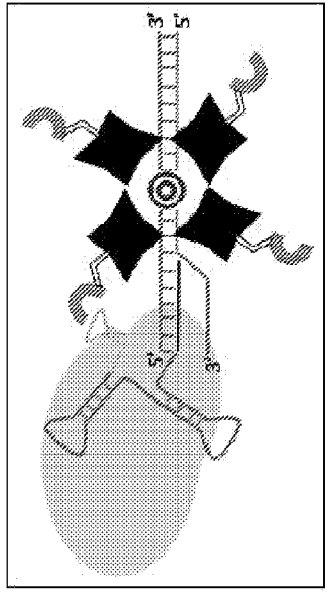
FIG. 1E
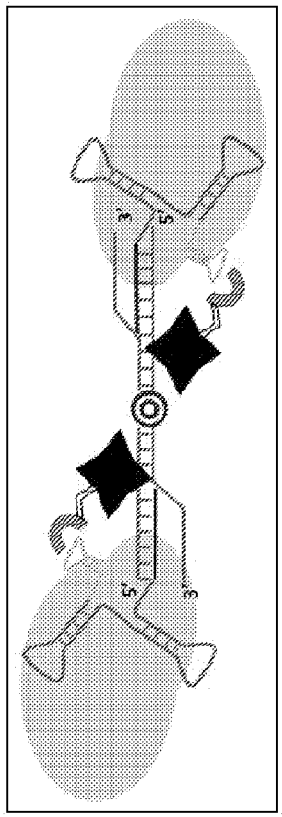
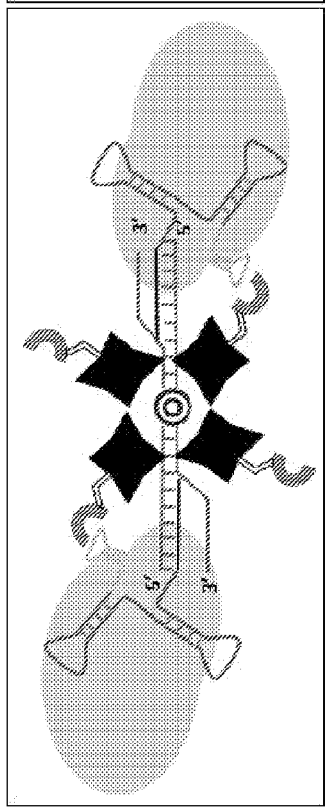
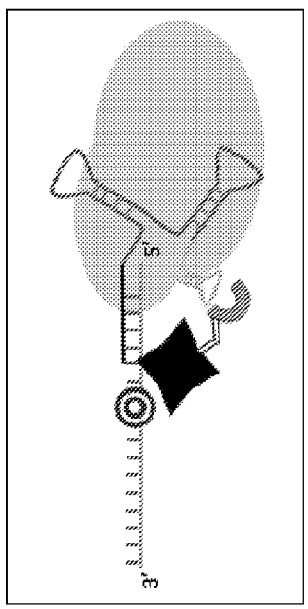
FIG. 1F

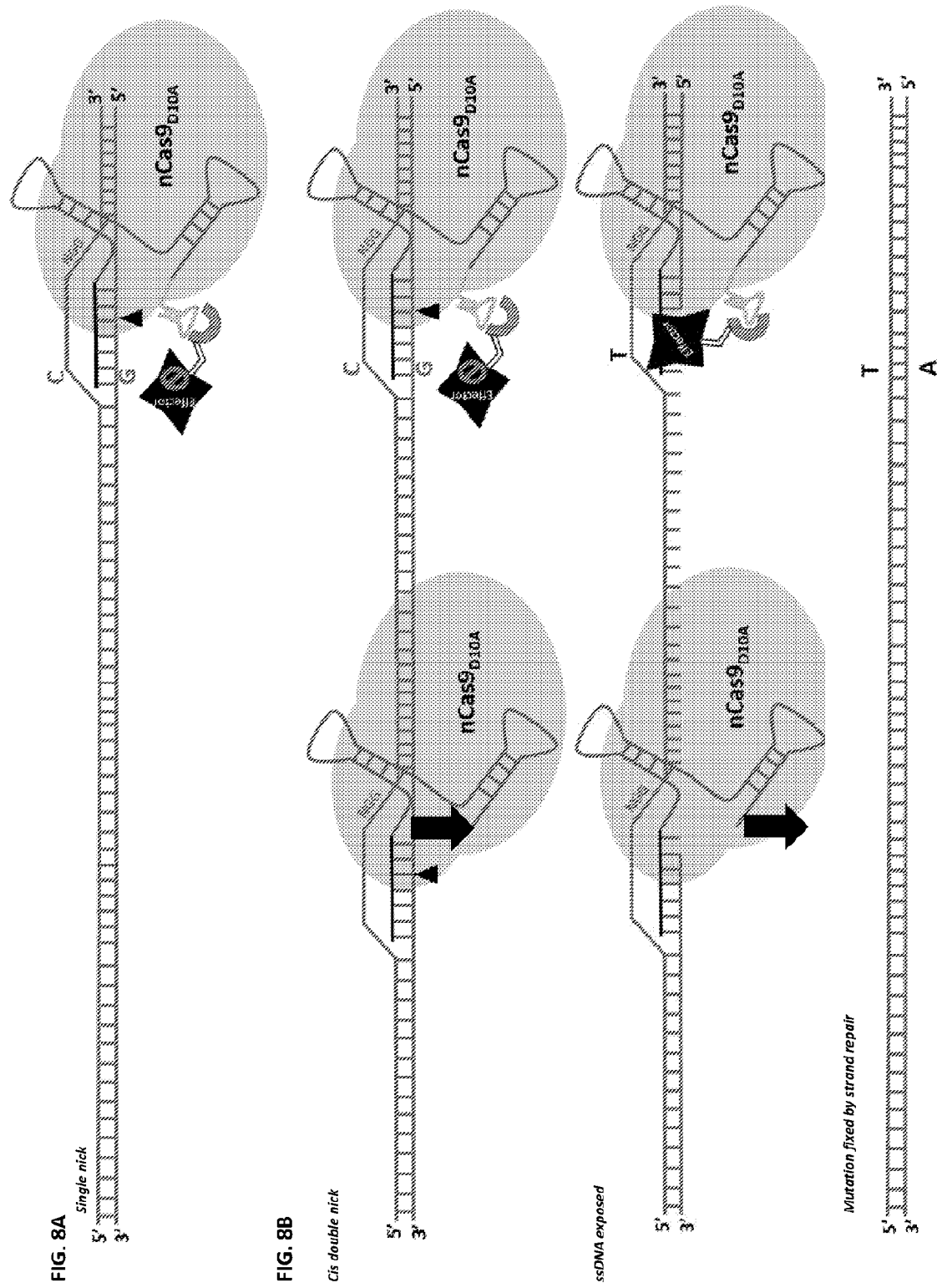

TARGETED GENE EDITING PLATFORM INDEPENDENT OF DNA DOUBLE STRAND BREAK AND USES THEREOF

CROSS REFERENCE TO RELATED APPLICATION

This application claims priority to U.S. Provisional Application No. 62/442,704 filed on Jan. 5, 2017. The content of the application is incorporated herein by reference in its entirety.

GOVERNMENT INTERESTS

The invention disclosed herein was made, at least in part, with Government support under Grant No. 15130816 from the Fulbright Foreign Student Program, Department of State. Accordingly, the U.S. Government has certain rights in this invention.

FIELD OF THE INVENTION

This invention relates to a system for targeted gene editing and related uses.

BACKGROUND OF THE INVENTION

Targeted gene editing is a powerful tool for genetic manipulation of eukaryotic cells, embryos, and animals. With that targeted genomic locations and/or specific chromosomal sequences can be deleted, inactivated, or modified. Several current methods rely on the use of engineered nuclease enzymes, such as zinc finger nucleases (ZFNs) or transcription activator-like effector nucleases (TALENs). These chimeric nucleases contain programmable, sequence-specific DNA-binding modules linked to a nonspecific DNA cleavage domain. Since each new genomic target requires the design of a new ZFN or TALEN comprising a novel sequence-specific DNA-binding module, these custom designed nucleases tend to be costly and time-consuming to prepare. Moreover, the specificities of ZFNs and TALENS are such that they can mediate off-target cleavages. A recently developed genome modification technology utilizes the bacterial clusters of regularly interspaced short palindromic repeats (CRISPR) associated protein 9 (Cas9), an RNA-guided DNA endonuclease, to induce a specific double-stranded break (DSB) at DNA target sites. The RNA-Cas9 complex identifies and base pairs with its cognate DNA target sequence, resulting in target cleavage to form a DSB.

However, one major problem unsolved is how to correct genetic mutations in somatic cells. Currently the common effectors for the existing technologies are nucleases, which lead to DNA DSB, which in turn triggers activation of cellular pathways such as homologous recombination and non-homologous end joining. The process has a number of major disadvantages. First, due to the unpredictable nature of the end-products by end joining, DSB leads to both in-frame and frame-shift mutations in a stochastic and unpredictable manner, which limits its use for direct clinical application. Second, DSBs have the potential of causing non-local mutagenic events, such as chromosome translocation, which is an undesirable outcome of the procedure. In vivo, these changes could be potentially deleterious. Third, the repair or correction usually requires DSB-mediated homologous recombination, the activity of which is low or even absent in most somatic tissues/cells, where therapeutics matter the most.

Thus, the current DSB nuclease-based technologies have limited applicability for gene editing and there is a need for a targeted gene modification technology that does not rely on nuclease activity that causes double-strand break.

SUMMARY OF INVENTION

This invention addresses the above-mentioned need by providing a targeted gene editing system and related uses.

In one aspect, the invention provides a method of site-specific modification of a target nucleic acid or polynucleotide, e.g., DNA or RNA. The method includes directing a gene editing machinery to the target nucleic acid. The gene editing machinery comprises a first system and a second system recognizing two different specific nucleic acid sequences of the target nucleic acid or polynucleotide, e.g., DNA or RNA. (See, e.g., illustration in FIG. 1A)

The first system comprises (i) a first sequence-targeting, single-strand DNA (ssDNA) nicking protein (STP), (ii) a first RNA scaffold comprising: (a) a first nucleic acid-targeting motif comprising a first guide RNA sequence that is complementary to a first target nucleic acid sequence in the target DNA, (b) a first CRISPR motif capable of binding to the first sequence-targeting protein, and (c) a first recruiting RNA motif, and (iii) a first non-nuclease effector fusion protein, comprising: (a) a first RNA binding domain capable of binding to the first recruiting RNA motif, (b) a first linker, and (c) a first effector domain. The first non-nuclease effector fusion protein has an enzymatic activity.

The second system recognizes a second specific nucleic sequence in the target DNA. The first target nucleic acid sequence and the second target nucleic acid sequence are on the same strand of the target DNA. Either one of the two target nucleic acid sequences can be upstream or downstream of the other so that the first and second systems recognize two specific sequences (e.g., guided by gRNA) surrounding a target nucleotide (e.g., one gRNA upstream the target site, one downstream the target site), introducing two nicks close to each other in cis i.e. on the same DNA strand. In this way, a stretch of ssDNA will be transiently exposed, allowing an effector module (e.g., a CRC effector module described below) to catalyze the nucleotide conversion, followed by fixation of the introduced modification upon strand repair (See, e.g., FIG. 8B and FIGS. 10A-D).

The second system can have various set of components but in general have (i) a second sequence-targeting, ssDNA nicking protein for targeting a second target nucleic acid sequence in the target DNA. This sequence-targeting, ssDNA nicking protein can be the same as the one in the first system.

In one embodiment, the second system further comprises (ii) a second RNA scaffold comprising: (a) a second nucleic acid-targeting motif comprising a second guide RNA sequence that is complementary to a second target nucleic acid sequence in the target DNA, (b) a second CRISPR motif capable of binding to the second sequence-targeting protein, and (c) a second recruiting RNA motif, and (iii) a second non-nuclease effector fusion protein, comprising: (a) a second RNA binding domain capable of binding to the second recruiting RNA motif, (b) a second linker, and (c) a second effector domain. The second recruiting RNA motif in (ii) and all components in (iii) can be the same as, or can be different from the components the first system. The second effector fusion protein may or may not have enzymatic activity.

In another embodiment, the second system can further comprise (ii) a second RNA scaffold comprising (a) a second nucleic acid-targeting motif comprising a second guide RNA sequence that is complementary to a second target nucleic acid sequence in the target DNA and (b) a second CRISPR motif capable of binding to the second sequence-targeting protein. Preferably, the second RNA scaffold does not have a recruiting RNA motif so that no effector protein is recruited to the second target nucleic acid sequence.

In yet another embodiment, the second system can further comprise (ii) a second RNA scaffold comprising: (a) a second nucleic acid-targeting motif comprising a second guide RNA sequence that is complementary to a second target nucleic acid sequence in the target DNA, (b) a second CRISPR motif capable of binding to the second sequence-targeting protein, and (c) a second recruiting RNA motif, and (iii) a local DNA repair inhibitor fusion protein, comprising: (a) a second RNA binding domain capable of binding to the second recruiting RNA motif, (b) a second linker, and (c) a local DNA repair inhibitor domain.

In the method described above, the first or second sequence-targeting protein can be a CRISPR protein. Preferably, the first or second sequence-targeting protein does not have a nuclease activity creating a double strand break. Examples of the first or second sequence-targeting protein include the sequence of dCas9 or nCas9 (nickase Cas9) of a species selected from the group consisting of *Streptococcus pyogenes, Streptococcus agalactiae, Staphylococcus aureus, Streptococcus thermophilus, Streptococcus thermophilus, Neisseria meningitidis*, and *Treponema denticola*. In some embodiments, the first sequence-targeting protein and the second sequence-targeting protein can be orthologs and associated with different PAMs.

In the method described above, (i) the first recruiting RNA motif and the first RNA binding domain or (ii) the second recruiting RNA motif and the second RNA binding domain can be a pair selected from the group consisting of a telomerase Ku binding motif and Ku protein or a RNA-binding section thereof, a telomerase Sm7 binding motif and Sm7 protein or a RNA-binding section thereof, a MS2 phage operator stem-loop and MS2 coat protein (MCP) or a RNA-binding section thereof, a PP7 phage operator stem-loop and PP7 coat protein (PCP) or a RNA-binding section thereof, a SfMu phage Com stem-loop and Com RNA binding protein or a RNA-binding section thereof, and a non-natural RNA aptamer and corresponding aptamer ligand or a RNA-binding section thereof.

In the above mentioned non-nuclease effector fusion protein, the linker sequence can be 0 to 100 (e.g., 1-100, 5-80, 10-50, and 20-30) amino acid residues in length. The enzymatic activity can be deamination activity, methyltransferase activity, demethylase activity, DNA repair activity, DNA damage activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity. In some embodiments, the enzymatic activity is deamination activity (e.g., a cytidine deamination activity or adenosine deamination activity), methyltransferase activity, or demethylase activity. The first or second RNA binding domain is not Cas9 nor its functional equivalent nor its RNA-binding domain. The second effector fusion protein may or may not have any enzymatic activity but can improve the desired editing property mediated by the first effector fusion protein.

The target nucleic acid can be in a cell. The target nucleic acid can be RNA, an extrachromosomal DNA, or a genomic DNA on a chromosome. The cell can be selected from the group consisting of: an archaeal cell, a bacterial cell, a eukaryotic cell, a eukaryotic single-cell organism, a somatic cell, a germ cell, a stem cell, a plant cell, an algal cell, an animal cell, in invertebrate cell, a vertebrate cell, a fish cell, a frog cell, a bird cell, a mammalian cell, a pig cell, a cow cell, a goat cell, a sheep cell, a rodent cell, a rat cell, a mouse cell, a non-human primate cell, and a human cell.

The cell can be in or derived from a human or non-human subject. The human or non-human subject has a genetic mutation or polymorphism of a gene. In some embodiments, the subject has a disorder caused by the genetic mutation or is at risk of having the disorder. In that case, the site-specific modification corrects the genetic mutation or inactivates the expression of the gene. In other embodiments, the subject has a pathogen or is at risk of exposing to the pathogen, and the site-specific modification inactivates a gene of the pathogen.

Also provided are an isolated nucleic acid encoding one or more of components (i)-(iii) of the first or second system described above, an expression vector comprising the nucleic acid, or a host cell comprising the nucleic acid.

Another aspect of the invention provides a composition comprising one or more selected from the group consisting of the first system described above, the second system described above, the isolated nucleic acid described above, the expression vector described above, and the host cell described above. Also provided is a kit comprising one or more selected from the group consisting of the first system described above, the second system described above, the isolated nucleic acid described above, the expression vector described above, and the host cell described above. The kit can further contain one or more components selected from the group consisting of a reagent for reconstitution and/or dilution and a reagent for introducing nucleic acid or polypeptide into a host cell.

The details of one or more embodiments of the invention are set forth in the description below. Other features, objectives, and advantages of the invention will be apparent from the description and from the claims.

BRIEF DESCRIPTION OF THE DRAWINGS

FIGS. 1B, 1C, 1D, 1E, and 1F are a set of schematic illustrations of an exemplary nuclease-independent CasR-cure or CRC platform for in vivo targeted genetic editing. FIG. 1B. Components of the platform, from left to right: (1) a sequence targeting component dCas9, (2) a RNA scaffold containing a guide RNA motif (for sequence targeting), a CRISPR motif (for dCas9 binding), and a recruiting RNA motif (for recruiting effector-RNA binding protein fusion), and (3) an effector-RNA binding domain fusion protein. The system can be programmed to target specific nucleotides on DNA or RNA molecules (right). FIG. 1C. If the effector protein functions as a monomer, the system can be targeted to a single site, upstream (left) or downstream (right) of the target site. FIG. 1D. If the effector protein requires dimerization for proper catalytic function, the system can be multiplexed to target sequences upstream and downstream of the target site simultaneously, therefore allowing the effector proteins to dimerize (right). Alternatively, recruitment of effector protein to a single site may be sufficient to increase its affinity for neighboring effector proteins, promoting dimerization (right). FIG. 1E. Examples of a tetramer effector enzyme recruited and positioned at the target site, which can be achieved by dual (left) or single targeting (right). FIG. 1F. A system that can be used to edit RNA targets (e.g. retrovirus inactivation).

FIG. 2A. Schematic of target region along RRDR Cluster I of *E. coli*'s rpoB gene (SEQ ID Nos: 23 and 24). Shown are (top) DNA sequence (SEQ ID No: 23), with PAMs (boxed) and mutable positions (arrows) shown; (middle) binding sites of gRNAs used in these experiments, all gRNAs were programmed to target the template strand (TS, −); (bottom) protein sequence (SEQ ID No: 25) with critical amino acids involved in rifampicin resistance shown (arrows). FIG. 2B. *E. coli* MG1655 cells were treated with $^{AID}$CRC and the indicated gRNAs and selected in plates containing 120 µM rifampicin. FIG. 2C. Mutation frequency calculated from B top panel. FIG. 2D. Representative sequencing results from $^{AID}$CRC treatment with rpoB_TS-4 gRNA (top, SEQ ID No: 26) and untreated cells (middle, SEQ ID No: 27). C1592>T mutation results in S531F change in protein sequence (bottom, SEQ ID Nos: 28 and 29), a mutation known to induce Rif (Petersen-Mahrt, et al., *Nature* 418, 99-104 (2002), Xu, M., et al., *Journal of Bacteriology* 187, 2783-2792, doi:10.1128/JB.187.8.2783-2792.2005 (2005), and Zenkin, N., et al., *Antimicrobial Agents and Chemotherapy* 49, 1587-1590, doi:10.1128/AAC.49.4.1587-1590.2005 (2005)). The modified nucleotides and amino acid residues are shown in C and S (wild type) and T and F (mutant). FIG. 2E. Mutation distribution of treatments $^{AID}$CRC with gRNAs rpoB_TS-3, rpoB_TS-4 and scramble (SEQ ID Nos: 30-41). FIG. 2F. Data suggest that CRC actively deaminates target cytidine residues located on the unpaired strand (protospacer), preferentially closer to the 5' end.

FIG. 3A. Changing the targeting module from dCas9 to nCas9$_{D10A}$ (SEQ ID No: 52) increased the efficiency of the system in terms of survival fraction on rifampicin plates from 18 ($^{AID}$CRC) to 43 fold ($^{AID}$CRC$_{D10A}$) over the control when targeted with rpoB_TS-4 gRNA. FIG. 3B. Mutation distribution of $^{AID}$CRC$_{D10A}$ treatment with rpoB_TS-4 as target (SEQ ID Nos: 30-32). C1592 was modified in 100% of the clones, 75% mutated C to T and 25% mutated C to A.

FIG. 4A. APOBEC3G ($^{APO3G}$CRC$_{D10A}$) and APOBEC1 ($^{APO3G}$CRC$_{D10A}$) were tested as effector side by side with the prototype system, $^{AID}$CRC. Treatment with APOBEC1 increased the mutation frequency over $^{AID}$CRC$_{D10A}$ when targeted with rpoB_TS-4 gRNA. $^{APO3G}$CRC$_{D10A}$ was less active than $^{AID}$CRC. FIG. 4B. Mutation distribution (in %) of $^{APO1}$CRC$_{D10A}$ treatment with rpoB_TS-4 as target (SEQ ID Nos: 30-32). C1592>T conversion was observer in 100% of the clones. In addition, 25% of analyzed clones were double mutants, converting C1590>T, without amino acid change.

FIG. 5A. Increasing the number of recruiting scaffolds while targeting the same position increased the mutation efficiency from 50-(rpoB_TS-4 1×MS2, SEQ ID No: 2) to 140-(rpoB_TS-4 2×MS2, SEQ ID No: 54) fold over their respective scramble gRNA control. FIG. 5B. Mutation distribution (in %) of $^{AID}$CRC$_{D10A}$ treatment with rpoB_TS-4_2×MS2 as target (SEQ ID Nos: 30-32). C1592 was modified in 100% of the clones, 62.5% mutated C to T and 37.5% mutated C to A.

FIG. 6A. Schematic representation of constructs used in these experiments. (Top) Protein coding genes were cloned under the control of the human ubiquitin C promoter (UbC) as a multicistronic construct to ensure stoichiometric concentrations of the two protein components of the system. (Bottom) Chimeric gRNA_MS2 constructs were cloned under the control of a U6 or H1 promoters, to express targets with 5'-G or 5'-A, respectively. FIG. 6B. Schematic of target region around $_{nf}$EGFP$^{Y66C}$ deficient fluorophore. Shown are (top) binding sites of gRNAs used in these experiments, all gRNAs were programmed to target the non-template strand (NT, +); (middle) DNA sequence (SEQ ID Nos: 42 and 43), with PAMs (boxed) and mutable positions (arrow) shown; (bottom) protein sequence (SEQ ID No: 44) with mutant amino acid that abolishes EGFP fluorescence shown (arrow). FIG. 6C. $_{nf}$EGFP$^{Y66C}$ targeting in 293T cells. Treatment with $_{nf}$EGFP$^{Y66C}$_NT-1, and with less efficiency with $_{nf}$EGFP$^{Y66C}$_NT-2 induced EGFP signal, while no signal was detected with scramble gRNA. In addition, the CRC platform was compared with a different gene editing system (BE3), which requires a direct fusion of the cytidine deaminase protein to Cas9 protein for recruitment and requires a co-expression of an inhibitor of uracil DNA glycosylase (UGI) to improve efficiency. BF, bright field. FIG. 6D. Quantitation of GFP positive cells (in %) from treatments with $^{AID}$CRC$_{D10A}$ and BE3 systems, using $_{nf}$EGFP$^{Y66C}$NT-1 as targeting gRNA.

FIG. 7A. Schematic of target region on exon 3 of the Chinese hamster HPRT gene. Shown are (top) DNA sequence (SEQ ID Nos:45 and 46), with PAM (boxed) and mutable position (arrow) shown; (middle) binding site of gRNA used in these experiments, the gRNA was programmed to target the template strand (TS, −); (bottom) protein sequence (SEQ ID No: 47) with a critical amino acid involved in HPRT protein instability (arrow) shown. FIG. 7B. Quantitation of 6-TG resistant V79-4 cells after HPRT targeting with $^{AID}$CRC$_{D10A}$, BE3 or without treatment. When compared to untreated cells, the survival fraction in $^{AID}$CRC$_{D10A}$ treatment was 140-fold higher than untreated cells, while BE3 was 40-fold higher.

FIGS. 8A and 8B are schematic of a cis double nicking approach. FIG. 8A. In this example, the target cytidine (Red) is in position 2 from the 5' end of the protospacer, which makes it inaccessible to the CRC effector module. FIG. 8B. Upper panel. In order to expose the target cytidine to make it more accessible to the effector module, the system is multiplexed to target nearby sequences in cis, upstream and downstream of the target nucleotide. It is possible to exclude the effector module from the second site simply by using a gRNA without the recruitment module (RNA scaffold). Middle panel. After simultaneous cis double nicking, a stretch of ssDNA is transiently generated. In this way, the effector module can gain access to the target cytidine, catalyzing the deamination reaction, mutating the target nucleotide to T (black). nCas9$_{D10A}$ nicking sites are shown with black arrowheads. Lower panel. The converted nucleotide is fixed after the nicked strand is repaired.

FIG. 9A. Schematic of target region along RRDR Cluster I of *E. coli*'s rpoB gene (SEQ ID Nos: 23 and 24). Shown are (top) DNA sequence (SEQ ID No: 23), with PAMs (boxed) in green and mutable positions (arrows) in red; (middle) binding sites of gRNAs used in these experiments. All gRNAs were programmed to target the template strand (TS, −); (bottom) protein sequence (SEQ ID No: 25) in blue with critical amino acids (arrows) involved in rifampicin resistance in red. In this experiment, gRNAs TS2 and TS3 were used. FIG. 9B. Mutation frequency of cis double nicking compared to single nicking. For double nicking experiments, two versions of gRNAs TS2 and TS3 were engineered with and without recruiting RNA motif (2×MS2) to recruit or exclude the effector module (AID_MCP), respectively. Cis double nicking plus recruiting the effector module to position TS3 (treatment TS2/TS3_2×MS2) slightly increased mutation frequency compared to single targeting with TS3_2×MS2 gRNA. Importantly, cis double nicking plus recruitment of the effector module to position TS2 (treatment TS2_2×MS2/TS3) increased the mutation frequency by 130-fold compared to single targeting with TS2_2×MS2 treatment.

FIG. 10A. CRC effectors are recruited to both nicking sites. FIG. 10B. CRC effectors can be recruited to or excluded from nicking sites by employing gRNAs with or without recruiting RNA motifs. Upper panel shows CRC effector being recruited exclusively to downstream nicking site, whereas in the lower panel the CRC effector is recruited only to upstream nicking site. FIG. 10C. In order to further enhance nucleotide conversion efficiency, the system can be programmed to recruit a CRC effector (downstream) and a local DNA repair inhibitor (e.g. UGI). To avoid crosstalk between the two nicking sites, it is possible to use orthogonal RNA recruiting motifs to recruit the CRC effector and the inhibitor independently (e.g. MS2-MCP recruits CRC effector fused to MCP and PP7-PCP recruits UGI fused to PCP). FIG. 10D. If double nicking is required, but there is no other *S. pyogenes* PAM sequence in the vicinity, a Cas9 ortholog can be used depending of which PAM sequence is available. In this example, *S. thermophilus* Cas9 (StCas9$_{D10A}$) is programmed to target the upstream nicking site, while *S. pyogenes* Cas9 (SpCas9$_{D10A}$) targets the downstream nicking site.

DETAILED DESCRIPTION OF THE INVENTION

Figure 1A:
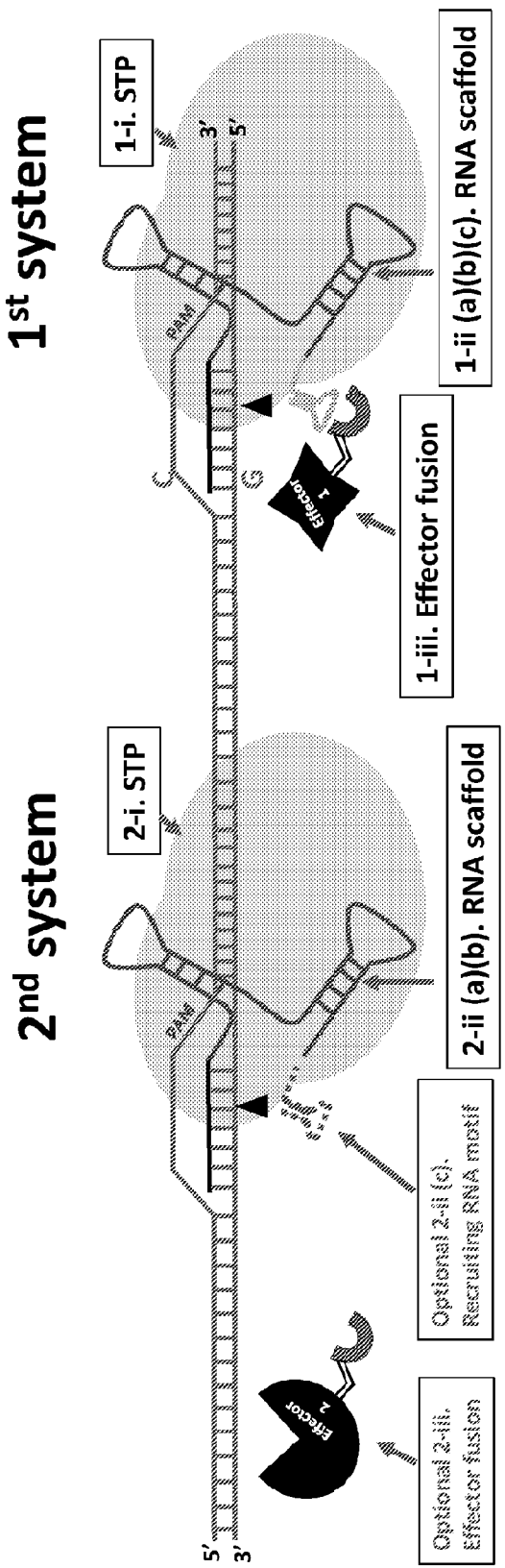
FIG. 1A is a schematic illustration of a gene editing machinery comprising two systems that interact with two specific nucleic acid sequences respectively in a target DNA. The first system contains (i) a sequence-targeting, single-strand DNA (ssDNA) nicking protein (STP), (ii) a RNA scaffold comprising: (a) a nucleic acid-targeting motif comprising a guide RNA sequence that is complementary to a target nucleic acid sequence in the target DNA, (b) a CRISPR motif capable of binding to the sequence-targeting protein, and (c) a recruiting RNA motif, and (iii) a non-nuclease effector fusion protein, comprising: (a) a RNA binding domain capable of binding to the recruiting RNA motif, (b) a linker, and (c) an effector domain. A C-G pair is shown for illustration only, while an A-T pair can be suitable too. The second system may contain a similar set of components as the first system that recognize the second specific nucleic acid sequence, with the component (ii) (c), i.e., the recruiting RNA motif, and the component (iii), i.e. the non-nuclease effector fusion protein, being optional.

Current gene-specific editing technologies are mostly based on nucleases-induced DNA DSB and resulting DSB-induced homologous recombination. As the activity of homologous recombination is low or absent in most somatic cells, these technologies have limited use for therapeutic corrections of pathological genetic mutations in somatic tissues in most diseases.

As disclosed herein, this invention is based, at least in part, on a novel platform or system that allows DNA-sequence directed editing of a gene or RNA transcript. The system does not rely on nuclease activity, does not generate DSB, and does not rely on the DSB-mediated homologous recombination. Moreover, this design of the RNA scaffold of the platform is modular, which allows extremely flexible and convenient way of targeting any desirable DNA or RNA sequences. In essence, this approach enables one to guide a DNA or RNA editing enzyme to virtually any DNA or RNA sequence in somatic cells, including stem cells. Through precise editing the target DNA or RNA sequence, the enzyme can correct mutated genes in genetic disorders, inactivate a viral genome in virus-infected cells, eliminate expression of a disease-causing protein in neurodegenerative diseases, or silence an oncogenic protein in cancers. In addition, this approach can be used for cell-based therapy by editing the genome of a stem cell or progenitor cell ex vivo. In addition to therapeutic application, the system can be broadly applied to targeted modification of genomes of any organism as a powerful research tool. See also PCT/US2016/042413 the content of which is incorporated herein by reference in its entirety.

Gene Editing Platform

One aspect of this invention provides a gene editing platform, which overcomes the above mentioned limitations of current nuclease and DSB dependent genome-engineering and gene-editing technologies. The platform, which is named the CasRcure system or CRC system, has three functional components: (1) a nuclease defective CRISPR/Cas-based module engineered for sequence targeting; (2) a RNA scaffold-based module for guiding the platform to the target sequence as well as for recruitment of a correction module; and (3) a non-nuclease DNA/RNA modifying enzyme as an effector correction module, such as cytidine deaminases (e.g., activation-induced cytidine deaminase, AID). Together, the CasRcure system allows specific DNA/RNA sequencing anchoring, flexible and modular recruitment of effector DNA/RNA modifying enzymes to specific sequences, and eliciting cellular pathways that are active in somatic cells for correcting genetic information, in particular point mutation.

Illustrated in FIGS. 1B-1F are a schematic of an exemplary CasRcure system. More specifically, the system includes three structural and functional components summarized in FIG. 1B: (1) a sequence targeting module (e.g., a dCas9 protein); (2) an RNA scaffold for sequence recognition and for effector recruitment (an RNA molecule that contains a guide RNA motif, a CRISPR RNA motif, and a recruiting RNA motif), and (3) an effector (a non-nuclease DNA modifying enzyme such as AID fused to a small protein that binds to the recruiting RNA motif). The three components could be constructed in a single expression vector or in two to three separate expression vectors. The totality and the combination of the three specific components constitute the enabling of the technologic platform.

As disclosed herein, there are a number of clear distinctions between recruitment mechanisms: RNA scaffold mediated recruitment system (CRC) versus direct fusion of Cas9 to effector protein (BE3). The results shown in the examples below indicate that RNA scaffold mediated recruitment is more efficient than direct fusion in both extrachromosomal targets (FIGS. 6C and 6D) and endogenous genes (FIG. 7B). In addition, the CRC system does not rely on UNG inhibition, a DNA repair enzyme, while BE3 uses a potent UNG inhibitor peptide (UGI). Global or local DNA repair inhibition could lead to undesirable, uncontrollable, potentially deleterious outcomes. Also, the modular design of the CRC system allows for flexible system engineering. Modules are interchangeable and many combinations of different modules can be achieved with ease. Direct fusion, on the other hand, always requires a new fusion process to engineer new modules. Furthermore, RNA scaffold mediated recruitment likely facilitates oligomerization of effector proteins, while direct fusion would preclude the formation of oligomers due to steric hindrance.

a. Sequence-Targeting Module

The sequence targeting component of the above system is based on CRISPR/Cas systems from bacterial species. The original functional bacterial CRISPR-Cas system requires three components: the Cas protein which provides the nuclease activity and two short, non-coding RNA species referred to as CRISPR RNA (crRNAs) and trans-acting RNA (tracrRNA), which two RNA species form a so-called guide RNA (gRNA). Type II CRISPR is one of the most well characterized systems and carries out targeted DNA double-strand break in four sequential steps. First, two non-coding RNAs, a pre-crRNA and a tracrRNA, are transcribed from a CRISPR locus. Second, the tracrRNA hybridizes to the repeat regions of the pre-crRNA molecules and mediates processing of pre-crRNA molecules into mature crRNA molecules containing individual spacer sequences. Third, a mature crRNA:tracrRNA complex (i.e., the so-called guide RNA) directs a Cas nuclease (such as Cas9) to target DNA via Watson-Crick base-pairing between the spacer sequence on the crRNA and the complement of the protospacer sequence on the target DNA, which comprises a 3-nucleotide (nt) protospacer adjacent motif (PAM). PAM sequences are essential for Cas9 targeting. Finally, the Cas nuclease mediates cleavage of the target DNA to create a double-stranded break within the target site. In its native context, a CRISPR/Cas system acts as an adaptive immune system that protects bacteria from repeated viral infections, and PAM sequences serve as self/non-self-recognition signals, and Cas9 protein has nuclease activity. CRISPR/Cas systems have been shown to have enormous potential for gene editing, both in vitro and in vivo.

In the invention disclosed herein, the sequence recognition mechanism can be achieved in a similar manner. That is, a mutant Cas protein, for example, a dCas9 protein which contains mutations at its nuclease catalytic domains thus does not have nuclease activity, or a nCas9 protein which is partially mutated at one of the catalytic domains thus does not have nuclease activity for generating DSB, specifically recognizes a non-coding RNA scaffold molecule containing a short spacer sequence, typically 20 nucleotides in length, which guides the Cas protein to its target DNA or RNA sequence. The latter is flanked by a 3' PAM.

Various Cas proteins can be used in this invention. A Cas protein, CRISPR-associated protein, or CRISPR protein, used interchangeably, refers to a protein of or derived from a CRISPR-Cas type I, type II, or type III system, which has an RNA-guided DNA-binding. Non-limiting examples of suitable CRISPR/Cas proteins include Cas3, Cas4, Cas5, Cas5e (or CasD), Cas6, Cas6e, Cas6f, Cas7, Cas8a1, Cas8a2, Cas8b, Cas8c, Cas9, Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cu1966. See e.g., WO2014144761, WO2014144592, WO2013176772, US20140273226, and US20140273233, the contents of which are incorporated herein by reference in their entireties.

In one embodiment, the Cas protein is derived from a type II CRISPR-Cas system. In exemplary embodiments, the Cas protein is or is derived from a Cas9 protein. The Cas9 protein can be from *Streptococcus pyogenes, Streptococcus thermophilus, Streptococcus* sp., *Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus,* or *Acaryochloris marina.*

In general, a Cas protein includes at least one RNA binding domain. The RNA binding domain interacts with the guide RNA. The Cas protein can be a wild type Cas protein or a modified version with no nuclease activity. The Cas protein can be modified to increase nucleic acid binding affinity and/or specificity, alter an enzymatic activity, and/or change another property of the protein. For example, nuclease (i.e., DNase, RNase) domains of the protein can be modified, deleted, or inactivated. Alternatively, the protein can be truncated to remove domains that are not essential for the function of the protein. The protein can also be truncated or modified to optimize the activity of the effector domain.

In some embodiments, the Cas protein can be a mutant of a wild type Cas protein (such as Cas9) or a fragment thereof. In other embodiments, the Cas protein can be derived from a mutant Cas protein. For example, the amino acid sequence of the Cas9 protein can be modified to alter one or more properties (e.g., nuclease activity, affinity, stability, etc.) of the protein. Alternatively, domains of the Cas9 protein not involved in RNA targeting can be eliminated from the protein such that the modified Cas9 protein is smaller than the wild type Cas9 protein. In some embodiments, the present system utilizes the Cas9 protein from *S. pyogenes*, either as encoded in bacteria or codon-optimized for expression in mammalian cells A mutant Cas protein refers to a polypeptide derivative of the wild type protein, e.g., a protein having one or more point mutations, insertions, deletions, truncations, a fusion protein, or a combination thereof. The mutant has at least one of the RNA-guided DNA binding activity, or RNA-guided nuclease activity, or both. In general, the modified version is at least 50% (e.g., any number between 50% and 100%, inclusive, e.g., 50%, 60%, 70%, 75%, 80%, 85%, 90%, 95%, and 99%) identical to the wild type protein such as SEQ ID No. 1 below.

A Cas protein (as well as other protein components described in this invention) can be obtained as a recombinant polypeptide. To prepare a recombinant polypeptide, a nucleic acid encoding it can be linked to another nucleic acid encoding a fusion partner, e.g., glutathione-s-transferase (GST), 6x-His epitope tag, or M13 Gene 3 protein. The resultant fusion nucleic acid expresses in suitable host cells a fusion protein that can be isolated by methods known in the art. The isolated fusion protein can be further treated, e.g., by enzymatic digestion, to remove the fusion partner and obtain the recombinant polypeptide of this invention. Alternatively, the proteins can be chemically synthesized (see e.g., Creighton, "Proteins: Structures and Molecular Principles," W. H. Freeman & Co., NY, 1983), or produced by recombinant DNA technology as described herein. For additional guidance, skilled artisans may consult Frederick M. Ausubel et al., Current Protocols in Molecular Biology, John Wiley & Sons, 2003; and Sambrook et al., Molecular Cloning, A Laboratory Manual," Cold Spring Harbor Press, Cold Spring Harbor, NY, 2001).

The Cas protein described in the invention can be provided in purified or isolated form, or can be part of a composition. Preferably, where in a composition, the proteins are first purified to some extent, more preferably to a high level of purity (e.g., about 80%, 90%, 95%, or 99% or higher). Compositions according to the invention can be any type of composition desired, but typically are aqueous compositions suitable for use as, or inclusion in, a composition for RNA-guided targeting. Those of skill in the art are well aware of the various substances that can be included in such nuclease reaction compositions.

Figure 1B:
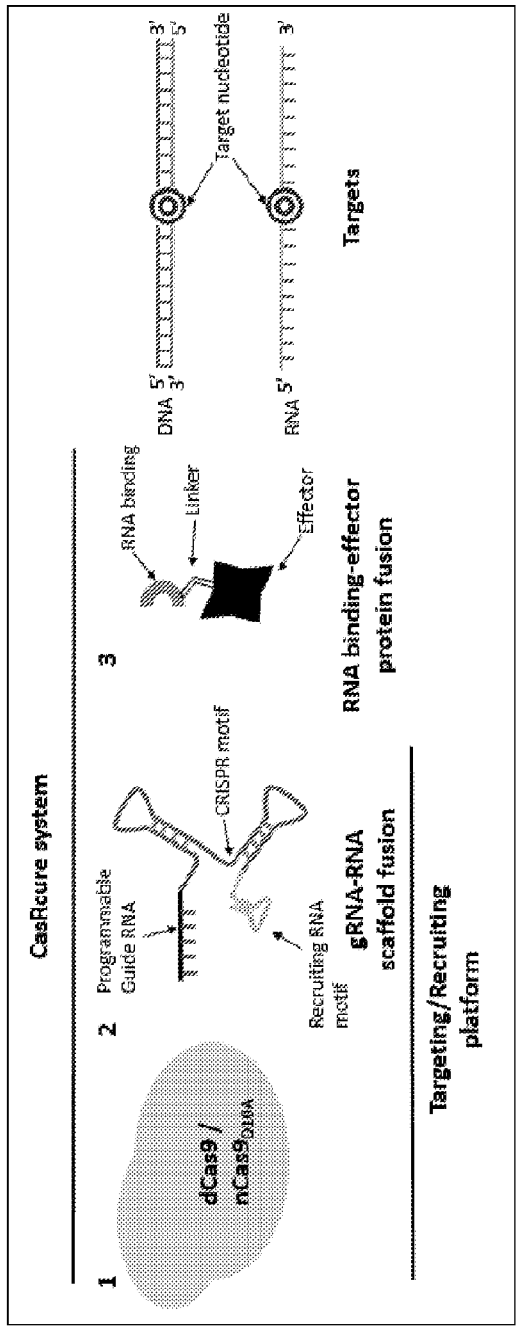
Figure 2A:
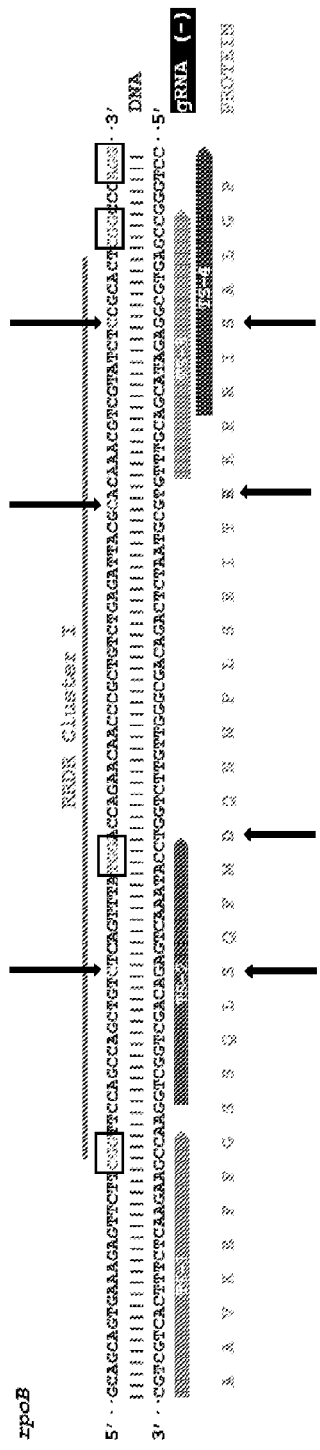
FIGS. 2A, 2B, 2C, 2D, 2E, and 2F show that targeted recruitment of AID is able to introduce site-specific conversion of nucleotide conversion.
Figure 2B:
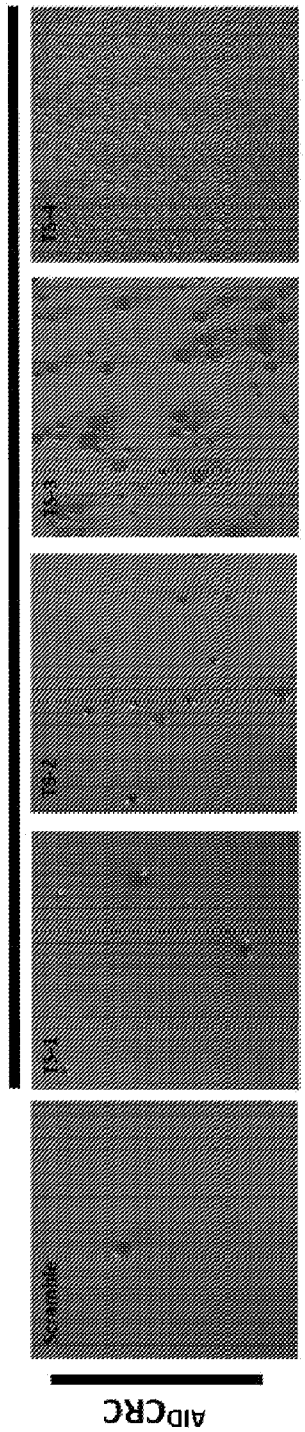
Figure 2C:
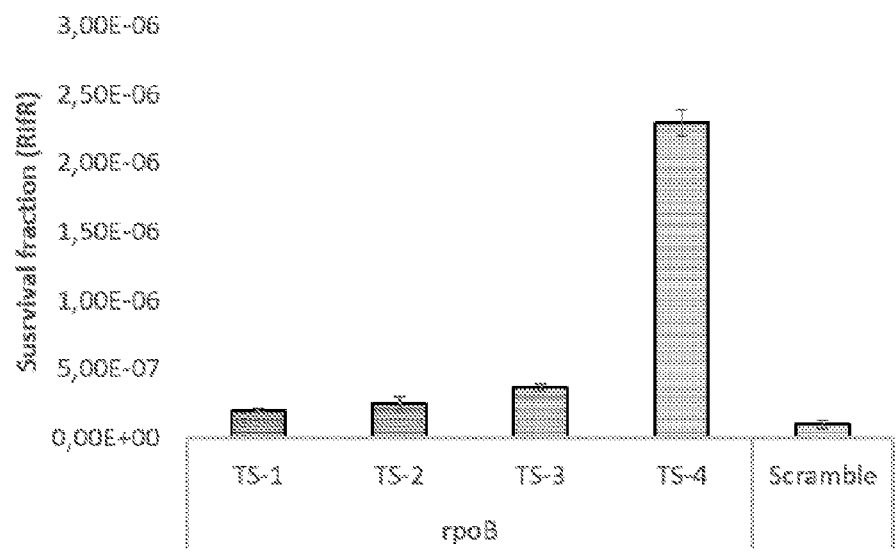
Figure 2D:
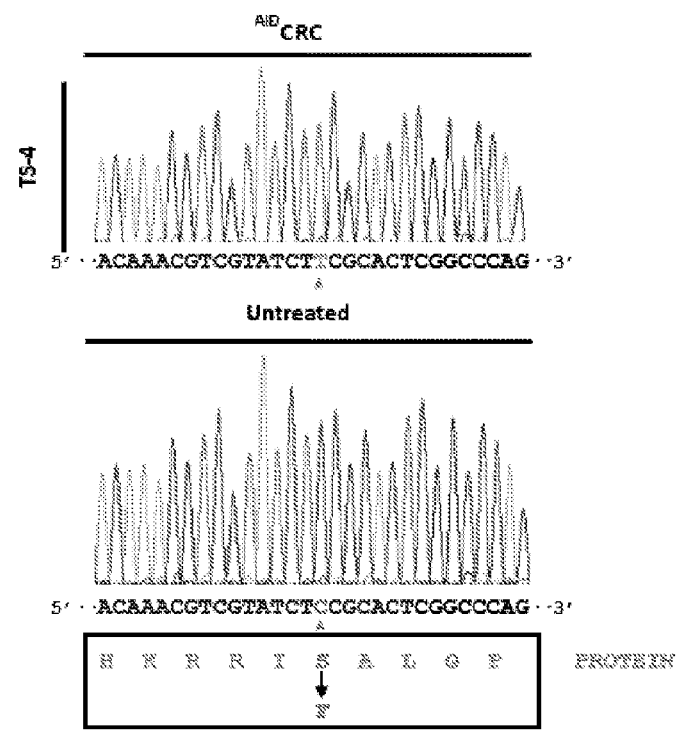
Figures 2E, 2F:
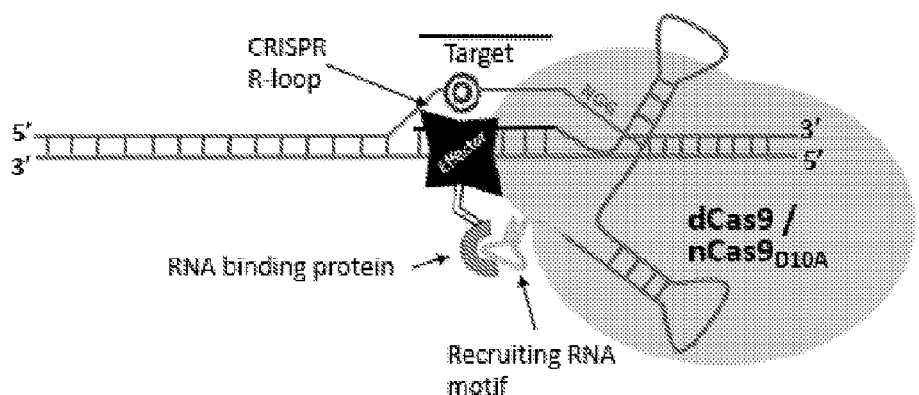

As disclosed here, one can use the nuclease dead Cas9 (dCas9, for example from *S. pyogenes* D10A, H840A mutant protein, FIG. 1B, SEQ ID No: 1), or the nuclease defective nickase Cas9 (nCas9, for example from *S. pyogenes* D10A mutant protein, SEQ ID No: 52, FIG. 1B and FIG. 2F). dCas9 or nCas9 could also be derived from various bacterial species. Table 1 lists a non-exhausting list of examples of dCas9, and their corresponding PAM requirements.

TABLE 1

| Species | PAM |
|---|---|
| *Streptococcus pyogenes* | NGG |
| *Streptococcus agalactiae* | NGG |
| *Staphylococcus aureus* | NNGRRT |
| *Streptococcus thermophilus* | NNAGAAW |
| *Streptococcus thermophilus* | NGGNG |
| *Neisseria meningitidis* | NNNNGATT |
| *Treponema denticola* | NAAAAC |
| Other Type II CRISPR/Cas9 systems from other bacterial species | | b. RNA Scaffold for Sequence Recognition and Effector Recruitment:

The second component of the platform disclosed herein is an RNA scaffold, which has three sub-components: a programmable guide RNA motif, a CRISPR RNA motif, and a recruiting RNA motif. This scaffold can be either a single RNA molecule or a complex of multiple RNA molecules. As disclosed herein, the programmable guide RNA, CRISPR RNA and the Cas protein together form a CRISPR/Cas-based module for sequence targeting and recognition, while the recruiting RNA motif via an RNA-protein binding pair recruits a protein effector, which carries out genetic correction. Accordingly, this second component connects the correction module and sequence recognition module.

Programmable Guide RNA

One key sub-component is the programmable guide RNA. Due to its simplicity and efficiency, the CRISPR-Cas system has been used to perform genome-editing in cells of various organisms. The specificity of this system is dictated by base-pairing between a target DNA and a custom-designed guide RNA. By engineering and adjusting the base-pairing properties of guide RNAs, one can target any sequences of interest provided that there is a PAM sequence in a target sequence.

Among the sub-components of the RNA scaffold disclosed herein, the guide sequence provides the targeting specificity. It includes a region that is complementary and capable of hybridization to a pre-selected target site of interest. In various embodiments, this guide sequence can comprise from about 10 nucleotides to more than about 25 nucleotides. For example, the region of base pairing between the guide sequence and the corresponding target site sequence can be about 10, 11, 12, 13, 14, 15, 16, 17, 18, 19, 20, 22, 23, 24, 25, or more than 25 nucleotides in length. In an exemplary embodiment, the guide sequence is about 17-20 nucleotides in length, such as 20 nucleotides.

One requirement for selecting a suitable target nucleic acid is that it has a 3' PAM site/sequence. Each target sequence and its corresponding PAM site/sequence are referred herein as a Cas-targeted site. Type II CRISPR system, one of the most well characterized systems, needs only Cas 9 protein and a guide RNA complementary to a target sequence to affect target cleavage. The type II CRISPR system of *S. pyogenes* uses target sites having N12-20NGG, where NGG represent the PAM site from *S. pyogenes*, and N12-20 represents the 12-20 nucleotides directly 5' to the PAM site. Additional PAM site sequences from other species of bacteria include NGGNG, NNNNGATT, NNAGAA, NNAGAAW, and NAAAAC. See, e.g., US 20140273233, WO 2013176772, Cong et al., (2012), Science 339 (6121): 819-823, Jinek et al., (2012), Science 337 (6096): 816-821, Mali et al, (2013), Science 339 (6121): 823-826, Gasiunas et al., (2012), Proc Natl Acad Sci USA. 109 (39): E2579-E2586, Cho et al., (2013) Nature Biotechnology 31, 230-232, Hou et al., Proc Natl Acad Sci USA. 2013 Sep. 24; 110(39):15644-9, Mojica et al., Microbiology. 2009 March; 155(Pt 3):733-40, and www.addgene.org/CRISPR/. The contents of these documents are incorporated herein by reference in their entireties.

The target nucleic acid strand can be either of the two strands on a genomic DNA in a host cell. Examples of such genomic dsDNA include, but are not necessarily limited to, a host cell chromosome, mitochondrial DNA and a stably maintained plasmid. However, it is to be understood that the present method can be practiced on other dsDNA present in a host cell, such as non-stable plasmid DNA, viral DNA, and phagemid DNA, as long as there is Cas-targeted site regardless of the nature of the host cell dsDNA. The present method can be practiced on RNAs too.

CRISPR Motif

Besides the above-described guide sequence, the RNA scaffold of this invention includes additional active or non-active sub-components. In one example, the scaffold has a CRISPR motif with tracrRNA activity. For example, the scaffold can be a hybrid RNA molecule where the above-described programmable guide RNA is fused to a tracrRNA to mimic the natural crRNA:tracrRNA duplex. Shown below is an exemplary hybrid crRNA:tracRNA, sgRNA sequence: 5'-(20nt guide)-GUUUAAGAGCUAUGCUGGAAACAG CAUAGCAAGUUUAAAUAAGGCUAGUCCGUUAU-CAACUUGAAAAAGUGGCACCGAGUCGGU GCUUUUUUU-3' (SEQ ID No: 4; Chen et al. Cell, 2013 Dec. 19; 155(7):1479-91). Various tracrRNA sequences are known in the art and examples include the following tracrR-NAs and active portions thereof. As used herein, an active portion of a tracrRNA retains the ability to form a complex with a Cas protein, such as Cas9 or dCas9. See, e.g., WO2014144592. Methods for generating crRNA-tracrRNA hybrid RNAs are known in the art. See e.g., WO2014099750, US 20140179000, and US 20140273226. The contents of these documents are incorporated herein by reference in their entireties.

```
                                              (SEQ ID No: 5)
GGAACCAUUCAAAACAGCAUAGCAAGUUAAAAUAAGGCUAGUCCGUUAUC
AACUUGAAAAAGUGGCACCGAGUCGGUGC;

(SEQ ID No: 6)
UAGCAAGUUAAAAUAAGGCUAGUCCGUUAUCAACUUGAAAAAGUGGCACC
GAGUCGGUGC;

(SEQ ID No: 7)
AGCAUAGCAAGUUAAAAUAAGGCUAGUCCGUUAUCAACUUGAAAAAGUGG
CACCGAGUCGGUGC;

(SEQ ID No: 8)
CAAAACAGCAUAGCAAGUUAAAAUAAGGCUAGUCCGUUAUCAACUUGAAA
AAGUGGCACCGAGUCGGUGC;

(SEQ ID No: 9)
UAGCAAGUUAAAAUAAGGCUAGUCCGUUAUCAACUUGAAAAAGUG;

(SEQ ID No: 10)
UAGCAAGUUAAAAUAAGGCUAGUCCGUUAUCA;
and (SEQ ID No: 11)
UAGCAAGUUAAAAUAAGGCUAGUCCG.
```

In some embodiments, the tracrRNA activity and the guide sequence are two separate RNA molecules, which together form the guide RNA and related scaffold. In this case, the molecule with the tracrRNA activity should be able to interact with (usually by base pairing) the molecule having the guide sequence.

Recruiting RNA Motif

The third sub-component of the RNA scaffold is the recruiting RNA motif, which links the correction module and sequence recognition module. This linkage is critical for the platform disclosed herein.

One way to recruit effector/DNA editing enzymes to a target sequence is through a direct fusion of an effector protein to dCas9. The direct fusion of effector enzymes ("correction module") to the proteins required for sequence recognition (such as dCas9) has achieved success in sequence specific transcriptional activation or suppression, but the protein-protein fusion design may render spatial hindrance, which is not ideal for enzymes that need to form a multimeric complex for their activities. In fact, most nucleotide editing enzymes (such as AID or APOBEC3G) require formation of dimers, tetramers or higher order oligomers, for their DNA editing catalytic activities. The direct fusion to dCas9, which anchors to DNA in a defined conformation, would hinder the formation of a functional oligomeric enzyme complex at the right location.

In contrast, the platform disclosed herein is based on RNA scaffold-mediated effector protein recruitment. More specifically, the platform takes advantages of various RNA motif/RNA binding protein binding pairs. To this end, a RNA scaffold is designed such that a RNA motif (e.g., MS2 operator motif), which specifically binds to a RNA binding protein (e.g., MS2 coat protein, MCP), is linked to the gRNA-CRISPR scaffold (FIG. 1B).

As a result, this RNA scaffold component of the platform disclosed herein is a designed RNA molecule, which contains not only the gRNA motif for specific DNA/RNA sequence recognition, the CRISPR RNA motif for dCas9 binding, but also the recruiting RNA motif for effector recruiting (FIG. 1B). In this way, recruited-effector protein fusions can be recruited to the target site through their ability to bind to the recruiting RNA motif. Due to the flexibility of RNA scaffold mediated recruitment, a functional monomer, as well as dimer, tetramer, or oligomer could be relatively easy to form near the target DNA or RNA sequence. Example configurations are illustrated in FIG. 1 B-E. These pairs of RNA recruiting motif/binding protein could be derived from naturally occurring sources (e.g., RNA phages, or yeast telomerase) or could be artificially designed (e.g., RNA aptamers and their corresponding binding protein ligands). A non-exhausting list of examples of recruiting RNA motif/RNA binding protein pairs that could be used in the CasRcure system is summarized in Table 2.

TABLE 2

Examples of recruiting RNA motifs that can be used in this invention, as well as their paring RNA binding proteins/protein domains.

| RNA motif | Pairing interacting protein* | Organism |
|---|---|---|
| Telomerase Ku binding motif | Ku | Yeast |
| Telomerase Sm7 binding motif | Sm7 | Yeast |
| MS2 phage operator stem-loop | MS2 Coat Protein (MCP) | Phage |
| PP7 phage operator stem-loop | PP7 coat protein (PCP) | Phage |
| SfMu phage Com stem-loop | Com RNA binding protein | Phage |
| Non-natural RNA aptamer | Corresponding aptamer ligand | Artificially designed |

*Recruited proteins are fused to effector proteins, for examples see Table 3.

The sequences for the above binding pairs are listed below.

```
1. Telomerase Ku biding motif/Ku heterodimer
a. Ku binding hairpin
                                             (SEQ ID No: 12)
5'-TTCTTGTCGTACTTATAGATCGCTACGTTATTTCAATTTTGAAAATC

TGAGTCCTGGGAGTGCGGA-3' b. Ku heterodimer
                                             (SEQ ID No: 13)
MSGWESYYKTEGDEEAEEEQEENLEASGDYKYSGRDSLIFLVDASKAMFE

SQSEDELTPFDMSIQCIQSVYISKIISSDRDLLAVVFYGTEKDKNSVNFK

NIYVLQELDNPGAKRILELDQFKGQQGQKRFQDMMGHGSDYSLSEVLWVC

ANLFSDVQFKMSHKRIMLFTNEDNPHGNDSAKASRARTKAGDLRDTGIFL
```

-continued
```
DLMELKKPGGFDISLFYRDIISIAEDEDLRVHFEESSKLEDLLRKVRAKE

TRKRALSRLKLKLNKDIVISVGIYNLVQKALKPPPIKLYRETNEPVKTKT

RTFNTSTGGLLLPSDTKRSQIYGSRQIILEKEETEELKRFDDPGLMLMGF

KPLVLLKKHHYLRPSLFVYPEESLVIGSSTLFSALLIKCLEKEVAALCRY

TPRRNIPPYFVALVPQEEELDDQKIQVTPPGFQLVFLPFADDKRKMPFTE

KIMATPEQVGKMKAIVEKLRFTYRSDSFENPVLQQHFRNLEALALDLMEP

EQAVDLTLPKVEAMNKRLGSLVDEFKELVYPPDYNPEGKVTKRKHDNEGS

GSKRPKVEYSEEELKTHISKGTLGKFTVPMLKEACRAYGLKSGLKKQELL

EALTKHFQD>
```

(SEQ ID No: 14)
```
MVRSGNKAAVVLCMDVGFTMSNSIPGIESPFEQAKKVITMFVQRQVFAEN

KDEIALVLFGTDGTDNPLSGGDQYQNITVHRHLMLPDFDLLEDIESKIQP

GSQQADFLDALIVSMDVIQHETIGKKFEKRHIEIFTDLSSRFSKSQLDII

IHSLKKCDISERHSIHWPCRLTIGSNLSIRIAAYKSILQERVKKTWTVVD

AKTLKKEDIQKETVYCLNDDDETEVLKEDIIQGFRYGSDIVPFSKVDEEQ

MKYKSEGKCFSVLGFCKSSQVQRRFFMGMQVLKVFAARDDEAAAVALSSL

IHALDDLDMVAIVRYAYDKRANPQVGVAFPHIKHNYECLVYVQLPFMEDL

RQYMFSSLKNSKKYAPTEAQLNAVDALIDSMSLAKKDEKTDTLEDLFPTT

KIPNPRFQRLFQCLLHRALHPREPLPPIQQHIWNMLNPPAEVTTKSQIPL

SKIKTLFPLIEAKKKDQVTAQEIFQDNHEDGPTAK
```

2. Telomerase Sm7 biding motif/Sm7 homoheptamer
a. Sm consensus site (single stranded)
(SEQ ID No: 15)
5'-AATTTTTGGA-3' b. Monomeric Sm-like protein (archaea)
(SEQ ID No: 16)
```
GSVIDVSSQRVNVQRPLDALGNSLNSPVIIKLKGDREFRGVLKSFDLHMN

LVLNDAEELEDGEVTRRLGTVLIRGDNIVYISP
```

3. MS2 phage operator stem loop/MS2 coat protein
a. MS2 phage operator stem loop
(SEQ ID No: 17)
5'-GCGCACATGAGGATCACCCATGTGC-3' b. MS2 coat protein
(SEQ ID No: 18)
```
MASNFTQFVLVDNGGTGDVTVAPSNFANGIAEWISSNSRSQAYKVTCSVR

QSSAQNRKYTIKVEVPKGAWRSYLNMELTIPIFATNSDCELIVKAMQGLL

KDGNPIPSAIAANSGIY
```

4. PP7 phage operator stem loop/PP7 coat protein
a. PP7 phage operator stem loop
(SEQ ID No: 19)
5'-aTAAGGAGTTTATATGGAAACCCTTA-3' b. PP7 coat protein (PCP)
(SEQ ID No: 20)
```
MSKTIVLSVGEATRTLTEIQSTADRQIFEEKVGPLVGRLRLTASLRQNGA

KTAYRVNLKLDQADVVDCSTSVCGELPKVRYTQVWSHDVTIVANSTEASR

KSLYDLTKSLVATSQVEDLVVNLVPLGR.
```

5. SfMu Com stem loop/SfMu Com binding protein
a. SfMu Com stem loop (SEQ ID No: 21)
5'-CTGAATGCCTGCGAGCATC-3' b. SfMu Corn binding protein
(SEQ ID No: 22)
```
MKSIRCKNCNKLLFKADSFDHIEIRCPRCKRHIIMLNACEHPTEKHCGKR

EKITHSDETVRY
```

The RNA scaffold can be either a single RNA molecule or a complex of multiple RNA molecules. For example, the guide RNA, CRISPR motif, and recruiting RNA motif can be three segments of one, long single RNA molecule. Alternatively, one, two or three of them can be on separate molecules. In the latter case, the three components can be linked together to form the scaffold via covalent or non-covalent linkage or binding, including e.g., Watson-Crick base-pairing.

In one example, the RNA scaffold can comprise two separate RNA molecules. The first RNA molecule can comprise the programmable guide RNA and a region that can form a stem duplex structure with a complementary region. The second RNA molecule can comprise the complementary region in addition to the CRISPR motif and the recruiting DNA motif. Via this stem duplex structure, the first and second RNA molecules form a RNA scaffold of this invention. In one embodiment, the first and second RNA molecules each comprise a sequence (of about 6 to about 20 nucleotides) that base pairs to the other sequence. By the same token, the CRISPR motif and the recruiting DNA motif can also be on different RNA molecule and be brought together with another stem duplex structure.

The RNAs and related scaffold of this invention can be made by various methods known in the art including cell-based expression, in vitro transcription, and chemical synthesis. The ability to chemically synthesize relatively long RNAs (as long as 200 mers or more) using TC-RNA chemistry (see, e.g., U.S. Pat. No. 8,202,983) allows one to produce RNAs with special features that outperform those enabled, by the basic four ribonucleotides (A, C, G and U).

The Cas protein-guide RNA scaffold complexes can be made with recombinant technology using a host cell system or an in vitro translation-transcription system known in the art. Details of such systems and technology can be found in e.g., WO2014144761 WO2014144592, WO2013176772, US20140273226, and US20140273233, the contents of which are incorporated herein by reference in their entireties. The complexes can be isolated or purified, at least to some extent, from cellular material of a cell or an in vitro translation-transcription system in which they are produced.

The RNA scaffold may include one or more modifications. Such modifications may include inclusion of at least one non-naturally occurring nucleotide, or a modified nucleotide, or analogs thereof. Modified nucleotides may be modified at the ribose, phosphate, and/or base moiety. Modified nucleotides may include 2'-O-methyl analogs, 2'-deoxy analogs, or 2'-fluoro analogs. The nucleic acid backbone may be modified, for example, a phosphorothioate backbone may be used. The use of locked nucleic acids (LNA) or bridged nucleic acids (BNA) may also be possible. Further examples of modified bases include, but are not limited to, 2-aminopurine, 5-bromo-uridine, pseudouridine, inosine, 7-methylguanosine. These modifications may apply to any component of the CRISPR system. In a preferred embodiment these modifications are made to the RNA components, e.g. the guide RNA sequence.

c. Effectors: Non-Nuclease DNA Modifying Enzymes

The third component of the platform disclosed in this invention is a non-nuclease effector. The effector is not a nuclease and does not have any nuclease activity, but can have the activity of other types of DNA modifying enzymes. Examples of the enzymatic activity include, but are not limited to, deamination activity, methyltransferase activity, demethylase activity, DNA repair activity, DNA damage activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity. In some embodiments, the effector has the activity of cytidine deaminases (e.g., AID, APOBEC3G), adenosine deaminases (e.g., ADA), DNA methyltransferases, and DNA demethylases.

In preferred embodiments, this third component is a conjugate or a fusion protein that has an RNA-binding domain and an effector domain. These two domains can be joined via a linker.

RNA-Binding Domain

Although various RNA-binding domains can be used in this invention, the RNA-binding domain of Cas protein (such as Cas9) or its variant (such as dCas9) should not be used. As mentioned above, the direct fusion to dCas9, which anchors to DNA in a defined conformation, would hinder the formation of a functional oligomeric enzyme complex at the right location. Instead, the present invention takes advantages of various other RNA motif-RNA binding protein binding pairs. Examples include those listed in Table 2.

In this way, the effector protein can be recruited to the target site through RNA-binding domain's ability to bind to the recruiting RNA motif. Due to the flexibility of RNA scaffold mediated recruitment, a functional monomer, as well as dimer, tetramer, or oligomer could be formed relatively easily near the target DNA or RNA sequence.

Effector Domain

The effector component comprises an activity portion, i.e., an effector domain. In some embodiments, the effector domain comprises the naturally-occurring activity portion of a non-nuclease protein (e.g., deaminases). In other embodiments, the effector domain comprises a modified amino acid sequence (e.g., substitution, deletion, insertion) of a naturally-occurring activity portion of a non-nuclease protein. The effector domain has an enzymatic activity. Examples of this activity include deamination activity, methyltransferase activity, demethylase activity, DNA repair activity, DNA damage activity, dismutase activity, alkylation activity, depurination activity, oxidation activity, pyrimidine dimer forming activity, integrase activity, transposase activity, recombinase activity, polymerase activity, ligase activity, helicase activity, photolyase activity, glycosylase activity, DNA methylation, histone acetylation activity, or histone methylation activity. Some modifications in non-nuclease protein (e.g., deaminases) can help reduce off-target effect. For example, as described below, one can reduce the recruitment of AID to off-target sites by mutating Ser38 in AID to Ala (SEQ ID NO: 51).

Linker

The above-mentioned two domains as well as others as disclosed herein can be joined by means of linkers, such as, but not limited to chemical modification, peptide linkers, chemical linkers, covalent or non-covalent bonds, or protein fusion or by any means known to one skilled in the art. The joining can be permanent or reversible. See for example U.S. Pat. Nos. 4,625,014, 5,057,301 and 5,514,363, U.S. Application Nos. 20150182596 and 20100063258, and WO2012142515, the contents of which are incorporated herein in their entirety by reference. In some embodiments, several linkers can be included in order to take advantage of desired properties of each linker and each protein domain in the conjugate. For example, flexible linkers and linkers that increase the solubility of the conjugates are contemplated for use alone or with other linkers. Peptide linkers can be linked by expressing DNA encoding the linker to one or more protein domains in the conjugate. Linkers can be acid cleavable, photocleavable and heat sensitive linkers. Methods for conjugation are well known by persons skilled in the art and are encompassed for use in the present invention.

In some embodiments, the RNA-binding domain and the effector domain can be joined by a peptide linker. Peptide linkers can be linked by expressing nucleic acid encoding in frame the two domains and the linker. Optionally the linker peptide can be joined at either or both of the amino terminus and carboxy terminus of the domains. In some examples, a linker is an immunoglobulin hinge region linker as disclosed in U.S. Pat. Nos. 6,165,476, 5,856,456, U.S. Application Nos. 20150182596 and 2010/0063258 and International Application WO2012/142515, each of which are incorporated herein in their entirety by reference.

Other Domains

The effector fusion protein can comprise other domains. In certain embodiments, the effector fusion protein can comprise at least one nuclear localization signal (NLS). In general, an NLS comprises a stretch of basic amino acids. Nuclear localization signals are known in the art (see, e.g., Lange et al., J. Biol. Chem., 2007, 282:5101-5105). The NLS can be located at the N-terminus, the C-terminal, or in an internal location of the fusion protein.

In some embodiments, the fusion protein can comprise at least one cell-penetrating domain to facilitate delivery of the protein into a target cell. In one embodiment, the cell-penetrating domain can be a cell-penetrating peptide sequence. Various cell-penetrating peptide sequences are known in the art and examples include that of the HIV-1 TAT protein, TLM of the human HBV, Pep-1, VP22, and a polyarginine peptide sequence.

In still other embodiments, the fusion protein can comprise at least one marker domain. Non-limiting examples of marker domains include fluorescent proteins, purification tags, and epitope tags. In some embodiments, the marker domain can be a fluorescent protein. In other embodiments, the marker domain can be a purification tag and/or an epitope tag. See, e.g., US 20140273233.

In one embodiment, AID was used as an example to illustrate how the system works. AID is a cytidine deaminase that can catalyze the reaction of deamination of cytidine in the context of DNA or RNA. When brought to the targeted site, AID changes a C base to U base. In dividing cells, this could lead to a C to T point mutation. Alternatively, the change of C to U could trigger cellular DNA repair pathways, mainly excision repair pathway, which will remove the mismatching U-G base-pair, and replace with a T-A, A-T, C-G, or G-C pair. As a result, a point mutation would be generated at the target C-G site. As excision repair pathway is present in most, if not all, somatic cells, recruitment of AID to the target site can correct a C-G base pair to others. In that case, if a C-G base pair is an underlying disease causing genetic mutation in somatic tissues/cells, the above-described approach can be used to correct the mutation and thereby treat the disease.

By the same token, if an underlying disease causing genetic mutation is an A-T base pair at a specific site, one can use the same approach to recruit an adenosine deaminase to the specific site, where adenosine deaminase can correct the A-T base pair to others. Other effector enzymes are expected to generate other types of changes in base-pairing. A non-exhausting list of examples of DNA/RNA modifying enzymes is detailed in Table 3.

TABLE 3

Examples of effector proteins that can be used in this invention

| Enzyme type | Genetic change | Effector protein abbreviated |
|---|---|---|
| Cytidine deaminase | C→U/T | AID APOBEC1 APOBEC3A APOBEC3B APOBEC3C APOBEC3D APOBEC3F APOBEC3G APOBEC3H |
| Adenosine deaminase | A→I/G | ADA ADAR1 |
| DNA Methyl transferase | C→Met-C | Dnmt1 Dnmt3a Dnmt3b |
| Demethylase | Met-C→C | Tet1 |

Effector protein full names:
AID: activation induced cytidine deaminase, a.k.a AICDA.
APOBEC1: apolipoprotein B mRNA editing enzyme, catalytic polypeptide-like 1.
APOBEC3A: apolipoprotein B mRNA editing enzyme, catalytic polypeptide-like 3A
APOBEC3B: apolipoprotein B mRNA editing enzyme, catalytic polypeptide-like 3B
APOBEC3C: apolipoprotein B mRNA editing enzyme, catalytic polypeptide-like 3C
APOBEC3D: apolipoprotein B mRNA editing enzyme, catalytic polypeptide-like 3D
APOBEC3F: apolipoprotein B mRNA editing enzyme, catalytic polypeptide-like 3F
APOBEC3G: apolipoprotein B mRNA editing enzyme, catalytic polypeptide-like 3G
APOBEC3H: apolipoprotein B mRNA editing enzyme, catalytic polypeptide-like 3H
ADA: adenosine deaminase
ADAM: adenosine deaminase acting on RNA 1
Dnmt1: DNA (cytosine-5-)-methyltransferase 1
Dnmt3a: DNA (cytosine-5-)-methyltransferase 3 alpha
Dnmt3b: DNA (cytosine-5-)-methyltransferase 3 beta
Tet1: methylcytosine dioxygenase The above-described three specific components constitute the technological platform. Each component could be chosen from the list in Table 1-3 respectively to achieve a specific therapeutic/utility goal.

In one example, a CasRcure system was constructed using (i) dCas9 from *S. pyogenes* as the sequence targeting protein, (ii) a RNA scaffold containing a guide RNA sequence, a CRISPR RNA motif, and a MS2 operator motif, and (iii) an effector fusion containing a human AID fusing to MS2 operator binding protein MCP. The sequences for the components are listed below

*S. pyogenes* dCas9 protein sequence
(SEQ ID No. 1)
MDKKYSIGLAIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDAIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD (Residues underlined: D10A,

H840A active site mutants)

Cas9 D10A Protein (residues underlined: D10A, SEQ
ID No: 52)
DKKYSIGLAIGTNSVGWAVITDEYKVPSKKFKVLGNTDRHSIKKNLIGAL

LFDSGETAEATRLKRTARRRYTRRKNRICYLQEIFSNEMAKVDDSFFHRL

EESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPI

NASGVDAKAILSARLSKSRRLENLIAQLPGEKKNGLFGNLIALSLGLTPN

FKSNFDLAEDAKLQLSKDTYDDDLDNLLAQIGDQYADLFLAAKNLSDAIL

LSDILRVNTEITKAPLSASMIKRYDEHHQDLTLLKALVRQQLPEKYKEIF

FDQSKNGYAGYIDGGASQEEFYKFIKPILEKMDGTEELLVKLNREDLLRK

QRTFDNGSIPHQIHLGELHAILRRQEDFYPFLKDNREKIEKILTFRIPYY

VGPLARGNSRFAWMTRKSEETITPWNFEEVVDKGASAQSFIERMTNFDKN

LPNEKVLPKHSLLYEYFTVYNELTKVKYVTEGMRKPAFLSGEQKKAIVDL

LFKTNRKVTVKQLKEDYFKKIECFDSVEISGVEDRFNASLGTYHDLLKII

KDKDFLDNEENEDILEDIVLTLTLFEDREMIEERLKTYAHLFDDKVMKQL

KRRRYTGWGRLSRKLINGIRDKQSGKTILDFLKSDGFANRNFMQLIHDDS

LTFKEDIQKAQVSGQGDSLHEHIANLAGSPAIKKGILQTVKVVDELVKVM

GRHKPENIVIEMARENQTTQKGQKNSRERMKRIEEGIKELGSQILKEHPV

ENTQLQNEKLYLYYLQNGRDMYVDQELDINRLSDYDVDHIVPQSFLKDDS

IDNKVLTRSDKNRGKSDNVPSEEVVKKMKNYWRQLLNAKLITQRKFDNLT

KAERGGLSELDKAGFIKRQLVETRQITKHVAQILDSRMNTKYDENDKLIR

EVKVITLKSKLVSDFRKDFQFYKVREINNYHHAHDAYLNAVVGTALIKKY

PKLESEFVYGDYKVYDVRKMIAKSEQEIGKATAKYFFYSNIMNFFKTEIT

LANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEK

GKSKKLKSVKELLGITIMERSSFEKNPIDFLEAKGYKEVKKDLIIKLPKY

SLFELENGRKRMLASAGELQKGNELALPSKYVNFLYLASHYEKLKGSPED

NEQKQLFVEQHKHYLDEIIEQISEFSKRVILADANLDKVLSAYNKHRDKP

IREQAENIIHLFTLTNLGAPAAFKYFDTTIDRKRYTSTKEVLDATLIHQS

ITGLYETRIDLSQLGGD

DNA encoding Cas9 D10A Protein (SEQ ID No: 53)

GATAAAAAGTATTCTATTGGTTTAGCCATCGGCACTAATTCCGTTGGATG

GGCTGTCATAACCGATGAATACAAAGTACCTTCAAAGAAATTTAAGGTGT

TGGGGAACACAGACCGTCATTCGATTAAAAAGAATCTTATCGGTGCCCTC

CTATTCGATAGTGGCGAAACGGCAGAGGCGACTCGCCTGAAACGAACCGC

TCGGAGAAGGTATACACGTCGCAAGAACCGAATATGTTACTTACAAGAAA

TTTTTAGCAATGAGATGGCCAAAGTTGACGATTCTTTCTTTCACCGTTTG

GAAGAGTCCTTCCTTGTCGAAGAGGACAAGAAACATGAACGGCACCCCAT

CTTTGGAAACATAGTAGATGAGGTGGCATATCATGAAAAGTACCCAACGA

TTTATCACCTCAGAAAAAGCTAGTTGACTCAACTGATAAAGCGGACCTG

AGGTTAATCTACTTGGCTCTTGCCCATATGATAAAGTTCCGTGGGCACTT

TCTCATTGAGGGTGATCTAAATCCGGACAACTCGGATGTCGACAAACTGT

TCATCCAGTTAGTACAAACCTATAATCAGTTGTTTGAAGAGAACCCTATA

AATGCAAGTGGCGTGGATGCGAAGGCTATTCTTAGCGCCCGCCTCTCTAA

ATCCCGACGGCTAGAAAACCTGATCGCACAATTACCCGGAGAGAAGAAAA

ATGGGTTGTTCGGTAACCTTATAGCGCTCTCACTAGGCCTGACACCAAAT

TTTAAGTCGAACTTCGACTTAGCTGAAGATGCCAAATTGCAGCTTAGTAA

GGACACGTACGATGACGATCTCGACAATCTACTGGCACAAATTGGAGATC

AGTATGCGGACTTATTTTTGGCTGCCAAAAACCTTAGCGATGCAATCCTC

CTATCTGACATACTGAGAGTTAATACTGAGATTACCAAGGCGCCGTTATC

CGCTTCAATGATCAAAAGGTACGATGAACATCACCAAGACTTGACACTTC

TCAAGGCCCTAGTCCGTCAGCAACTGCCTGAGAAATATAAGGAAATATTC

TTTGATCAGTCGAAAAACGGGTACGCAGGTTATATTGACGGCGGAGCGAG

TCAAGAGGAATTCTACAAGTTTATCAAACCCATATTAGAAGATGGATG

GGACGGAAGAGTTGCTTGTAAAACTCAATCGCGAAGATCTACTGCGAAAG

CAGCGGACTTTCGACAACGGTAGCATTCCACATCAAATCCACTTAGGCGA

ATTGCATGCTATACTTAGAAGGCAGGAGGATTTTTATCCGTTCCTCAAAG

ACAATCGTGAAAAGATTGAGAAAATCCTAACCTTTCGCATACCTTACTAT

GTGGGACCCCTGGCCCGAGGGAACTCTCGGTTCGCATGGATGACAAGAAA

GTCCGAAGAAACGATTACTCCATGGAATTTTGAGGAAGTTGTCGATAAAG

GTGCGTCAGCTCAATCGTTCATCGAGAGGATGACCAACTTTGACAAGAAT

TTACCGAACGAAAAAGTATTGCCTAAGCACAGTTTACTTTACGAGTATTT

CACAGTGTACAATGAACTCACGAAAGTTAAGTATGTCACTGAGGGCATGC

GTAAACCCGCCTTTCTAAGCGGAGAACAGAAGAAAGCAATAGTAGATCTG

TTATTCAAGACCAACCGCAAAGTGACAGTTAAGCAATTGAAAGAGGACTA

CTTTAAGAAAATTGAATGCTTCGATTCTGTCGAGATCTCCGGGGTAGAAG

ATCGATTTAATGCGTCACTTGGTACGTATCATGACCTCCTAAAGATAATT

AAAGATAAGGACTTCCTGGATAACGAAGAGAATGAAGATATCTTAGAAGA

TATAGTGTTGACTCTTACCCTCTTTGAAGATCGGGAAATGATTGAGGAAA

GACTAAAAACATACGCTCACCTGTTCGACGATAAGGTTATGAAACAGTTA

AAGAGGCGTCGCTATACGGGCTGGGGACGATTGTCGCGGAAACTTATCAA

CGGGATAAGAGACAAGCAAAGTGGTAAAACTATTCTCGATTTTCTAAAGA

GCGACGGCTTCGCCAATAGGAACTTTATGCAGCTGATCCATGATGACTCT

TTAACCTTCAAAGAGGATATACAAAAGGCACAGGTTTCCGGACAAGGGGA

CTCATTGCACGAACATATTGCGAATCTTGCTGGTTCGCCAGCCATCAAAA

AGGGCATACTCCAGACAGTCAAAGTAGTGGATGAGCTAGTTAAGGTCATG

GGACGTCACAAACCGGAAAACATTGTAATCGAGATGGCACGCGAAAATCA

AACGACTCAGAAGGGGCAAAAAAACAGTCGAGAGCGGATGAAGAGAATAG

AAGAGGGTATTAAAGAACTGGGCAGCCAGATCTTAAAGGAGCATCCTGTG

GAAAATACCCAATTGCAGAACGAGAAACTTTACCTCTATTACCTACAAAA

TGGAAGGGACATGTATGTTGATCAGGAACTGGACATAAACCGTTTATCTG

ATTACGACGTCGATCACATTGTACCCCAATCCTTTTTGAAGGACGATTCA

ATCGACAATAAAGTGCTTACACGCTCGGATAAGAACCGAGGGAAAAGTGA

CAATGTTCCAAGCGAGGAAGTCGTAAAGAAAATGAAGAACTATTGGCGGC

AGCTCCTAAATGCGAAACTGATAACGCAAAGAAAGTTCGATAACTTAACT

AAAGCTGAGAGGGGTGGCTTGTCTGAACTTGACAAGGCCGGATTTATTAA

ACGTCAGCTCGTGGAAACCCGCCAAATCACAAAGCATGTTGCACAGATAC

TAGATTCCCGAATGAATACGAAATACGACGAGAACGATAAGCTGATTCGG

GAAGTCAAAGTAATCACTTTAAAGTCAAAATTGGTGTCGGACTTCAGAAA

GGATTTTCAATTCTATAAAGTTAGGGAGATAAATAACTACCACCATGCGC

ACGACGCTTATCTTAATGCCGTCGTAGGGACCGCACTCATTAAGAAATAC

CCGAAGCTAGAAAGTGAGTTTGTGTATGGTGATTACAAAGTTTATGACGT

CCGTAAGATGATCGCGAAAAGCGAACAGGAGATAGGCAAGGCTACAGCCA

AATACTTCTTTTATTCTAACATTATGAATTTCTTTAAGACGGAAATCACT

CTGGCAAACGGAGAGATACGCAAACGACCTTTAATTGAAACCAATGGGGA

GACAGGTGAAATCGTATGGGATAAGGGCCGGGACTTCGCGACGGTGAGAA

AAGTTTTGTCCATGCCCCAAGTCAACATAGTAAAGAAAACTGAGGTGCAG

ACCGGAGGGTTTTCAAAGGAATCGATTCTTCCAAAAAGGAATAGTGATAA

GCTCATCGCTCGTAAAAGGACTGGGACCCGAAAAGTACGGTGGCTTCG

ATAGCCCTACAGTTGCCTATTCTGTCCTAGTAGTGGCAAAAGTTGAGAAG

GGAAAATCCAAGAAACTGAAGTCAGTCAAAGAATTATTGGGGATAACGAT

TATGGAGCGCTCGTCTTTTGAAAAGAACCCCATCGACTTCCTTGAGGCGA

```
AAGGTTACAAGGAAGTAAAAAAGGATCTCATAATTAAACTACCAAAGTAT

AGTCTGTTTGAGTTAGAAAATGGCCGAAAACGGATGTTGGCTAGCGCCGG

AGAGCTTCAAAAGGGGAACGAACTCGCACTACCGTCTAAATACGTGAATT

TCCTGTATTTAGCGTCCCATTACGAGAAGTTGAAAGGTTCACCTGAAGAT

AACGAACAGAAGCAACTTTTTGTTGAGCAGCACAAACATTATCTCGACGA

AATCATAGAGCAAATTTCGGAATTCAGTAAGAGAGTCATCCTAGCTGATG

CCAATCTGGACAAAGTATTAAGCGCATACAACAAGCACAGGGATAAACCC

ATACGTGAGCAGGCGGAAAATATTATCCATTTGTTTACTCTTACCAACCT

CGGCGCTCCAGCCGCATTCAAGTATTTTGACACAACGATAGATCGCAAAC

GATACACTTCTACCAAGGAGGTGCTAGACGCGACACTGATTCACCAATCC

ATCACGGGATTATATGAAACTCGGATAGATTTGTCACAGCTTGGGGGTGA

C
```

RNA scaffold expression cassette (*S. pyogenes*), containing a 20-nucleotide programmable sequence, a CRISPR RNA motif, and an MS2 operator motif (SEQ ID No. 2):

```
N₂₀GTTTTAGAGCTAGAAATAGCAAGTTAAAATAAGGCTAGTCCGTTATCA
ACTTGAAAAAGTGGCACCGAGTCGGTGCGCGCACATGAGGATCACCCATG
TGCTTTTTTTG
```

(N₂₀: programmable sequence; Underlined: CRISPR RNA motif; Bold: MS2 motif; Italic: terminator)

The above RNA scaffold containing one MS2 loop (1×MS2). Shown below is a RNA scaffold containing two MS2 loops (2×MS2), where MS2 scaffolds are underlined:

```
                                    (SEQ ID No: 54)
GTTTTAGAGCTAGAAATAGCAAGTTAAAATAAGGCTAGTCCGTTATCAAC

TTGAAAAAGTGGCACCGAGTCGGTGCgggagcACATGAGGATCACCCATG

TgccacgagcgACATGAGGATCACCCATGTcgctcgtgttcccTTTTTTT

CTCCGCT
```

Effector AID-MCP fusion (SEQ ID No. 3):
```
MDSLLMNRRKFLYQFKNVRWAKGRRETYLCYVVKRRDSATSFSLDFGYLR

NKNGCHVELLFLRYISDWDLDPGRCYRVTWFTSWSPCYDCARHVADFLRG

NPNLSLRIFTARLYFCEDRKAEPEGLRRLHRAGVQIAIMTFKDYFYCWNT

FVENHERTFKAWEGLHENSVRLSRQLRRILLPLYEVDDLRDAFRTLGL

ELKTPLGDTTHTSPPCPAPELLGGPMASNFTQFVLVDNGGTG

DVTVAPSNFANGIAEWISSNSRSQAYKVTCSVRQSSAQNRKYTIKVEVPK

GAWRSYLNMELTIPIFATNSDCELIVKAMQGLLKDGNPIPSAIAANSGIY (NH₂)-AID-linker-MCP-(COOH)
```

Like the Cas protein described above, the non-nuclease effector can also be obtained as a recombinant polypeptide. Techniques for making recombinant polypeptides are known in the art. See e.g., Creighton, "Proteins: Structures and Molecular Principles," W. H. Freeman & Co., NY, 1983); Ausubel et al., Current Protocols in Molecular Biology, John Wiley & Sons, 2003; and Sambrook et al., Molecular Cloning, A Laboratory Manual," Cold Spring Harbor Press, Cold Spring Harbor, NY, 2001).

As described herein, by mutating Ser38 to Ala in AID one can reduce the recruitment of AID to off-target sites. Listed below are the DNA and protein sequences of both wild type AID as well as AID_S38A (phosphorylation null, pnAID):

```
wtAID cDNA (Ser38 codon in bold and underlined,
SEQ ID NO: 48):
ATGGACAGCCTCTTGATGAACCGGAGGAAGTTTCTTTACCAATTCAAAA

ATGTCCGCTGGGCTAAGGGTCGGCGTGAGACCTACCTGTGCTACGTAGT

GAAGAGGCGTGACAGTGCTACATCCTTTTCACTGGACTTTGGTTATCTT

CGCAATAAGAACGGCTGCCACGTGGAATTGCTCTTCCTCCGCTACATCT

CGGACTGGGACCTAGACCCTGGCCGCTGCTACCGCGTCACCTGGTTCAC

CTCCTGGAGCCCCTGCTACGACTGTGCCCGACATGTGGCCGACTTTCTG

CGAGGGAACCCCAACCTCAGTCTGAGGATCTTCACCGCGCGCCTCTACT

TCTGTGAGGACCGCAAGGCTGAGCCCGAGGGGCTGCGGCGGCTGCACCG

CGCCGGGGTGCAAATAGCCATCATGACCTTCAAAGATTATTTTTACTGC

TGGAATACTTTTGTAGAAAACCATGAAAGAACTTTCAAAGCCTGGGAAG

GGCTGCATGAAAATTCAGTTCGTCTCTCCAGACAGCTTCGGCGCATCCT

TTTGCCCCTGTATGAGGTTGATGACTTACGAGACGCATTTCGTACTTTG

GGACTT wtAID protein (Ser38 in bold and underlined,
SEQ ID NO: 49):
MDSLLMNRRKFLYQFKNVRWAKGRRETYLCYVVKRRDSATSFSLDFGYL

RNKNGCHVELLFLRYISDWDLDPGRCYRVTWFTSWSPCYDCARHVADFL

RGNPNLSLRIFTARLYFCEDRKAEPEGLRRLHRAGVQIAIMTFKDYFYC

WNTFVENHERTFKAWEGLHENSVRLSRQLRRILLPLYEVDDLRDAFRTL

GL

AID_S38A cDNA (S38A mutation in bold and
underlined, SEQ ID NO: 50)
ATGGACAGCCTCTTGATGAACCGGAGGAAGTTTCTTTACCAATTCAAAA

ATGTCCGCTGGGCTAAGGGTCGGCGTGAGACCTACCTGTGCTACGTAGT

GAAGAGGCGTGACGCCGCTACATCCTTTTCACTGGACTTTGGTTATCTT

CGCAATAAGAACGGCTGCCACGTGGAATTGCTCTTCCTCCGCTACATCT

CGGACTGGGACCTAGACCCTGGCCGCTGCTACCGCGTCACCTGGTTCAC

CTCCTGGAGCCCCTGCTACGACTGTGCCCGACATGTGGCCGACTTTCTG

CGAGGGAACCCCAACCTCAGTCTGAGGATCTTCACCGCGCGCCTCTACT

TCTGTGAGGACCGCAAGGCTGAGCCCGAGGGGCTGCGGCGGCTGCACCG

CGCCGGGGTGCAAATAGCCATCATGACCTTCAAAGATTATTTTTACTGC

TGGAATACTTTTGTAGAAAACCATGAAAGAACTTTCAAAGCCTGGGAAG

GGCTGCATGAAAATTCAGTTCGTCTCTCCAGACAGCTTCGGCGCATCCT

TTTGCCCCTGTATGAGGTTGATGACTTACGAGACGCATTTCGTACTTTG

GGACTT

AID_S38A protein (S38A mutation in bold and
underlined, SEQ ID NO: 51)
MDSLLMNRRKFLYQFKNVRWAKGRRETYLCYVVKRRDAATSFSLDFGYL

RNKNGCHVELLFLRYISDWDLDPGRCYRVTWFTSWSPCYDCARHVADFL

RGNPNLSLRIFTARLYFCEDRKAEPEGLRRLHRAGVQTAIMTFKDYFYC
```

-continued

WNTFVENHERTFKAWEGLHENSVRLSRQLRRILLPLYEVDDLRDAFRTL
GL

The above three components of the platform/system disclosed herein can be expressed using one to three expression vectors. The system can be programmed to target virtually any DNA or RNA sequence.

Expression System

To use the platform described above, it may be desirable to express one or more of the protein and RNA components from nucleic acids that encode them. This can be performed in a variety of ways. For example, the nucleic acids encoding the RNA scaffold or proteins can be cloned into one or more intermediate vectors for introducing into prokaryotic or eukaryotic cells for replication and/or transcription. Intermediate vectors are typically prokaryotic vectors, e.g., plasmids, or shuttle vectors, or insect vectors, for storage or manipulation of the nucleic acid encoding the RNA scaffold or protein for production of the RNA scaffold or protein. The nucleic acids can also be cloned into one or more expression vectors, for administration to a plant cell, animal cell, preferably a mammalian cell or a human cell, fungal cell, bacterial cell, or protozoan cell. Accordingly, the present invention provides nucleic acids that encode any of the RNA scaffold or proteins mentioned above. Preferably, the nucleic acids are isolated and/or purified.

The present invention also provides recombinant constructs or vectors having sequences encoding one or more of the RNA scaffold or proteins described above. Examples of the constructs include a vector, such as a plasmid or viral vector, into which a nucleic acid sequence of the invention has been inserted, in a forward or reverse orientation. In a preferred embodiment, the construct further includes regulatory sequences, including a promoter, operably linked to the sequence. Large numbers of suitable vectors and promoters are known to those of skill in the art, and are commercially available. Appropriate cloning and expression vectors for use with prokaryotic and eukaryotic hosts are also described in e.g., Sambrook et al. (2001, Molecular Cloning: A Laboratory Manual, Cold Spring Harbor Press).

A vector refers to a nucleic acid molecule capable of transporting another nucleic acid to which it has been linked. The vector can be capable of autonomous replication or integration into a host DNA. Examples of the vector include a plasmid, cosmid, or viral vector. The vector of this invention includes a nucleic acid in a form suitable for expression of the nucleic acid in a host cell. Preferably the vector includes one or more regulatory sequences operatively linked to the nucleic acid sequence to be expressed. A "regulatory sequence" includes promoters, enhancers, and other expression control elements (e.g., polyadenylation signals). Regulatory sequences include those that direct constitutive expression of a nucleotide sequence, as well as inducible regulatory sequences. The design of the expression vector can depend on such factors as the choice of the host cell to be transformed, transfected, or infected, the level of expression of RNAs or proteins desired, and the like.

Examples of expression vectors include chromosomal, nonchromosomal and synthetic DNA sequences, bacterial plasmids, phage DNA, baculovirus, yeast plasmids, vectors derived from combinations of plasmids and phage DNA, viral DNA such as vaccinia, adenovirus, fowl pox virus, and pseudorabies. However, any other vector may be used as long as it is replicable and viable in the host. The appropriate nucleic acid sequence may be inserted into the vector by a variety of procedures. In general, a nucleic acid sequence encoding one of the RNAs or proteins described above can be inserted into an appropriate restriction endonuclease site(s) by procedures known in the art. Such procedures and related sub-cloning procedures are within the scope of those skilled in the art.

The vector may include appropriate sequences for amplifying expression. In addition, the expression vector preferably contains one or more selectable marker genes to provide a phenotypic trait for selection of transformed host cells such as dihydrofolate reductase or neomycin resistance for eukaryotic cell cultures, or such as tetracycline or ampicillin resistance in *E. coli*.

The vectors for expressing the RNAs can include RNA Pol III promoters to drive expression of the RNAs, e.g., the HI, U6 or 7SK promoters. These human promoters allow for expression of RNAs in mammalian cells following plasmid transfection. Alternatively, a T7 promoter may be used, e.g., for in vitro transcription, and the RNA can be transcribed in vitro and purified.

The vector containing the appropriate nucleic acid sequences as described above, as well as an appropriate promoter or control sequence, can be employed to transform, transfect, or infect an appropriate host to permit the host to express the RNAs or proteins described above. Examples of suitable expression hosts include bacterial cells (e.g., *E. coil, Streptomyces, Salmonella typhimurium*), fungal cells (yeast), insect cells (e.g., *Drosophila* and *Spodoptera frugiperda* (Sf9)), animal cells (e.g., CHO, COS, and HEK 293), adenoviruses, and plant cells. The selection of an appropriate host is within the scope of those skilled in the art. In some embodiments, the present invention provides methods for producing the above mentioned RNAs or proteins by transforming, transfecting, or infecting a host cell with an expression vector having a nucleotide sequence that encodes one of the RNAs, or polypeptides, or proteins. The host cells are then cultured under a suitable condition, which allows for the expression of the RNAs or proteins.

Any of the procedures known in the art for introducing foreign nucleotide sequences into host cells may be used. Examples include the use of calcium phosphate transfection, polybrene, protoplast fusion, electroporation, nucleofection, liposomes, microinjection, naked DNA, plasmid vectors, viral vectors, both episomal and integrative, and any of the other well-known methods for introducing cloned genomic DNA, cDNA, synthetic DNA or other foreign genetic material into a host cell.

Methods

Another aspect of the present invention encompasses a method for modifying a target DNA sequence (e.g., a chromosomal sequence) or target RNA sequence in a cell, embryo, human or non-human animals. The method comprises introducing into the cell or embryo the above-described (i) a sequence-targeting protein, or a polynucleotide encoding the same, (ii) an RNA scaffold, or a DNA polynucleotide encoding the same, and (iii) a non-nuclease effector fusion protein, or a polynucleotide encoding the same. The RNA scaffold guides the sequence-targeting protein and the fusion protein to a target polynucleotide at a target site and the effector domain of the fusion protein modifies the sequence. As disclosed herein, the sequence-targeting protein, such as a cas9 protein, is modified such that the endonuclease activity is eliminated.

Figure 1C:
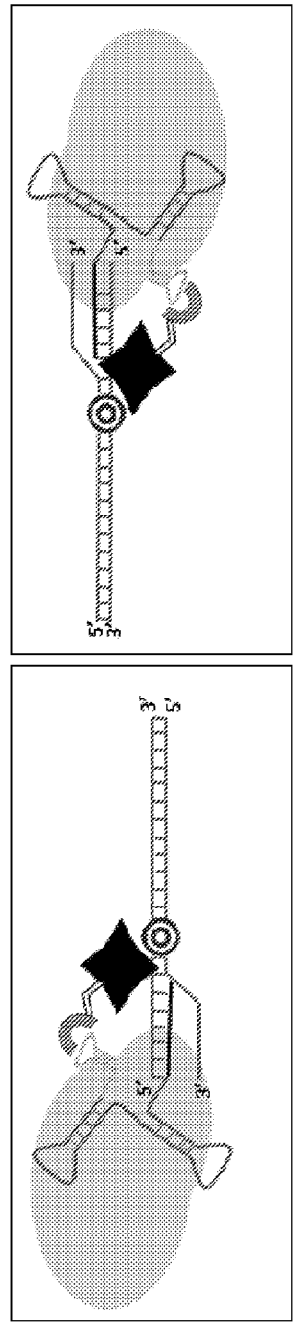

In certain embodiments, the effector protein functions as a monomer. In that case, the system of this invention can be targeted to a single site, either upstream (left) or downstream (right) of the target site as shown in FIG. 1C. In other embodiments, the effector protein requires dimerization for proper catalytic function. To that end, the system can be multiplexed to target sequences upstream and downstream of the target site simultaneously, therefore allowing the effector proteins to dimerize (FIG. 1D, left). Alternatively, recruitment of effector protein to a single site may be sufficient to increase its affinity for neighboring effector proteins, promoting dimerization (FIG. 1D, right). In yet some other embodiments, a tetramer effector enzyme can be recruited and positioned at the target site as shown in FIG. 1E. This can be achieved by dual (FIG. 1E, left) or single targeting (FIG. 1E, right). The system disclosed in this invention can be used to edit RNA targets too (e.g. retrovirus inactivation). See FIG. 1F. In that case, if the effector protein requires assembly of a functional oligomer, single targeting to a RNA molecule could promote oligomerization as in right panels of FIGS. 1D and 1E.

The target polynucleotide has no sequence limitation except that the sequence is immediately followed (downstream or 3') by a PAM sequence. Examples of PAM include, but are not limited to, NGG, NGGNG, and NNAGAAW (wherein N is defined as any nucleotide and W is defined as either A or T). Other examples of PAM sequences are given above, and the skilled person will be able to identify further PAM sequences for use with a given CRISPR protein. The target site can be in the coding region of a gene, in an intron of a gene, in a control region between genes, etc. The gene can be a protein coding gene or an RNA coding gene.

The target polynucleotide can be any polynucleotide endogenous or exogenous to the cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide).

The protein components of this system of this invention can be introduced into the cell or embryo as an isolated protein. In one embodiment, each protein can comprise at least one cell-penetrating domain, which facilitates cellular uptake of the protein. In other embodiments, mRNA molecules or DNA molecules encoding the protein or proteins can be introduced into the cell or embryo. In general, a DNA sequence encoding the protein is operably linked to a promoter sequence that will function in the cell or embryo of interest. The DNA sequence can be linear, or the DNA sequence can be part of a vector. In still other embodiments, the protein can be introduced into the cell or embryo as an RNA-protein complex comprising the protein and the RNA scaffold described above.

In alternate embodiments, DNA encoding the protein(s) can further comprise a sequence or sequences encoding components of the RNA scaffold. In general, the DNA sequence encoding the protein and the RNA scaffold is operably linked to appropriate promoter control sequences that allow the expression of the protein and the RNA scaffold, respectively, in the cell or embryo. The DNA sequence encoding the protein and the RNA scaffold can further comprise additional expression control, regulatory, and/or processing sequence(s). The DNA sequence encoding the protein and the guiding RNA can be linear or can be part of a vector.

In embodiments in which the RNA is introduced into the cell via a DNA molecule encoding the RNA, the RNA coding sequence can be operably linked to promoter control sequence for expression of the guiding RNA in the eukaryotic cell. For example, the RNA coding sequence can be operably linked to a promoter sequence that is recognized by RNA polymerase III (Pol III). Examples of suitable Pol III promoters include, but are not limited to, mammalian U6 or H1 promoters. In exemplary embodiments, the RNA coding sequence is linked to a mouse or human U6 promoter. In other exemplary embodiments, the RNA coding sequence is linked to a mouse or human H1 promoter.

The DNA molecule encoding the protein and/or RNA can be linear or circular. In some embodiments, the DNA sequence can be part of a vector. Suitable vectors include plasmid vectors, phagemids, cosmids, artificial/mini-chromosomes, transposons, and viral vectors. In an exemplary embodiment, the DNA encoding the protein and/or RNA is present in a plasmid vector. Non-limiting examples of suitable plasmid vectors include pUC, pBR322, pET, pBluescript, and variants thereof. The vector can comprise additional expression control sequences (e.g., enhancer sequences, Kozak sequences, polyadenylation sequences, transcriptional termination sequences, etc.), selectable marker sequences (e.g., antibiotic resistance genes), origins of replication, and the like.

The proteins components of this system of this invention (or nucleic acid(s) encoding them) and the RNA components (or DNAs encoding them) can be introduced into a cell or embryo by a variety of means. Typically, the embryo is a fertilized one-cell stage embryo of the species of interest. In some embodiments, the cell or embryo is transfected. Suitable transfection methods include calcium phosphate-mediated transfection, nucleofection (or electroporation), cationic polymer transfection (e.g., DEAE-dextran or polyethylenimine), viral transduction, virosome transfection, virion transfection, liposome transfection, cationic liposome transfection, immunoliposome transfection, non-liposomal lipid transfection, dendrimer transfection, heat shock transfection, magnetofection, lipofection, gene gun delivery, impalefection, sonoporation, optical transfection, and proprietary agent-enhanced uptake of nucleic acids. Transfection methods are well known in the art (see, e.g., "Current Protocols in Molecular Biology" Ausubel et al., John Wiley & Sons, New York, 2003 or "Molecular Cloning: A Laboratory Manual" Sambrook & Russell, Cold Spring Harbor Press, Cold Spring Harbor, N.Y., 3rd edition, 2001). In other embodiments, the molecules are introduced into the cell or embryo by microinjection. For example, the molecules can be injected into the pronuclei of one cell embryos.

The proteins components of this system of this invention (or nucleic acid(s) encoding them) and the RNA components (or DNAs encoding them) can be introduced into a cell or embryo simultaneously or sequentially. The ratio of the protein (or its encoding nucleic acid) to the RNA (or DNAs encoding the RNA), generally will be approximately stoichiometric such that they can form an RNA-protein complex. Similarly, the ratio of two different proteins (or encoding nucleic acids) will be approximately stoichiometric. In one embodiment, the protein components and the RNA components (or the DNA sequence encoding them) are delivered together within the same nucleic acid or vector.

The method further comprises maintaining the cell or embryo under appropriate conditions such that the guide RNA guides the effector protein to the targeted site in the target sequence, and the effector domain modifies the target sequence.

In general, the cell can be maintained under conditions appropriate for cell growth and/or maintenance. Suitable cell culture conditions are well known in the art and are described, for example, in Current Protocols in Molecular Biology" Ausubel et al., John Wiley & Sons, New York, 2003 or "Molecular Cloning: A Laboratory Manual" Sambrook & Russell, Cold Spring Harbor Press, Cold Spring Harbor, N.Y., 3rd edition, 2001), Santiago et al. (2008) PNAS 105:5809-5814; Moehle et al. (2007) PNAS 104: 3055-3060; Urnov et al. (2005) Nature 435:646-651; and Lombardo et al. (2007) Nat. Biotechnology 25:1298-1306. Those of skill in the art appreciate that methods for culturing cells are known in the art and can and will vary depending on the cell type. Routine optimization may be used, in all cases, to determine the best techniques for a particular cell type.

An embryo can be cultured in vitro (e.g., in cell culture). Typically, the embryo is cultured at an appropriate temperature and in appropriate media with the necessary $O_2/CO_2$ ratio to allow the expression of the proteins and RNA scaffold, if necessary. Suitable non-limiting examples of media include M2, M16, KSOM, BMOC, and HTF media. A skilled artisan will appreciate that culture conditions can and will vary depending on the species of embryo. Routine optimization may be used, in all cases, to determine the best culture conditions for a particular species of embryo. In some cases, a cell line may be derived from an in vitro-cultured embryo (e.g., an embryonic stem cell line).

Alternatively, an embryo may be cultured in vivo by transferring the embryo into a uterus of a female host. Generally speaking, the female host is from the same or similar species as the embryo. Preferably, the female host is pseudo-pregnant. Methods of preparing pseudo-pregnant female hosts are known in the art. Additionally, methods of transferring an embryo into a female host are known. Culturing an embryo in vivo permits the embryo to develop and can result in a live birth of an animal derived from the embryo. Such an animal would comprise the modified chromosomal sequence in every cell of the body.

A variety of eukaryotic cells are suitable for use in the method. For example, the cell can be a human cell, a non-human mammalian cell, a non-mammalian vertebrate cell, an invertebrate cell, an insect cell, a plant cell, a yeast cell, or a single cell eukaryotic organism. A variety of embryos are suitable for use in the method. For example, the embryo can be a 1-cell, 2-cell, or 4-cell human or non-human mammalian embryo. Exemplary mammalian embryos, including one cell embryos, include without limit mouse, rat, hamster, rodent, rabbit, feline, canine, ovine, porcine, bovine, equine, and primate embryos. In still other embodiments, the cell can be a stem cell. Suitable stem cells include without limit embryonic stem cells, ES-like stem cells, fetal stem cells, adult stem cells, pluripotent stem cells, induced pluripotent stem cells, multipotent stem cells, oligopotent stem cells, unipotent stem cells and others. In exemplary embodiments, the cell is a mammalian cell or the embryo is a mammalian embryo.

One limitation when it comes to target specific nucleotides based on CRISPR is the position of the target nucleotide relative to the closest protospacer adjacent motif (PAM). Ideally, the target nucleotide should be between positions 4 to 8 counting from the 5' end of the protospacer, that is distal from the PAM. However, in practice this might not be possible to achieve for all targets (FIG. 8A). To solve this problem, this invention also provides a system using, e.g., Cas9 nickases (nCas9) as targeting modules that recognize two sequences (guided by gRNA) surrounding the target nucleotide (one gRNA upstream the target site, one downstream the target site), introducing two nicks close to each other in cis i.e. on the same DNA strand. In this way, a stretch of ssDNA will be transiently exposed, allowing a CRC effector module to catalyze the nucleotide conversion, followed by fixation of the introduced modification upon strand repair (FIG. 8B).

This strategy greatly increases the conversion efficiency. It makes it possible to target the sequence that the previously un-targetable or very difficult to target sequence due to the spatial/positional requirement of PAM. In addition, this technology has the following added benefits: (1) programming two gRNAs to target a specific genomic region in a CRC system increases targeting specificity and reduces off-target effects; (2) it allows flexible addition of functional module(s) to the CRC system to synergistically enhance conversion efficiency, increase specificity, and reduce off-target effects.

Figure 9A:
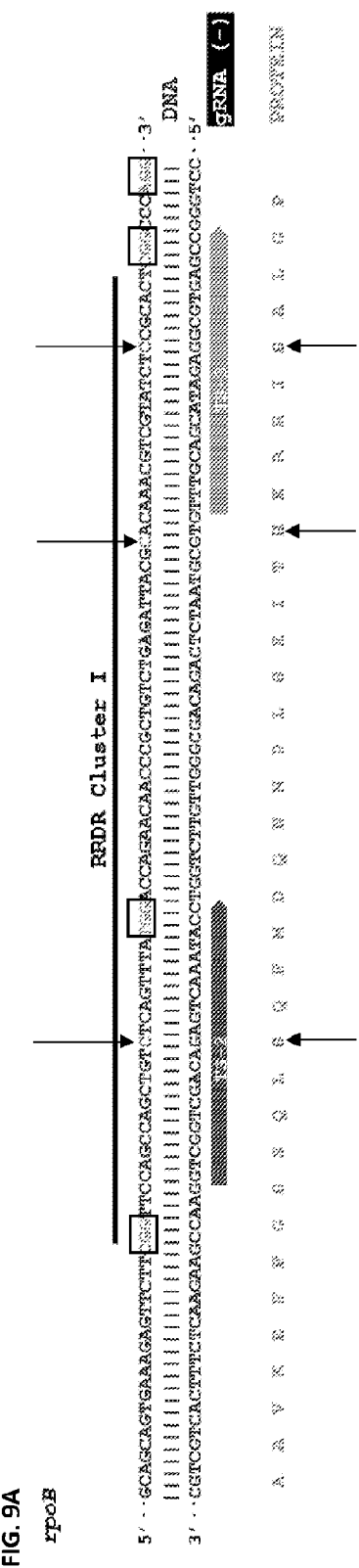
FIGS. 9A and 9B are diagrams showing cis double nicking in bacterial genome.
Figure 9B:
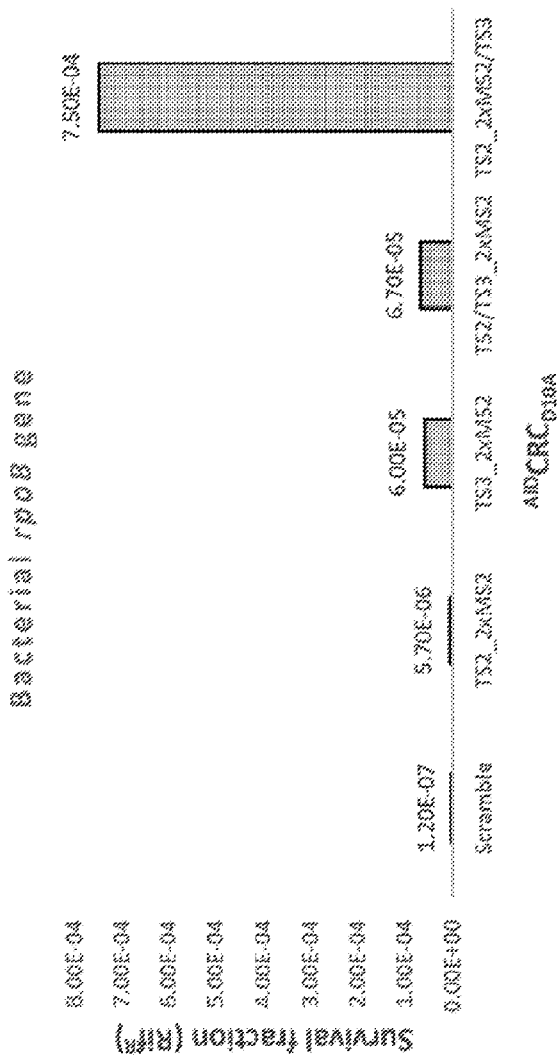

As shown Example 4 below, a study was performed applying this Cis Double Nicking Technology to enhance conversion efficiency in a bacterial gene conversion model (FIG. 9). Experimentally, nCas9 (nCas9$_{D10A}$ or nCas9$_{H840}$) were programmed to target two neighboring positions on the same DNA strand. Double nicking the same strand with two gRNA does not induce double strand DNA breaks or activation of DSB repair pathways, therefore this is a safe approach. A schematic of the procedure is described in FIG. 8. To test this approach, the bacterial gene encoding for the RNA polymerase β subunit (rpoB) was targeted using gRNAs TS-2 and TS-3 (FIG. 9A). This is a negative selection system, in which specific rpoB mutants can be selected using the antibiotic rifampicin since mutants are resistant to this drug (Rif$^R$). The results in prokaryotic cells suggest that targeting efficiency can be enhanced up to 100-fold (FIG. 9B).

Figures 10A, 10B:
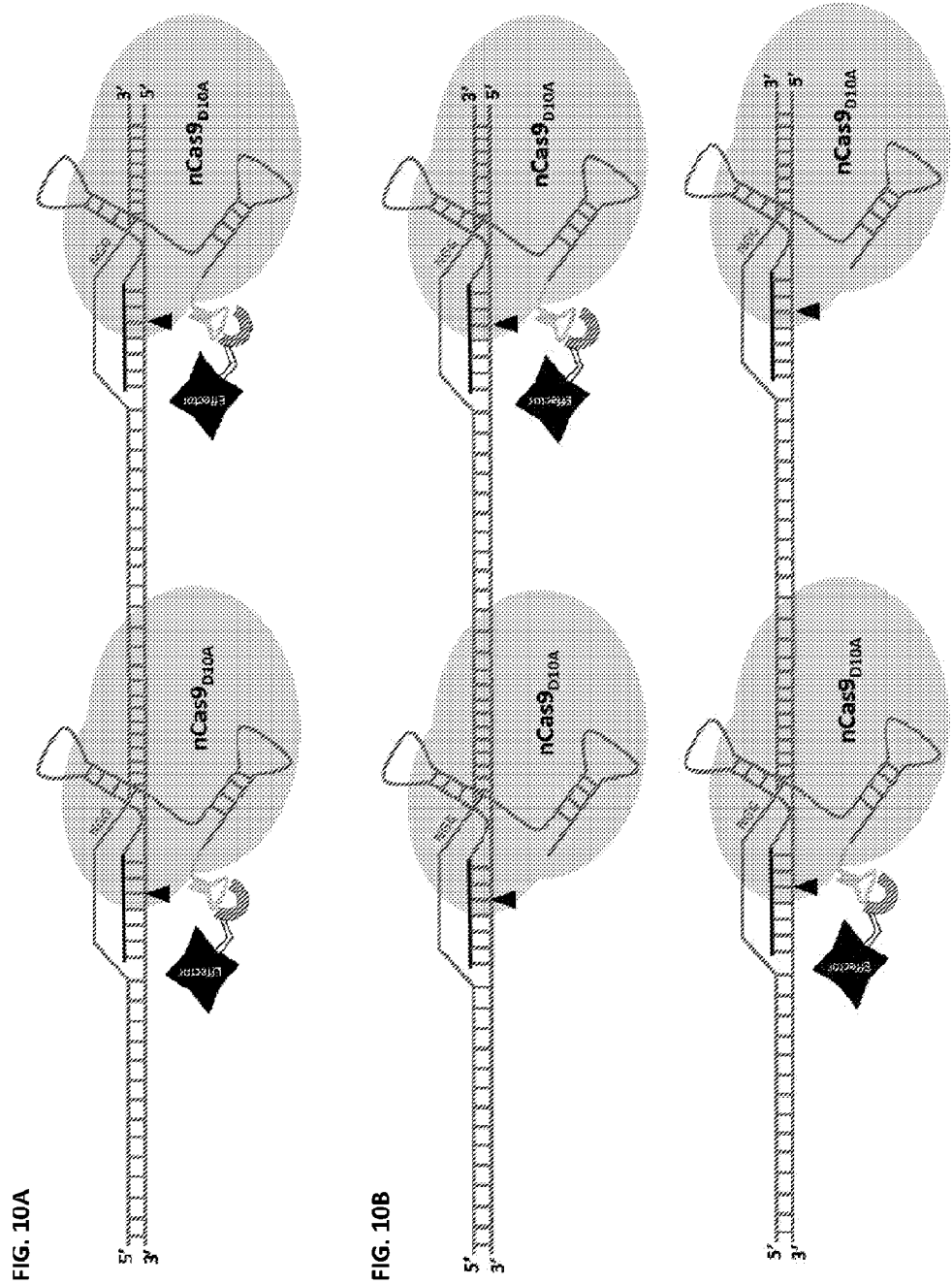
FIGS. 10A, 10B, 10C, and 10D are diagrams showing various applications of CRC system using cis double nicking approach.

By harnessing CRC's modular design, this invention also provides a method that can recruit two effectors (either the same or different) to a target sequence, synergistically enhance the genetic conversion. These designs are exemplified in FIG. 10. For example, both gRNAs can be engineered to have the same recruiting RNA motif (e.g. MS2 scaffold), CRC effector fused to MCP protein can be recruited to both nicking sites (FIG. 10A). This allows one to recruit two identical effectors to the target sequence, increasing local concentration of the effectors or facilitating dimerization or multimerization required for effector functions.

Likewise, this invention also provides a method that can recruit or exclude a CRC effector from any of the nicking sites by selecting gRNAs with or without recruiting RNA motif, respectively (FIGS. 9B and 10B). This allows to recruit one effector but exposing a single stranded DNA, facilitating effector function.

Figure 10C:
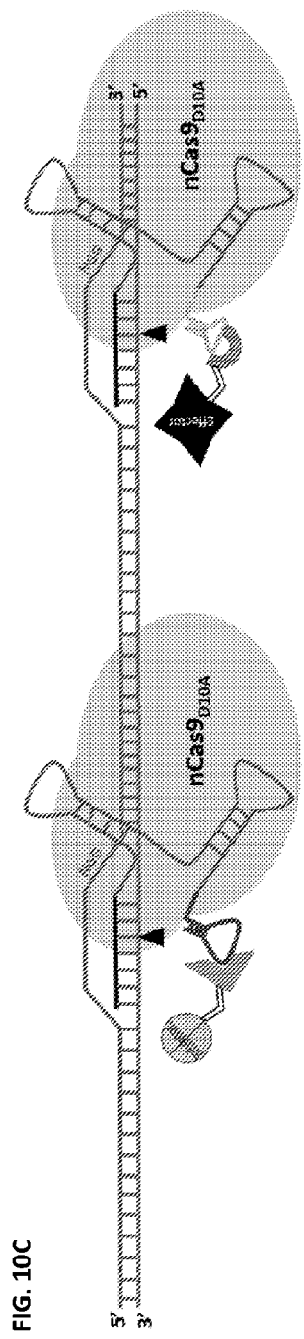

In another example, this invention provides a method that recruits two different functional effectors into the same target sequence. The two effectors work together synergistically to facilitate the genetic conversion. For example, to further increase targeting efficiency, one can program CRC recruitment of a deaminase (e.g. AID) to the nicking site closer to the target nucleotide, and a local DNA repair inhibitor to the second nicking site (e.g. UNG inhibitor, UGI). While the AID facilitates the conversion of, e.g., C to T at the target sequence, the UGI inhibits the endogenous repair pathway locally. These two effectors thus cooperate specifically at the target site to enhance conversion efficacy. To avoid crosstalk between the CRC recruitment site and the inhibitor recruitment site, orthogonal recruiting RNA motifs can be used for each of these modules (e.g. MS2-MCP recruits CRC effector AID fused to MCP and PP7-PCP recruits UGI fused to PCP) (FIG. 10C).

Figure 10D:
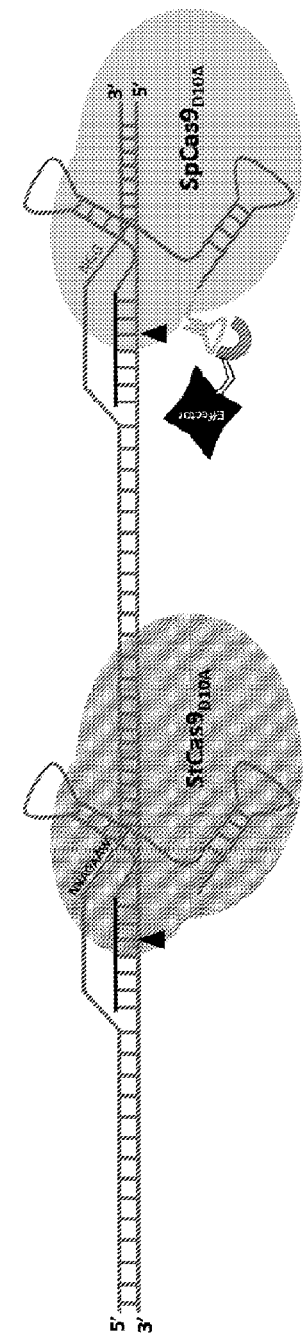

In some embodiments, the hetero-recruitment configuration can also be applied if heterodimerization is required for proper effector activity. The hetero-recruitment configuration can also be applied to any gene conversion enzyme system requiring at least two components to function effectively. A non-exhaustive list of recruiting RNA scaffolds and their RNA binding protein partners is summarized in Table 2. Finally, if there are PAM sequence restrictions for cis double nicking, it is also possible to program Cas9 orthologs from species other than *S. pyogenes*, depending on what PAM sequences are available near the targeting sites (FIG. 10D). A non-exhaustive list of Cas9 orthologs from different species is summarized in Table 1.

Utilities and Applications

The systems and methods disclosed herein have a wide variety of utilities including modifying and editing (e.g., inactivating and activating) a target polynucleotide in a multiplicity of cell types. As such the systems and methods have a broad spectrum of applications in, e.g., research and therapy.

Many devastating human diseases have one common cause: genetic alteration or mutation. The disease-causing mutations in patients are either acquired through inheritance from their parents or are caused by environmental factors. These diseases include, but are not limited to, the following categories. First, some genetic disorders are caused by germline mutations. One example is cystic fibrosis, which is caused by mutations at the CFTR gene inherited from parents. A second suppressor mutation in the mutant CFTR can partially restore the function of CFTR protein in somatic tissues. Other example genetic diseases caused by a point genetic mutation that can be corrected by our technology include Gaucher's disease, alpha trypsin deficiency disease, sickle cell anemia, to name a few. Second, some diseases, such as chronic viral infectious diseases, are caused by exogenous environmental factors and resulting genetic alterations. One example is AIDS, which is caused by insertion of the human HIV viral genome into the genome of infected T-cells. Third, some neurodegenerative diseases involve genetic alterations. One example is Huntington's diseases, which is cause by expansion of CAG tri-nucleotide in the huntingtin gene of affected patients. Finally, cancers are caused by various somatic mutations accumulated in cancer cells. Therefore, correcting the disease-causing genetic mutations, or functionally correcting the sequence, provides an appealing therapeutic opportunity to treat these diseases.

Somatic genetic editing is an appealing therapeutic strategy for many human diseases. To achieve successful therapeutic genetic editing, three critical factors are considered essential: (i) how to achieve sequence specific recognition ("sequence recognition module"); (ii) how to correct the underlying mutations ("correction module"); and (iii) how to link the "correction module" to "sequence recognition module" together to achieve sequence specific correction. There are number of ways of achieving each individual task. However, none of the currently existing platforms or technologies could achieve optimal and practical somatic genetic editing. More specifically, current gene specific editing technologies are mostly based on nucleases induced DNA DSB and consequent DSB induced homologous recombination, the activity of which is low or absent in most somatic cells. Thus, those technologies are of limited use for therapeutic corrections of pathological genetic mutations in somatic tissues in most diseases.

In contrast, the system and method disclosed in this invention allow DNA-sequence directed editing of a gene or RNA transcript that does not rely on nuclease activity. The system and method do not generate DSB, or do not rely on the DSB-mediated homologous recombination. Moreover, this design of the system is modular, which allows extremely flexible and convenient way of targeting any desirable DNA or RNA sequences. In essence, this approach enables one to guide a DNA or RNA editing enzyme to virtually any DNA or RNA sequence in somatic cells, including stem cells. Through precise editing the target DNA or RNA sequence, the enzyme can correct the mutated genes in genetic disorders, inactivate the viral genome in the infected cells, eliminate the expression of the disease-causing protein in neurodegenerative diseases, or silence the oncogenic protein in cancers. Accordingly, the system and method disclosed in this invention can be used in correcting underlying genetic alterations in diseases including the above mentioned genetic disorders, chronic infectious diseases, neurodegenerative diseases, and cancer.

Genetic Diseases

It is estimated that over six thousands of genetic diseases are caused by known genetic mutations. Correcting the underlying disease causing mutations in the pathological tissues/organs can provide alleviation or cure to the diseases. For example, cystic fibrosis affects 1 out of every 3,000 people in the US. It is caused by inheritance of a mutated CFTR gene and 70% of the patients have the same mutation, deletion of a tri-nucleotide leading to a deletion of phenylalanine at position 508 (called Δ Phe 508). Δ Phe 508 leads to the mislocation and degradation of CFTR. The system and method disclosed in this invention can be used to convert a Val 509 residue (GTT) to Phe 509 (TTT) in affected tissues (lung), thereby functionally correct the Δ Phe 508 mutation. In addition, a second suppressor mutation (such as R553Q or R553M or V510D) in the mutant Δ Phe 508 CFTR can partially restore the function of CFTR protein in somatic tissues.

Chronic Infectious Diseases

The system and method disclosed in this invention can also be used to specifically inactivate any gene in a viral genome that is incorporated into human cells/tissues. For example, the system and method disclosed in this invention allow one to create a stop codon for early termination of translation of the essential viral genes, and thereby remediate or cure the chronic debilitating infectious diseases. For example, current AIDS therapies can reduce viral load, but cannot totally eliminate dormant HIV from positive T cells. The system and method disclosed herein can be used to permanently inactivate one or two essential HIV gene expression in the integrated HIV genome in human T-cells by introducing one or two stop codons. Another example is hepatitis B virus (HBV). The system and method disclosed here can be used to specifically inactivate one or two essential HBV genes, which are incorporated into human genome, and silence HBV life-cycle.

Neurodegenerative Diseases

Some neurodegenerative diseases are caused by gain-of-function mutations. For example, SOD1G93A leads to development of amyotrophic lateral sclerosis (ALS). The system and method disclosed in this invention can be used to either correct the mutation, or eliminate the mutant protein expression by introducing a stop codon or by changing a splicing site.

Cancers

Many genes (including tumor suppressor genes, oncogenes, and DNA repair genes) contribute to the development of cancer. Mutations in these genes often lead to various cancers. Using the system and method disclosed in this invention, one, can specifically target and correct these mutations. As a result, causative oncogenic proteins can be functionally annulled or their expression can be eliminated by introducing a point mutation at either the catalytic sites or splicing sites.

Stem Cell Genetic Modification

In some embodiments, stem cell or progenitor cell can be genetically modified using the system and method disclosed in this invention. Suitable cells include, e.g., stem cells (adult stem cells, embryonic stem cells, iPS cells, etc.) and progenitor cells (e.g., cardiac progenitor cells, neural progenitor cells, etc.). Suitable cells include mammalian stem cells and progenitor cells, including, e.g., rodent stem cells, rodent progenitor cells, human stem cells, human progenitor cells, etc. Suitable host cells include in vitro host cells, e.g., isolated host cells.

In some embodiments, the present invention can be used for targeted and precise genetic modification of tissue ex vivo, correcting the underlying genetic defects. After the ex vivo correction, the tissues could be returned to the patients. Moreover, the technology can be broadly used in cell-based therapies for correcting genetic diseases.

Genetic Editing in Animals and Plants

The system and method described above can be used to generate a transgenic non-human animal or plant having one or more genetic modification of interest. In some embodiments, the transgenic non-human animal is homozygous for the genetic modification. In some embodiments, the transgenic non-human animal is heterozygous for the genetic modification. In some embodiments, the transgenic non-human animal is a vertebrate, for example, a fish (e.g., zebra fish, gold fish, puffer fish, cave fish, etc.), an amphibian (frog, salamander, etc.), a bird (e.g., chicken, turkey, etc.), a reptile (e.g., snake, lizard, etc.), a mammal (e.g., an ungulate, e.g., a pig, a cow, a goat, a sheep, etc.; a lagomorph (e.g., a rabbit); a rodent (e.g., a rat, a mouse); a non-human primate.

The invention can be used for treating diseases in animals in a way similar to those for treating diseases in humans as described above. Alternatively, it can be used to generate knock-in animal disease models bearing specific genetic mutation for purposes of research, drug discovery, and target validation. The system and method described above can also be used for introduction of point mutations to ES cells or embryos of various organisms, for purpose of breeding and improving animal stocks and crop quality.

Methods of introducing exogenous nucleic acids into plant cells are well known in the art. Suitable methods include viral infection (such as double stranded DNA viruses), transfection, conjugation, protoplast fusion, electroporation, particle gun technology, calcium phosphate precipitation, direct microinjection, silicon carbide whiskers technology, Agrobacterium-mediated transformation and the like. The choice of method is generally dependent on the type of cell being transformed and the circumstances under which the transformation is taking place (i.e. in vitro, ex vivo, or in vivo).

Kit

This invention further provides kits containing reagents for performing the above-described methods, including CRISPR:Cas guided target binding or correction reaction. To that end, one or more of the reaction components, e.g., RNAs, Cas proteins, fusion effector proteins and related nucleic acids, for the methods disclosed herein can be supplied in the form of a kit for use. In one embodiment, the kit comprises a CRISPR protein or a nucleic acid encoding the Cas protein, effector protein, one or more of a RNA scaffold described above, a set of RNA molecules described above. In others embodiments, the kit can include one or more other reaction components. In such a kit, an appropriate amount of one or more reaction components is provided in one or more containers or held on a substrate.

Examples of additional components of the kits include, but are not limited to, one or more host cells, one or more reagents for introducing foreign nucleotide sequences into host cells, one or more reagents (e.g., probes or PCR primers) for detecting expression of the RNA or protein or verifying the target nucleic acid's status, and buffers or culture media for the reactions (in 1X or concentrated forms). The kit may also include one or more of the following components: supports, terminating, modifying or digestion reagents, osmolytes, and an apparatus for detection.

The reaction components used can be provided in a variety of forms. For example, the components (e.g., enzymes, RNAs, probes and/or primers) can be suspended in an aqueous solution or as a freeze-dried or lyophilized powder, pellet, or bead. In the latter case, the components, when reconstituted, form a complete mixture of components for use in an assay. The kits of the invention can be provided at any suitable temperature. For example, for storage of kits containing protein components or complexes thereof in a liquid, it is preferred that they are provided and maintained below 0° C., preferably at or below −20° C., or otherwise in a frozen state.

A kit or system may contain, in an amount sufficient for at least one assay, any combination of the components described herein. In some applications, one or more reaction components may be provided in pre-measured single use amounts in individual, typically disposable, tubes or equivalent containers. With such an arrangement, a RNA-guided reaction can be performed by adding a target nucleic acid, or a sample or cell containing the target nucleic acid, to the individual tubes directly. The amount of a component supplied in the kit can be any appropriate amount and may depend on the target market to which the product is directed. The container(s) in which the components are supplied can be any conventional container that is capable of holding the supplied form, for instance, microfuge tubes, microtiter plates, ampoules, bottles, or integral testing devices, such as fluidic devices, cartridges, lateral flow, or other similar devices.

The kits can also include packaging materials for holding the container or combination of containers. Typical packaging materials for such kits and systems include solid matrices (e.g., glass, plastic, paper, foil, micro-particles and the like) that hold the reaction components or detection probes in any of a variety of configurations (e.g., in a vial, microtiter plate well, microarray, and the like). The kits may further include instructions recorded in a tangible form for use of the components.

Definition

A nucleic acid or polynucleotide refers to a DNA molecule (for example, but not limited to, a cDNA or genomic DNA) or an RNA molecule (for example, but not limited to, an mRNA), and includes DNA or RNA analogs. A DNA or RNA analog can be synthesized from nucleotide analogs. The DNA or RNA molecules may include portions that are not naturally occurring, such as modified bases, modified backbone, deoxyribonucleotides in an RNA, etc. The nucleic acid molecule can be single-stranded or double-stranded.

The term "isolated" when referring to nucleic acid molecules or polypeptides means that the nucleic acid molecule or the polypeptide is substantially free from at least one other component with which it is associated or found together in nature.

As used herein, the term "guide RNA" generally refers to an RNA molecule (or a group of RNA molecules collectively) that can bind to a CRISPR protein and target the CRISPR protein to a specific location within a target DNA. A guide RNA can comprise two segments: a DNA-targeting guide segment and a protein-binding segment. The DNA-targeting segment comprises a nucleotide sequence that is complementary to (or at least can hybridize to under stringent conditions) a target sequence. The protein-binding segment interacts with a CRISPR protein, such as a Cas9 or Cas9 related polypeptide. These two segments can be located in the same RNA molecule or in two or more separate RNA molecules. When the two segments are in separate RNA molecules, the molecule comprising the DNA-targeting guide segment is sometimes referred to as the CRISPR RNA (crRNA), while the molecule comprising the protein-binding segment is referred to as the trans-activating RNA (tracrRNA).

As used herein, the term "target nucleic acid" or "target" refers to a nucleic acid containing a target nucleic acid sequence. A target nucleic acid may be single-stranded or double-stranded, and often is double-stranded DNA. A "target nucleic acid sequence," "target sequence" or "target region," as used herein, means a specific sequence or the complement thereof that one wishes to bind to or modify using a CRISPR system. A target sequence may be within a nucleic acid in vitro or in vivo within the genome of a cell, which may be any form of single-stranded or double-stranded nucleic acid.

A "target nucleic acid strand" refers to a strand of a target nucleic acid that is subject to base-pairing with a guide RNA as disclosed herein. That is, the strand of a target nucleic acid that hybridizes with the crRNA and guide sequence is referred to as the "target nucleic acid strand." The other strand of the target nucleic acid, which is not complementary to the guide sequence, is referred to as the "non-complementary strand." In the case of double-stranded target nucleic acid (e.g., DNA), each strand can be a "target nucleic acid strand" to design crRNA and guide RNAs and used to practice the method of this invention as long as there is a suitable PAM site.

As used herein, the term "derived from" refers to a process whereby a first component (e.g., a first molecule), or information from that first component, is used to isolate, derive or make a different second component (e.g., a second molecule that is different from the first). For example, the mammalian codon-optimized Cas9 polynucleotides are derived from the wild type Cas9 protein amino acid sequence. Also, the variant mammalian codon-optimized Cas9 polynucleotides, including the Cas9 single mutant nickase (nCas9, such as nCas9D10A) and Cas9 double mutant null-nuclease (dCas9, such as dCas9 D10A H840A), are derived from the polynucleotide encoding the wild type mammalian codon-optimized Cas9 protein.

As used herein the term "wild type" is a term of the art understood by skilled persons and means the typical form of an organism, strain, gene or characteristic as it occurs in nature as distinguished from mutant or variant forms.

As used herein, the term "variant" refers to a first composition (e.g., a first molecule), that is related to a second composition (e.g., a second molecule, also termed a "parent" molecule). The variant molecule can be derived from, isolated from, based on or homologous to the parent molecule. For example, the mutant forms of mammalian codon-optimized Cas9 (hspCas9), including the Cas9 single mutant nickase and the Cas9 double mutant null-nuclease, are variants of the mammalian codon-optimized wild type Cas9 (hspCas9). The term variant can be used to describe either polynucleotides or polypeptides.

As applied to polynucleotides, a variant molecule can have entire nucleotide sequence identity with the original parent molecule, or alternatively, can have less than 100% nucleotide sequence identity with the parent molecule. For example, a variant of a gene nucleotide sequence can be a second nucleotide sequence that is at least 50%, 60%, 70%, 80%, 90%, 95%, 98%, 99% or more identical in nucleotide sequence compare to the original nucleotide sequence. Polynucleotide variants also include polynucleotides comprising the entire parent polynucleotide, and further comprising additional fused nucleotide sequences. Polynucleotide variants also includes polynucleotides that are portions or subsequences of the parent polynucleotide, for example, unique subsequences (e.g., as determined by standard sequence comparison and alignment techniques) of the polynucleotides disclosed herein are also encompassed by the invention.

In another aspect, polynucleotide variants include nucleotide sequences that contain minor, trivial or inconsequential changes to the parent nucleotide sequence. For example, minor, trivial or inconsequential changes include changes to nucleotide sequence that (i) do not change the amino acid sequence of the corresponding polypeptide, (ii) occur outside the protein-coding open reading frame of a polynucleotide, (iii) result in deletions or insertions that may impact the corresponding amino acid sequence, but have little or no impact on the biological activity of the polypeptide, (iv) the nucleotide changes result in the substitution of an amino acid with a chemically similar amino acid. In the case where a polynucleotide does not encode for a protein (for example, a tRNA or a crRNA or a tracrRNA), variants of that polynucleotide can include nucleotide changes that do not result in loss of function of the polynucleotide. In another aspect, conservative variants of the disclosed nucleotide sequences that yield functionally identical nucleotide sequences are encompassed by the invention. One of skill will appreciate that many variants of the disclosed nucleotide sequences are encompassed by the invention.

As applied to proteins, a variant polypeptide can have entire amino acid sequence identity with the original parent polypeptide, or alternatively, can have less than 100% amino acid identity with the parent protein. For example, a variant of an amino acid sequence can be a second amino acid sequence that is at least 50%, 60%, 70%, 80%, 90%, 95%, 98%, 99% or more identical in amino acid sequence compared to the original amino acid sequence.

Polypeptide variants include polypeptides comprising the entire parent polypeptide, and further comprising additional fused amino acid sequences. Polypeptide variants also includes polypeptides that are portions or subsequences of the parent polypeptide, for example, unique subsequences (e.g., as determined by standard sequence comparison and alignment techniques) of the polypeptides disclosed herein are also encompassed by the invention.

In another aspect, polypeptide variants include polypeptides that contain minor, trivial or inconsequential changes to the parent amino acid sequence. For example, minor, trivial or inconsequential changes include amino acid changes (including substitutions, deletions and insertions) that have little or no impact on the biological activity of the polypeptide, and yield functionally identical polypeptides, including additions of non-functional peptide sequence. In other aspects, the variant polypeptides of the invention change the biological activity of the parent molecule, for example, mutant variants of the Cas9 polypeptide that have modified or lost nuclease activity. One of skill will appreciate that many variants of the disclosed polypeptides are encompassed by the invention.

In some aspects, polynucleotide or polypeptide variants of the invention can include variant molecules that alter, add or delete a small percentage of the nucleotide or amino acid positions, for example, typically less than about 10%, less than about 5%, less than 4%, less than 2% or less than 1%.

As used herein, the term "conservative substitutions" in a nucleotide or amino acid sequence refers to changes in the nucleotide sequence that either (i) do not result in any corresponding change in the amino acid sequence due to the redundancy of the triplet codon code, or (ii) result in a substitution of the original parent amino acid with an amino acid having a chemically similar structure. Conservative substitution tables providing functionally similar amino acids are well known in the art, where one amino acid residue is substituted for another amino acid residue having similar chemical properties (e.g., aromatic side chains or positively charged side chains), and therefore does not substantially change the functional properties of the resulting polypeptide molecule.

The following are groupings of natural amino acids that contain similar chemical properties, where a substitution within a group is a "conservative" amino acid substitution. This grouping indicated below is not rigid, as these natural amino acids can be placed in different grouping when different functional properties are considered. Amino acids having nonpolar and/or aliphatic side chains include: glycine, alanine, valine, leucine, isoleucine and proline. Amino acids having polar, uncharged side chains include: serine, threonine, cysteine, methionine, asparagine and glutamine. Amino acids having aromatic side chains include: phenylalanine, tyrosine and tryptophan. Amino acids having positively charged side chains include: lysine, arginine and histidine. Amino acids having negatively charged side chains include: aspartate and glutamate.

A "Cas9 mutant" or "Cas9 variant" refers to a protein or polypeptide derivative of the wild type Cas9 protein such as S. pyogenes Cas9 protein (i.e., SEQ ID NO: 1), e.g., a protein having one or more point mutations, insertions, deletions, truncations, a fusion protein, or a combination thereof. It retains substantially the RNA targeting activity of the Cas9 protein. The protein or polypeptide can comprise, consist of, or consist essentially of a fragment of SEQ ID NO: 1. In general, the mutant/variant is at least 50% (e.g., any number between 50% and 100%, inclusive) identical to SEQ ID NO: 1. The mutant/variant can bind to an RNA molecule and be targeted to a specific DNA sequence via the RNA molecule, and may additional have a nuclease activity. Examples of these domains include RuvC like motifs (aa. 7-22, 759-766 and 982-989 in SEQ ID NO: 1) and HNH motif (aa 837-863). See Gasiunas et al., Proc Natl Acad Sci USA. 2012 September 25; 109(39): E2579-E2586 and WO2013176772.

"Complementarity" refers to the ability of a nucleic acid to form hydrogen bond(s) with another nucleic acid sequence by either traditional Watson-Crick base-pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques in Biochemistry and Molecular Biology-Hybridization with Nucleic Acid Probes Part I, Second Chapter "Overview of principles of hybridization and the strategy of nucleic acid probe assay", Elsevier, N.Y.

"Hybridization" or "hybridizing" refers to a process where completely or partially complementary nucleic acid strands come together under specified hybridization conditions to form a double-stranded structure or region in which the two constituent strands are joined by hydrogen bonds. Although hydrogen bonds typically form between adenine and thymine or uracil (A and T or U) or cytidine and guanine (C and G), other base pairs may form (e.g., Adams et al., The Biochemistry of the Nucleic Acids, 11th ed., 1992).

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, pegylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

The term "fusion polypeptide" or "fusion protein" means a protein created by joining two or more polypeptide sequences together. The fusion polypeptides encompassed in this invention include translation products of a chimeric gene construct that joins the nucleic acid sequences encoding a first polypeptide, e.g., an RNA-binding domain, with the nucleic acid sequence encoding a second polypeptide, e.g., an effector domain, to form a single open-reading frame. In other words, a "fusion polypeptide" or "fusion protein" is a recombinant protein of two or more proteins which are joined by a peptide bond or via several peptides. The fusion protein may also comprise a peptide linker between the two domains.

The term "linker" refers to any means, entity or moiety used to join two or more entities. A linker can be a covalent linker or a non-covalent linker. Examples of covalent linkers include covalent bonds or a linker moiety covalently attached to one or more of the proteins or domains to be linked. The linker can also be a non-covalent bond, e.g., an organometallic bond through a metal center such as platinum atom. For covalent linkages, various functionalities can be used, such as amide groups, including carbonic acid derivatives, ethers, esters, including organic and inorganic esters, amino, urethane, urea and the like. To provide for linking, the domains can be modified by oxidation, hydroxylation, substitution, reduction etc. to provide a site for coupling. Methods for conjugation are well known by persons skilled in the art and are encompassed for use in the present invention. Linker moieties include, but are not limited to, chemical linker moieties, or for example a peptide linker moiety (a linker sequence). It will be appreciated that modification which do not significantly decrease the function of the RNA-binding domain and effector domain are preferred.

As used herein, the term "conjugate" or "conjugation" or "linked" as used herein refers to the attachment of two or more entities to form one entity. A conjugate encompasses both peptide-small molecule conjugates as well as peptide-protein/peptide conjugates.

The terms "subject" and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed. In some embodiments, a subject may be an invertebrate animal, for example, an insect or a nematode; while in others, a subject may be a plant or a fungus.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

As used herein, the term "contacting," when used in reference to any set of components, includes any process whereby the components to be contacted are mixed into same mixture (for example, are added into the same compartment or solution), and does not necessarily require actual physical contact between the recited components. The recited components can be contacted in any order or any combination (or sub-combination), and can include situations where one or some of the recited components are subsequently removed from the mixture, optionally prior to addition of other recited components. For example, "contacting A with B and C" includes any and all of the following situations: (i) A is mixed with C, then B is added to the mixture; (ii) A and B are mixed into a mixture; B is removed from the mixture, and then C is added to the mixture; and (iii) A is added to a mixture of B and C. "Contacting" a target nucleic acid or a cell with one or more reaction components, such as an Cas protein or guide RNA, includes any or all of the following situations: (i) the target or cell is contacted with a first component of a reaction mixture to create a mixture; then other components of the reaction mixture are added in any order or combination to the mixture; and (ii) the reaction mixture is fully formed prior to mixture with the target or cell.

The term "mixture" as used herein, refers to a combination of elements, that are interspersed and not in any particular order. A mixture is heterogeneous and not spatially separable into its different constituents. Examples of mixtures of elements include a number of different elements that are dissolved in the same aqueous solution, or a number of different elements attached to a solid support at random or in no particular order in which the different elements are not spatially distinct. In other words, a mixture is not addressable.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention. The term "about" generally refers to plus or minus 10% of the indicated number. For example, "about 10%" may indicate a range of 9% to 11%, and "about 20" may mean from 18-22. Other meanings of "about" may be apparent from the context, such as rounding off, so, for example "about 1" may also mean from 0.5 to 1.4.

EXAMPLES

Example 1 CRC System Led to Site-Specific Mutation at Target Cytidine Nucleotides in Bacterial Genome In this example, *E. coli* MG1655 strain was used as model. Mutations in bacterial RNA polymerase subunit β gene (rpoB) render cells resistant to the antibiotic rifampicin (Jin, et al., *Journal of Molecular Biology* 202, 45-58, (1988), and Goldstein, et al., *J Antibiot* 67, 625-630, doi:10.1038/ja.2014.107 (2014)). Mutants can be isolated and analyzed individually, and mutation frequency can be calculated. AID is a B-cell specific protein that belongs to APOBEC family of cytidine deaminases and is involved in somatic hypermutation and class switch recombination during antibody diversification and affinity maturation (Odegard, et al., *Nat Rev Immunol* 6, 573-583 (2006), and Noia, et al. *Annual Review of Biochemistry* 76, 1-22, doi:doi:10.1146/annurev.biochem.76.061705.090740 (2007)). Thus, for these set of experiments, rpoB gene from *E. coli* MG1655 is targeted using AID as a non-nuclease effector protein.

Constructs and System Configurations

Inducible Promoters

All protein-coding constructs were designed under the control of a Tet inducible promoter. Anhydrotetracycline (ATc; Sigma) was used as inducer at a concentration of 30 nM.

Cas9 Constructs

A central feature of the present system is the introduction of precise nucleotide modifications without generating DSBs. To this end, nuclease deficient versions of Cas9 were used as DNA targeting modules, namely catalytically deficient Cas9 (Cas9$_{D10A/H840A}$, dCas9) and Cas9 nickases (nCas9$_{D10A}$ or nCas9$_{H840A}$) (Jinek, M. et al., *Science* 337, 816-821, doi:10.1126/science.1225829 (2012)). Cas9 nickases have been used to reduce off-target DSB by offset double DNA nicking (Ran, F. A. et al., *Cell* 154, 1380-1389, doi:10.1016/j.cell.2013.08.021 (2013), and Shen, B. et al., *Nat Meth* 11, 399-402, doi:10.1038/nmeth.2857 (2014)) and dCas9 has been engineered to perform a variety of activities independent of nuclease activity. See Fujita, T. et al., *Biochemical and biophysical research communications* 439, 132-136, (2013), Perez-Pinera, P. et al. *Nat Meth* 10, 973-976, doi:10.1038/nmeth.2600 (2013), Mali, P. et al. *Nat Biotechnol* 31, 833-838, doi:10.1038 et al./nbt.2675 (2013), Zalatan, J. G. et al., *Cell* 160, 339-350, doi:10.1016/j.cell.2014.11.052 (2015), Qi, L. S. et al., *Cell* 152, 1173-1183, doi:10.1016/j.cell.2013.02.022 (2013), Larson, M. H. et al., *Nature protocols* 8, 2180-2196, doi:10.1038/nprot.2013.132 (2013), Hilton, I. B. et al., *Nat Biotech* 33, 510-517, doi:10.1038/nbt.3199 (2015), Thakore, P. I. et al., *Nat Meth* 12, 1143-1149, doi:10.1038/nmeth.363 (2015), Chen, B. et al., *Cell* 155, 1479-1491, doi:10.1016/j.cell.2013.12.001 (2013), and Fu, Y. et al., *Nature communications* 7, doi:10.1038/ncomms11707 (2016). Therefore, these variants are largely considered safe and represented perfect candidates to develop the system presented in this study.

Targeted Recruitment System

The system was engineered as an RNA scaffold-mediated recruitment platform. A schematic representation including schematic of constructs used in this study is illustrated in FIG. 1B. Cas9 variants were designed as stand-alone constructs, while gRNAs were engineered as chimeric RNA species in which phage RNA scaffolds are synthetically fused to the 3' end of CRISPR RNA scaffold. Phage RNA scaffolds recruit specific RNA binding proteins that are in turn tethered to non-nuclease effector proteins (FIG. 1C). The RNA scaffold recruiting system is derived from phage MS2 and its interacting partner MS2 coat protein (MCP).

Targeting gRNA

The target is the bacterial rpoB gene. Mutations in three clusters, together called rifampicin resistance-determining region (RRDR), confer the cells resistance to the antibiotic rifampicin (Rif$^R$) (Goldstein, et al., *J Antibiot* 67, 625-630, doi:10.1038/ja.2014.107 (2014)). A set of four gRNAs was designed to target critical amino acids along RRDR Cluster I sequence (i.e. S512, D516, H526 and S531; FIG. 2A). Jin, et al., *Journal of molecular biology* 202, 45-58, (1988) and Jin, D. J. et al., *Methods in Enzymology Vol. Volume* 273 300-319 (Academic Press, 1996)

Experimental Approach

Chemically competent *E. coli* MG1655 cells were transformed with 10-20 ng of total DNA comprised of a combination of plasmids encoding for the constructs described in Section 1. After transformation, cells were selected and induced in Luria-Bertani broth containing the appropriate antibiotics. After selection/induction, OD was measured, cells were serially diluted and 10$^8$ to 10$^4$ cells were plated in LB agar plates containing rifampicin (120 µM). Two hundred cells were plated in selective agar plates without rifampicin for plating efficiency. After overnight incubation, colonies were counted and mutation frequency was scored.

In addition, rpoB gene from isolated colonies was amplified by PCR and sequenced in order to map mutations.

Results

Targeted Recruitment of AID Led to Site-Specific Conversion of C to T.

A set of four gRNAs targeting rpoB's RRDR (cluster I) region was used to recruit AID to target sites (FIG. 2A). CRC targeting with rpoB_TS-4, and to a lesser extend with rpoB_TS-3, increased the survival fraction of MG1655 cells in rifampicin media (FIG. 2B, 2C). Sequence analysis of clones derived from treatment rpoB_TS-4 revealed high specificity, mutating C1592 to T, with the concomitant amino acid change from serine 531 to phenylalanine, a mutation known to render Rif$^R$ cells (Petersen-Mahrt, et al., *Nature* 418, 99-104 (2002), Xu, M., et al., *Journal of Bacteriology* 187, 2783-2792, doi:10.1128/JB.187.8.2783-2792.2005 (2005), and Zenkin, N., et al., *Antimicrobial Agents and Chemotherapy* 49, 1587-1590, doi:10.1128/AAC.49.4.1587-1590.2005 (2005)) (FIG. 2D). The mutation distributions of rpoB_TS-3, rpoB_TS-4 and scramble are summarized in FIG. 2E. The highly increased mutation frequency observed and the location of modified nucleotide on treatment rpoB_TS-4, and with reduced efficiency on treatment rpoB_TS-3, suggest that the target cytidine must be positioned on the unpaired strand left by CRISPR R-loop, preferentially closer to the 5' end of the protospacer (i.e. mutation frequency TS4>TS3, both targeting and modifying the same nucleotide, FIGS. 2A, 2C and 2E). This is consistent with the notion that AID actively deaminates cytidine residues on single strand DNA (Odegard, et al., *Nat Rev Immunol* 6, 573-583 (2006), Noia, et al., *Annual Review of Biochemistry* 76, 1-22, doi:doi:10.1146/annurev.biochem.76.061705.090740 (2007), Smith, H. C., et al., *Seminars in Cell & Developmental Biology* 23, 258-268, doi:10.1016/j.semcdb.2011.10.004 (2012), and Ranganathan, V., et al., *Nature communications* 5, doi:10.1038/ncomms5516 (2014)). A schematic representation of the targeting model is shown FIG. 2F.

CRC Modularity

Figure 3A:
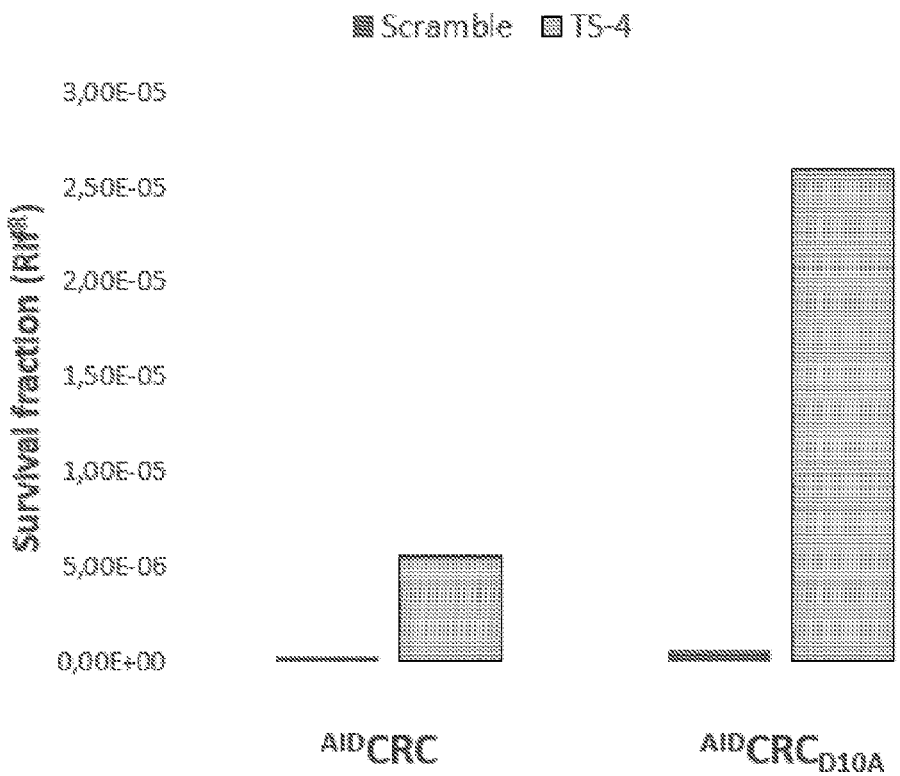
FIGS. 3A and 3B show CRC system modularity: engineering of targeting module increases mutation frequency.
Figure 3B:
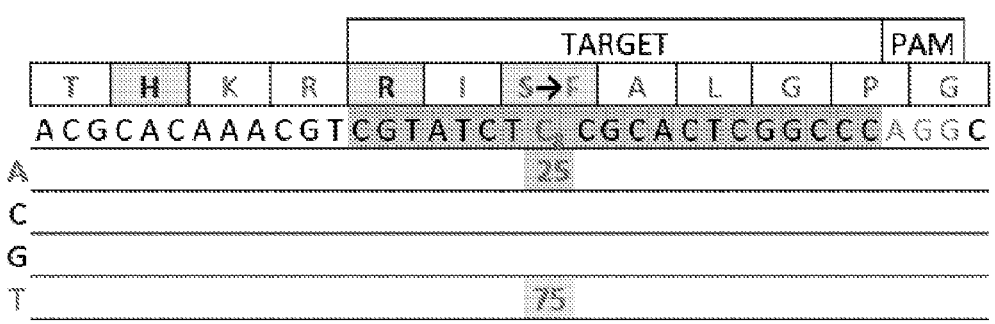

Changing the Targeting Module from dCas9 to nCas9$_{D10A}$ Increases Efficacy of C to T/A Conversion Changing the targeting module from dCas9 to nCas9$_{D10A}$ increased the efficiency of the system in terms of survival fraction on rifampicin plates from 18 to 43 fold over the control (FIG. 3A). Mutation analysis revealed the same specificity as in $^{AID}$CRC treatment for target nucleotide. In this case C1592 was modified in 100% of the clones, 75% mutated C to T and 25% mutated C to A (FIG. 3B).

Figure 4A:
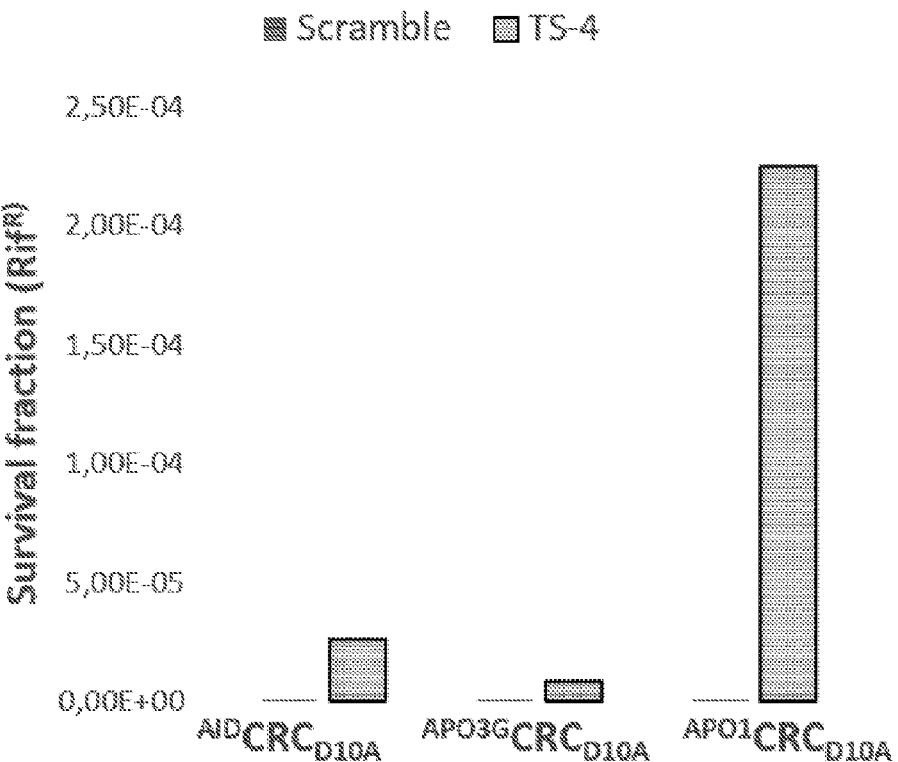
FIGS. 4A and 4B show CRC system modularity: engineering of effector module increases mutation frequency.
Figure 4B:
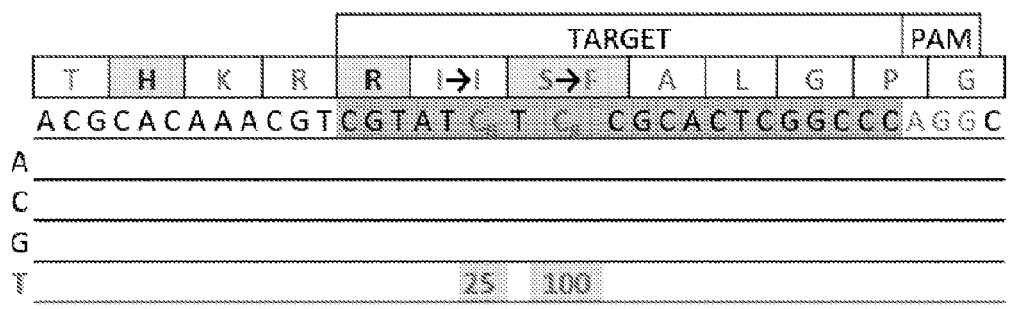

Targeted Recruitment of Other Non-Nuclease Effectors, APOBEC3G and APOBEC1, is Able to Introduce Site-Specific Conversion of C to T/A In addition to AID as effector protein, we tested other cytidine deaminases from the APOBEC family, namely APOBEC3G and APOBEC1 (FIG. 4A). APOBEC1 increased the targeted mutation frequency compared to the prototype system, $^{AID}$CRC$_{D10A}$. APOBEC3G is less active than the prototype system. Mutation analysis of $^{Apo1}$CRC$_{D10A}$ treated cells with rpoB_TS-4 as targeting construct showed 100% C1592>T conversion. In addition, 25% of analyzed clones were double mutants, converting C1590>T, without amino acid change (FIG. 4B).

Increasing the Number of RNA Recruitment Scaffolds Enhances Mutation Frequency Without Altering Specificity of C to T/A Conversion.

Figure 5A:
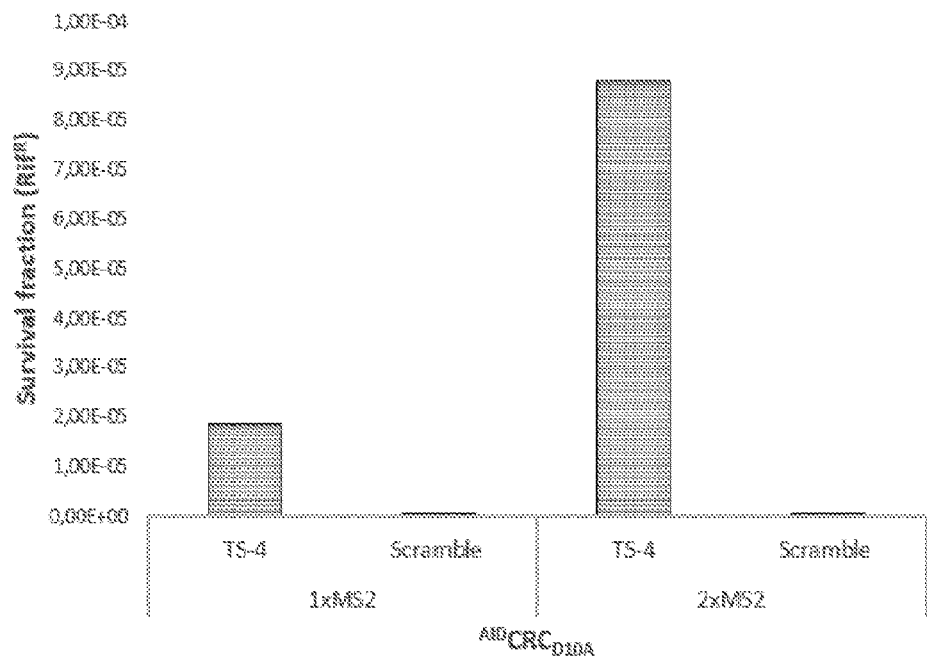
FIGS. 5A and 5B show CRC system modularity: Increasing the number of RNA recruitment scaffolds enhances mutation frequency.
Figure 5B:
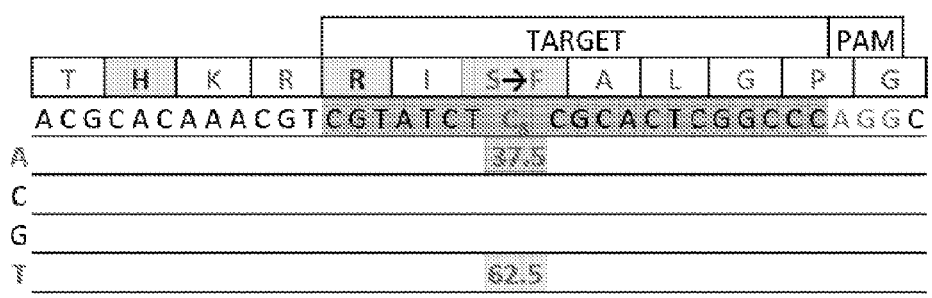

Adding tandem multimeric recruiting scaffolds could potentially increase effector presence on the target region and therefore enhance the system's efficiency. To this end, we engineered rpoB_TS-4 to include two MS2 loops (2×MS2, SEQ ID No: 54). We compared the targeting efficiency between rpoB_TS-4 with one MS2 loop (1×MS2, SEQ ID No: 2) and rpoB_TS-4 2×MS2 (FIG. 5A). The results indicate that increasing the number of recruiting loops in fact enhances the mutation frequency in terms of Rif$^R$, suggesting increased presence of effector protein. Mutation analysis of $^{AID}CRC_{D10A}$ treated cell with rpoB_TS-4_2×MS2 as targeting construct, showed that C1592 nucleotide was modified in 100% of the clones, 62.5% mutated C to T and 37.5% mutated C to A (FIG. 5B). These results suggest that engineering the recruiting modules does not affect the system's targeting specificity Taken together, these results indicate that the modular design of the CRC system facilitates the engineering process and opens the possibility to further improving the system.

Figure 6A:
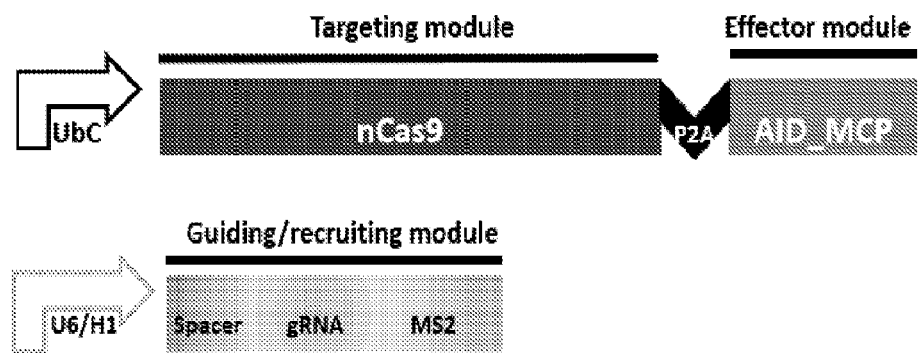
FIGS. 6A, 6B, 6C and 6D show that CRC system is able to modify target nucleotide in extrachromosomal DNA in mammalian cells, restoring protein function.

Example 2 CRC System Led to Site-Specific Nucleotide Conversion in Mammalian Systems Experimental Design: Engineering the System for Mammalian Expression We next sought to engineer the system for mammalian expression. To this end, we recapitulated the prokaryotic AIDCRCD10A system as a multicistronic construct, using a mammalian codon optimized nCas9$_{D10A}$ followed by AID_MCP fusion separated by a self-cleavable P2A peptide. The constructs were cloned under the control of Ubiquitin C promoter. gRNA_2×MS2 cassettes were cloned under the control of U6 or H1 promoter, for targets with 5'-G or 5'-A, respectively (Ranganathan, V., et al., Nature communications 5, doi:10.1038/ncomms5516 (2014)). A schematic representation of the constructs used in these set of experiments is illustrated in FIG. 6A.

Targeting Extrachromosomal DNA: EGFP Reverse Mutation Assay

EGFP was engineered to harbor a loss of function point mutation (197A>G, Y66C) that destroys its fluorophore, therefore rendering the protein non-fluorescent ($_{nf}EGFP^{Y66C}$). The expression vector of the mutant GFP is then transfected into mammalian cells and serves as a substrate of the system. The aim of this experiment was to "correct" this loss-of-function mutation. When the "corrected" gene is transcribed and translated, the correction will restore protein function, which can be visualized as fluorescent cells under the fluorescence microscope.

Experimental Approach

Approximately 7×10$^5$ 293T cells were transfected with 10 μg of a combination of DNA comprising the target plasmid encoding $_{nf}EGFP^{Y66C}$, $^{AID}CRC_{D10A}$ and gRNA constructs. For comparison, base editor 3$^{rd}$ generation system (BE3, Komor, A. C., et al., Nature advance online publication, doi:10.1038/nature17946) was used in these set of experiments. BE3 is a slightly similar system with a different recruitment mechanism, direct fusion of Cas9 with APOBEC1, and includes a peptide that inhibits uracil DNA glycosylase, an enzyme involved in DNA repair. After overnight incubation, cells were analyzed under fluorescence microscope to observe GFP signal.

Results

Figure 6B:
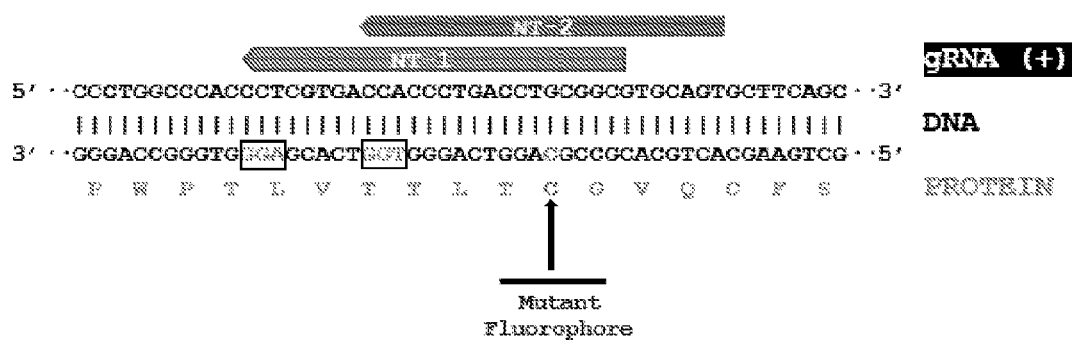
Figure 6C:
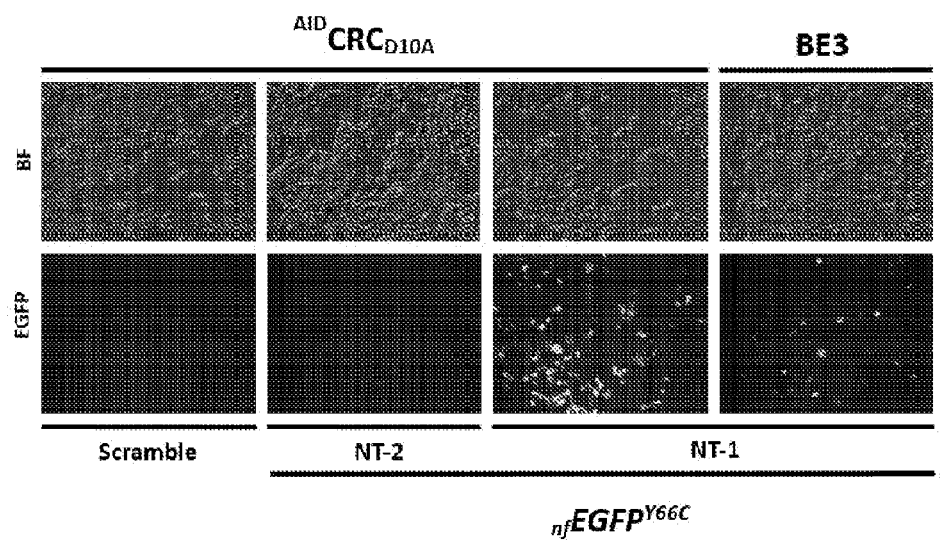
Figure 6D:
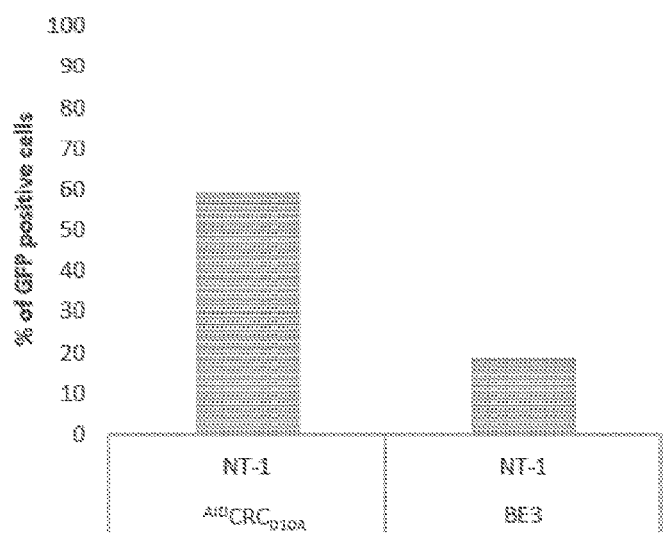

It was found that the above CRC system was able to modify target nucleotide in extrachromosomal DNA, restoring protein function. Since the target cytidine is located on the template strand (TS, −), two gRNAs were designed to bind the non-template strand (NT, +) around the target nucleotide (FIG. 6B). The target cytidine is located on positions 5 and 12 within $_{nf}EGFP^{Y66C}$_NT-1 and $_{nf}EGFP^{Y66C}$_NT-2 protospacers, respectively. 293T cells were transfected with DNA encoding for nCas9$_{D10A}$, AID_MCP, gRNAs ($_{nf}EGFP^{Y66C}$_NT-1 or $_{nf}EGFP^{Y66C}$_NT-2 or scramble), and the target construct, $_{nf}EGFP^{Y66C}$. EGFP signal was detected on cells treated with $_{nf}EGFP^{Y66C}$_NT-1 $_{an}$d $_{nf}EGFP^{Y66C}$_NT-2, but not with scramble (FIG. 6C). EGFP signal was greater in $_{nf}EGFP^{Y66C}$_NT-1 treated cells compared to $_{nf}EGFP^{Y66C}$_NT-2 due to the position of the target cytidine. $_{nf}EGFP^{Y66C}$_NT-1 likely makes the targeted C more accessible to AID (FIG. 6C, central and right panels). In addition, the CRC platform was compared with a different gene editing system (BE3), which utilized a direct fusion of the cytidine deaminase protein to Cas9 protein for recruitment and required a co-expression of an inhibitor of uracil DNA glycosylase (UGI) to improve efficiency. It was unexpectedly found that the CRC system, where the effector and the sequence-targeting module were linked via the RNA scaffold, was much more efficient than the BE3 system, even without local UNG inhibition (without the expression of the uracil DNA glycosylase inhibitor UGI) (FIGS. 6C, 6D, and 7B).

These results confirm the findings from the bacterial system and indicate that the system efficiently deaminates specific cytidine residues in extrachromosomal DNA in human cells in a programmable fashion. Quantitation of GFP positive cells from treatments with $^{AID}CRC_{D10A}$ and BE3 using $_{nf}EGFP^{Y66C}$_NT-1 as a targeting gRNA suggests that CRC system has a better conversion efficiency than BE3 (FIG. 6D).

Example 3 CRC System Led to Site-Specific Nucleotide Conversion in Endogenous Gene in Mammalian Cells Targeting an Endogenous Locus: Chinese Hamster HPRT Gene Encouraged by the positive results observed from the bacterial negative selection system, we decided to use a similar approach in mammalian. Hypoxanthine-guanine phosphoribosyl transferase (HPRT) is an enzyme involved in purine metabolism, and mutations along its coding sequence are known to cause resistance to the antimetabolite 6-thioguanine (6-TG$^R$) (O'Neill, J. P. et al., Nature 269, 815-816 (1977)). For these experiments we aimed to mutate HPRT gene with CRC system in order to disrupt its function followed by selection of mutant cells with 6-TG for further analysis.

Experimental Approach

Approximately 7×10$^5$ Chinese hamster V79-4 cells were transfected with 10 μg of a combination of DNA comprising $^{AID}CRC_{D10A}$ construct and gRNA HPRT_TS-1 expression vector. For comparison, cells were also treated with BE3 and gRNA HPRT_TS-1. Treated and untreated cells were grown following a mammalian mutagenesis protocol previously described (Klein, C. B., et al., in Current Protocols in Toxicology (John Wiley & Sons, Inc., 2001)). Briefly, after transfection cells were maintained for seven days before 6-TG selection for mutation fixation and turnover of preexisting HPRT mRNA and protein. Cells were selected with 60 µM 6-TG for 14 days to allow 6-TG$^R$ colonies to form. Colonies were counted to estimate mutation frequency, and individual colonies were isolated and propagated individually for sequencing analysis.

Results

Figure 7A:
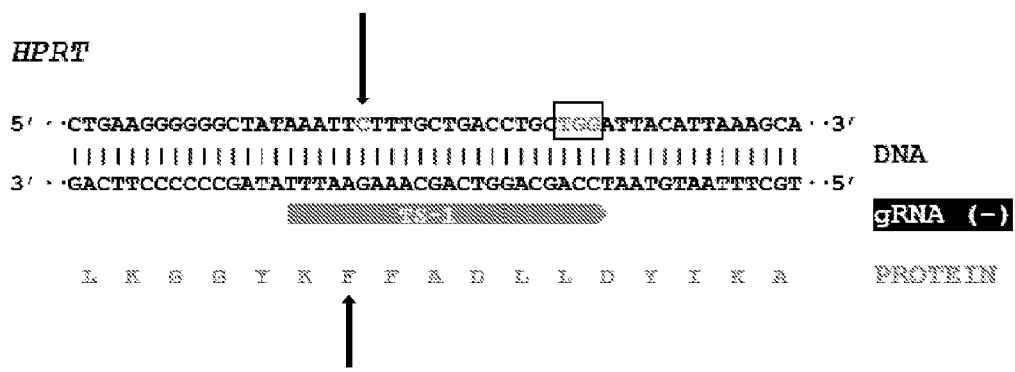
FIGS. 7A and 7B show that treatment CRC system can lead to site-specific nucleotide conversion in endogenous gene in mammalian cells.
Figure 7B:
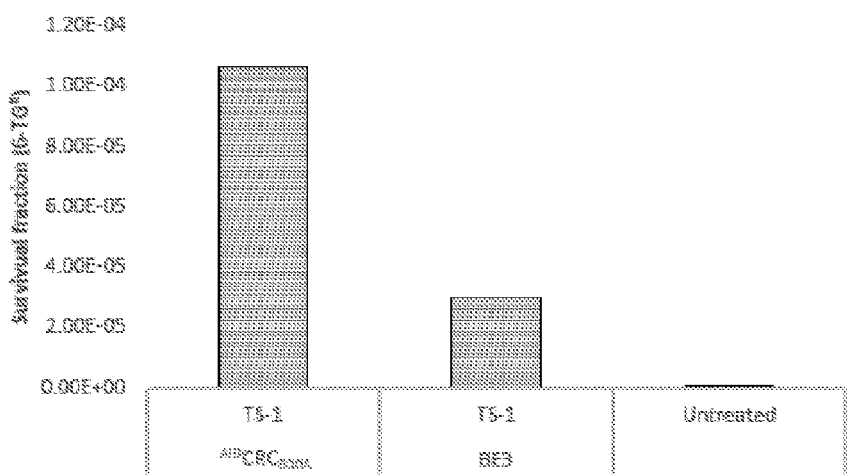

One gRNA was designed to target exon 3 from the Chinese hamster HPRT gene (FIG. 7A). The gRNA targets codon 74 encoding for phenylalanine and mutations in this residue have been implicated in reduced HPRT protein stability (Davidson, B. L., et al., Gene 63, 331-336, (1988)). V79-4 cells were transfected with DNA encoding for $^{AID}CRC_{D10A}$ or BE3 constructs together with the targeting gRNA expression vector. $^{AID}CRC_{D10A}$ system led to mutation rendering the cell resistant to 6-TG treatment with a higher efficiency than BE3 system (i.e. 140- versus 40-fold higher than untreated cells, respectively; FIG. 7B). The results show that the CRC system is able to target and modify specific DNA sequences in an endogenous mammalian locus.

Example 4 Cis Double Nicking Led to Increased Conversion Efficiency on Difficult Targeting Sequence In this example, the above-described cis double nicking was used to enhance conversion efficiency in a bacterial gene conversion model (FIG. 9).

Briefly, nCas9 (nCas9$_{D10A}$ or nCas9$_{H840}$) were programmed to target two neighboring positions on the same DNA strand. Double nicking the same strand with two gRNA does not induce double strand DNA breaks or activation of DSB repair pathways, therefore is a safe approach. A schematic of the procedure is described in FIG. 8. To test this approach, the bacterial gene encoding for the RNA polymerase β subunit (rpoB) was targeted using gRNAs TS-2 and TS-3 (FIG. 9A). This is a negative selection system, in which specific rpoB mutants can be selected using the antibiotic rifampicin since mutants are resistant to this drug (Rif$^R$). The results are shown in FIG. 9B. It was found that in prokaryotic cells targeting efficiency was enhanced by about 130 folds.

Example 5 CRC System Led to Site-Specific Mutation at Target Cytidine Nucleotides In this example, an AID variant was used to reduce AID-induced off-target effects if any. In nature, AID is activated by phosphorylation on Ser38 by the ubiquitous kinase Protein Kinase A (PKA). This phosphorylation leads to interaction with another ubiquitous protein called Replication Protein A (RPA). By mutating Ser38 in AID to Ala (SEQ ID NO: 51) one can reduce the recruitment of AID to off-target sites.

Figure 11A:
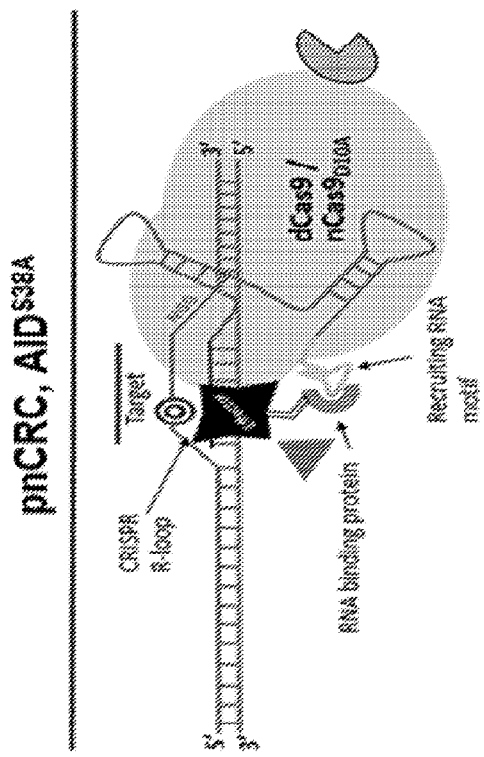
FIGS. 11A and 11B are a schematic of using an AID_S38A variant (a non-phosphorylatable variant) and a result showing no change in conversion efficiency (but potential reduction in off-target effects due to S38A mutation) by this approach.
Figure 11B:
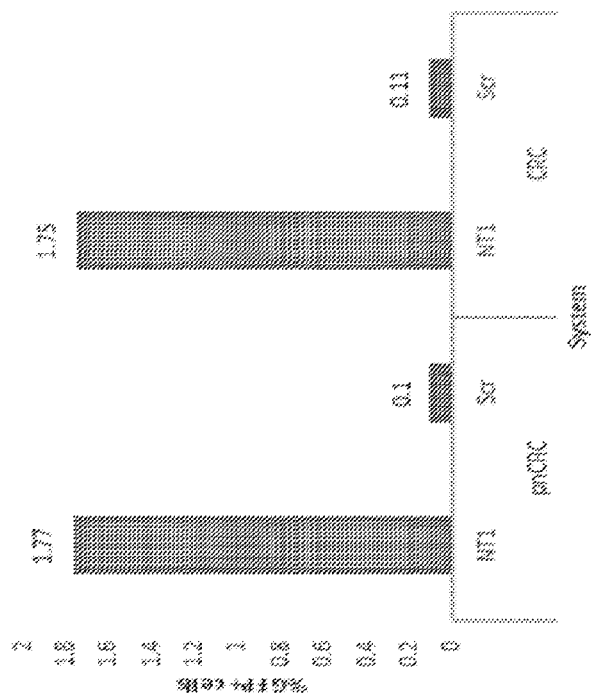

In order to confirm that the mutation in AID does not have an impact on CRC's catalytic activity, HEK293 cells harboring a non-fluorescent EGFP gene stably integrated in the genome were treated in the same way as in previous experiments (GFP reverse mutation assay). The performance of the phosphorylation null CRC (containing AID_S38A variant, called pnCRC) was compared side by side to regular CRC (containing wtAID). The GFP conversion efficiency was measured by flow cytometry. As shown in FIG. 11B, the results indicate that the mutation has no effect in CRC's conversion efficiency.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

What is claimed is:

1. A method of site-specific modification of a target nucleotide in a polynucleotide molecule, comprising interacting a first system and a second system with a first target nucleic acid sequence and a second target nucleic acid sequence in the polynucleotide molecule respectively, wherein the target nucleotide is flanked by the first target nucleic acid sequence and the second target nucleic acid sequence, and wherein
  (1) the first system comprises:
    (i) a first sequence-targeting protein,
    (ii) a first RNA scaffold comprising: (a) a first nucleic acid-targeting motif comprising a first guide RNA sequence that is complementary to the first target nucleic acid sequence, (b) a first protein-binding motif capable of binding to the first sequence-targeting protein, and (c) a first recruiting RNA motif, and
    (iii) a first non-nuclease effector fusion protein, comprising: (a) a first RNA binding domain capable of binding to the first recruiting RNA motif, (b) a first linker, and (c) a first effector domain, wherein the first non-nuclease effector fusion protein has an enzymatic activity; and
  (2) the second system comprises:
    (i) a second sequence-targeting protein and
    (ii) a second RNA scaffold comprising: (a) a second nucleic acid-targeting motif comprising a second guide RNA sequence that is complementary to the second target nucleic acid sequence, and (b) a second protein-binding motif capable of binding to the second sequence-targeting protein,
    wherein the first sequence-targeting protein and the second sequence-targeting protein are nicking proteins, and
    wherein the second system does not comprise an effector fusion protein.

2. The method of claim 1, wherein the second RNA scaffold does not comprise a recruiting RNA motif.

3. The method of claim 2, wherein the first system is located at position 3' relative to the second system.

4. The method of claim 1, wherein the first system is located at position 5' relative to the second system.

5. The method of claim 1, wherein the first recruiting RNA motif and the first RNA binding domain are a pair selected from the group consisting of:
  a telomerase Ku binding motif and Ku protein or a RNA-binding section thereof,
  a telomerase Sm7 binding motif and Sm7 protein or a RNA-binding section thereof,
  a MS2 phage operator stem-loop and MS2 coat protein (MCP) or a RNA-binding section thereof,
  a PP7 phage operator stem-loop and PP7 coat protein (PCP) or a RNA-binding section thereof,
  a SfMu phage Com stem-loop and Com RNA binding protein or a RNA-binding section thereof, and
  a non-natural RNA aptamer and corresponding aptamer ligand or a RNA-binding section thereof.

6. The method of claim 1, wherein the first linker is 0 to 100 amino acid residues in length.

7. The method of claim 1, wherein the enzymatic activity is deamination activity, methyltransferase activity, demethylase activity, DNA repair activity, DNA damage activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity.

8. The method of claim 7, wherein the enzymatic activity is deamination activity, methyltransferase activity, or demethylase activity.

9. The method of claim 7, wherein the enzymatic activity is a cytidine deamination activity or adenosine deamination activity.

10. The method of claim 1, wherein the polynucleotide molecule is in a cell.

11. The method of claim 10, wherein the cell is in or derived from a human or non-human subject.

12. The method of claim 11, wherein the human or non-human subject has a genetic mutation of a gene.

13. The method of claim 12, wherein the subject has a disorder caused by the genetic mutation or is at risk of having the disorder.

14. The method of claim 12, wherein said site-specific modification corrects the genetic mutation or inactivates the expression of the gene.

15. The method of claim 11, wherein the subject has a pathogen or is at risk of being exposed to the pathogen.

16. The method of claim 15, wherein said site-specific modification inactivates a gene of the pathogen.

17. An isolated nucleic acid or a set of isolated nucleic acids encoding the first system and the second system in claim 1.

18. An expression vector or an isolated host cell comprising the nucleic acid or the set of isolated nucleic acids of claim 17.

19. A kit or composition comprising one or more selected from the group consisting of
- the first system and the second system in claim 1,
- an isolated nucleic acid or a set of isolated nucleic acids encoding the first system and the second system,
- an expression vector comprising the isolated nucleic acid or the set of isolated nucleic acids, and
- an isolated host cell comprising the nucleic acid or the set of isolated nucleic acids.

20. The kit of claim 19 further comprising one or more components selected from the group consisting of a reagent for reconstitution and/or dilution and a reagent for introducing nucleic acid or polypeptides into a host cell.

* * * * *

SEQUENCE LISTING

<160> NUMBER OF SEQ ID NOS: 54

<210> SEQ ID NO 1
<211> LENGTH: 1368
<212> TYPE: PRT
<213> ORGANISM: Streptococcus pyogenes

<400> SEQUENCE: 1

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110
```

-continued

```
His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
    515                 520                 525
```

```
Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                    565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Arg Tyr
                    645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                    725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                    805                 810                 815

Gln Asn Gly Arg Asp Met Tyr Val Asp Gln Glu Leu Asp Ile Asn Arg
                820                 825                 830

Leu Ser Asp Tyr Asp Val Asp Ala Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                    885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
```

-continued

```
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                        980                 985                 990
Val Gly Thr Ala Leu Ile Lys Lys Tyr Pro Lys Leu Glu Ser Glu Phe
                    995                 1000                1005
Val Tyr Gly Asp Tyr Lys Val Tyr Asp Val Arg Lys Met Ile Ala
    1010                1015                1020
Lys Ser Glu Gln Glu Ile Gly Lys Ala Thr Ala Lys Tyr Phe Phe
    1025                1030                1035
Tyr Ser Asn Ile Met Asn Phe Phe Lys Thr Glu Ile Thr Leu Ala
    1040                1045                1050
Asn Gly Glu Ile Arg Lys Arg Pro Leu Ile Glu Thr Asn Gly Glu
    1055                1060                1065
Thr Gly Glu Ile Val Trp Asp Lys Gly Arg Asp Phe Ala Thr Val
    1070                1075                1080
Arg Lys Val Leu Ser Met Pro Gln Val Asn Ile Val Lys Lys Thr
    1085                1090                1095
Glu Val Gln Thr Gly Gly Phe Ser Lys Glu Ser Ile Leu Pro Lys
    1100                1105                1110
Arg Asn Ser Asp Lys Leu Ile Ala Arg Lys Lys Asp Trp Asp Pro
    1115                1120                1125
Lys Lys Tyr Gly Gly Phe Asp Ser Pro Thr Val Ala Tyr Ser Val
    1130                1135                1140
Leu Val Val Ala Lys Val Glu Lys Gly Lys Ser Lys Lys Leu Lys
    1145                1150                1155
Ser Val Lys Glu Leu Leu Gly Ile Thr Ile Met Glu Arg Ser Ser
    1160                1165                1170
Phe Glu Lys Asn Pro Ile Asp Phe Leu Glu Ala Lys Gly Tyr Lys
    1175                1180                1185
Glu Val Lys Lys Asp Leu Ile Ile Lys Leu Pro Lys Tyr Ser Leu
    1190                1195                1200
Phe Glu Leu Glu Asn Gly Arg Lys Arg Met Leu Ala Ser Ala Gly
    1205                1210                1215
Glu Leu Gln Lys Gly Asn Glu Leu Ala Leu Pro Ser Lys Tyr Val
    1220                1225                1230
Asn Phe Leu Tyr Leu Ala Ser His Tyr Glu Lys Leu Lys Gly Ser
    1235                1240                1245
Pro Glu Asp Asn Glu Gln Lys Gln Leu Phe Val Glu Gln His Lys
    1250                1255                1260
His Tyr Leu Asp Glu Ile Ile Glu Gln Ile Ser Glu Phe Ser Lys
    1265                1270                1275
Arg Val Ile Leu Ala Asp Ala Asn Leu Asp Lys Val Leu Ser Ala
    1280                1285                1290
Tyr Asn Lys His Arg Asp Lys Pro Ile Arg Glu Gln Ala Glu Asn
    1295                1300                1305
Ile Ile His Leu Phe Thr Leu Thr Asn Leu Gly Ala Pro Ala Ala
    1310                1315                1320
Phe Lys Tyr Phe Asp Thr Thr Ile Asp Arg Lys Arg Tyr Thr Ser
    1325                1330                1335
Thr Lys Glu Val Leu Asp Ala Thr Leu Ile His Gln Ser Ile Thr
    1340                1345                1350
```

Gly Leu Tyr Glu Thr Arg Ile Asp Leu Ser Gln Leu Gly Gly Asp
      1355                1360                1365

<210> SEQ ID NO 2
<211> LENGTH: 129
<212> TYPE: DNA
<213> ORGANISM: Artificial Sequence
<220> FEATURE:
<223> OTHER INFORMATION: RNA scaffold expression cassette
<220> FEATURE:
<221> NAME/KEY: misc_feature
<222> LOCATION: (1)..(20)
<223> OTHER INFORMATION: n is a, c, g, or t

<400> SEQUENCE: 2
nnnnnnnnnn nnnnnnnnnn gttttagagc tagaaatagc aagttaaaat aaggctagtc      60
cgttatcaac ttgaaaaagt ggcaccgagt cggtgcgcgc acatgaggat cacccatgtg     120
cttttttg                                                              129

<210> SEQ ID NO 3
<211> LENGTH: 340
<212> TYPE: PRT
<213> ORGANISM: Artificial Sequence
<220> FEATURE:
<223> OTHER INFORMATION: Effector AID -MCP fusion

<400> SEQUENCE: 3

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu Glu Leu Lys Thr Pro Leu Gly Asp Thr Thr
        195                 200                 205

His Thr Ser Pro Pro Cys Pro Ala Pro Glu Leu Leu Gly Gly Pro Met
    210                 215                 220

Ala Ser Asn Phe Thr Gln Phe Val Leu Val Asp Asn Gly Gly Thr Gly
225                 230                 235                 240

```
Asp Val Thr Val Ala Pro Ser Asn Phe Ala Asn Gly Ile Ala Glu Trp
                245                 250                 255

Ile Ser Ser Asn Ser Arg Ser Gln Ala Tyr Lys Val Thr Cys Ser Val
            260                 265                 270

Arg Gln Ser Ser Ala Gln Asn Arg Lys Tyr Thr Ile Lys Val Glu Val
        275                 280                 285

Pro Lys Gly Ala Trp Arg Ser Tyr Leu Asn Met Glu Leu Thr Ile Pro
    290                 295                 300

Ile Phe Ala Thr Asn Ser Asp Cys Glu Leu Ile Val Lys Ala Met Gln
305                 310                 315                 320

Gly Leu Leu Lys Asp Gly Asn Pro Ile Pro Ser Ala Ile Ala Ala Asn
                325                 330                 335

Ser Gly Ile Tyr
            340

<210> SEQ ID NO 4
<211> LENGTH: 93
<212> TYPE: RNA
<213> ORGANISM: Artificial Sequence
<220> FEATURE:
<223> OTHER INFORMATION: hybrid crRNA:tracRNA

<400> SEQUENCE: 4
guuuaagagc uaugcuggaa acagcauagc aaguuuaaau aaggcuaguc cguuaucaac       60
uugaaaaagu ggcaccgagu cggugcuuuu uuu                                   93

<210> SEQ ID NO 5
<211> LENGTH: 79
<212> TYPE: RNA
<213> ORGANISM: Artificial Sequence
<220> FEATURE:
<223> OTHER INFORMATION: tracRNA

<400> SEQUENCE: 5
ggaaccauuc aaacagcau agcaaguuaa aauaaggcua guccguuauc aacuugaaaa        60
aguggcaccg agucggugc                                                   79

<210> SEQ ID NO 6
<211> LENGTH: 60
<212> TYPE: RNA
<213> ORGANISM: Artificial Sequence
<220> FEATURE:
<223> OTHER INFORMATION: tracRNA

<400> SEQUENCE: 6
uagcaaguua aaauaaggcu aguccguuau caacuugaaa aaguggcacc gagucggugc       60

<210> SEQ ID NO 7
<211> LENGTH: 64
<212> TYPE: RNA
<213> ORGANISM: Artificial Sequence
<220> FEATURE:
<223> OTHER INFORMATION: tracRNA

<400> SEQUENCE: 7
agcauagcaa guuaaaauaa ggcuaguccg uuaucaacuu gaaaaagugg caccgagucg       60
gugc                                                                   64

<210> SEQ ID NO 8
<211> LENGTH: 70
<212> TYPE: RNA
```

```
<213> ORGANISM: Artificial Sequence
<220> FEATURE:
<223> OTHER INFORMATION: tracRNA

<400> SEQUENCE: 8
caaaacagca uagcaaguua aaauaaggcu aguccguuau caacuugaaa aaguggcacc    60
gagucggugc                                                          70

<210> SEQ ID NO 9
<211> LENGTH: 45
<212> TYPE: RNA
<213> ORGANISM: Artificial Sequence
<220> FEATURE:
<223> OTHER INFORMATION: tracRNA

<400> SEQUENCE: 9
uagcaaguua aaauaaggcu aguccguuau caacuugaaa aagug                    45

<210> SEQ ID NO 10
<211> LENGTH: 32
<212> TYPE: RNA
<213> ORGANISM: Artificial Sequence
<220> FEATURE:
<223> OTHER INFORMATION: tracRNA

<400> SEQUENCE: 10
uagcaaguua aaauaaggcu aguccguuau ca                                  32

<210> SEQ ID NO 11
<211> LENGTH: 26
<212> TYPE: RNA
<213> ORGANISM: Artificial Sequence
<220> FEATURE:
<223> OTHER INFORMATION: tracRNA

<400> SEQUENCE: 11
uagcaaguua aaauaaggcu aguccg                                         26

<210> SEQ ID NO 12
<211> LENGTH: 66
<212> TYPE: DNA
<213> ORGANISM: Artificial Sequence
<220> FEATURE:
<223> OTHER INFORMATION: Ku binding hairpin

<400> SEQUENCE: 12
ttcttgtcgt acttatagat cgctacgtta tttcaattt gaaaatctga gtcctgggag     60
tgcgga                                                               66

<210> SEQ ID NO 13
<211> LENGTH: 609
<212> TYPE: PRT
<213> ORGANISM: Artificial Sequence
<220> FEATURE:
<223> OTHER INFORMATION: Telomerase Ku

<400> SEQUENCE: 13

Met Ser Gly Trp Glu Ser Tyr Tyr Lys Thr Glu Gly Asp Glu Glu Ala
1               5                   10                  15

Glu Glu Glu Gln Glu Glu Asn Leu Glu Ala Ser Gly Asp Tyr Lys Tyr
            20                  25                  30

Ser Gly Arg Asp Ser Leu Ile Phe Leu Val Asp Ala Ser Lys Ala Met
        35                  40                  45
```

```
Phe Glu Ser Gln Ser Glu Asp Glu Leu Thr Pro Phe Asp Met Ser Ile
 50                  55                  60

Gln Cys Ile Gln Ser Val Tyr Ile Ser Lys Ile Ile Ser Ser Asp Arg
 65                  70                  75                  80

Asp Leu Leu Ala Val Val Phe Tyr Gly Thr Glu Lys Asp Lys Asn Ser
                 85                  90                  95

Val Asn Phe Lys Asn Ile Tyr Val Leu Gln Glu Leu Asp Asn Pro Gly
            100                 105                 110

Ala Lys Arg Ile Leu Glu Leu Asp Gln Phe Lys Gly Gln Gln Gly Gln
        115                 120                 125

Lys Arg Phe Gln Asp Met Met Gly His Gly Ser Asp Tyr Ser Leu Ser
130                 135                 140

Glu Val Leu Trp Val Cys Ala Asn Leu Phe Ser Asp Val Gln Phe Lys
145                 150                 155                 160

Met Ser His Lys Arg Ile Met Leu Phe Thr Asn Glu Asp Asn Pro His
                165                 170                 175

Gly Asn Asp Ser Ala Lys Ala Ser Arg Ala Arg Thr Lys Ala Gly Asp
            180                 185                 190

Leu Arg Asp Thr Gly Ile Phe Leu Asp Leu Met His Leu Lys Lys Pro
        195                 200                 205

Gly Gly Phe Asp Ile Ser Leu Phe Tyr Arg Asp Ile Ser Ile Ala
210                 215                 220

Glu Asp Glu Asp Leu Arg Val His Phe Glu Glu Ser Ser Lys Leu Glu
225                 230                 235                 240

Asp Leu Leu Arg Lys Val Arg Ala Lys Glu Thr Arg Lys Arg Ala Leu
                245                 250                 255

Ser Arg Leu Lys Leu Lys Leu Asn Lys Asp Ile Val Ile Ser Val Gly
            260                 265                 270

Ile Tyr Asn Leu Val Gln Lys Ala Leu Lys Pro Pro Pro Ile Lys Leu
        275                 280                 285

Tyr Arg Glu Thr Asn Glu Pro Val Lys Thr Lys Thr Arg Thr Phe Asn
290                 295                 300

Thr Ser Thr Gly Gly Leu Leu Leu Pro Ser Asp Thr Lys Arg Ser Gln
305                 310                 315                 320

Ile Tyr Gly Ser Arg Gln Ile Ile Leu Glu Lys Glu Glu Thr Glu Glu
                325                 330                 335

Leu Lys Arg Phe Asp Asp Pro Gly Leu Met Leu Met Gly Phe Lys Pro
            340                 345                 350

Leu Val Leu Leu Lys Lys His His Tyr Leu Arg Pro Ser Leu Phe Val
        355                 360                 365

Tyr Pro Glu Glu Ser Leu Val Ile Gly Ser Ser Thr Leu Phe Ser Ala
370                 375                 380

Leu Leu Ile Lys Cys Leu Glu Lys Glu Val Ala Ala Leu Cys Arg Tyr
385                 390                 395                 400

Thr Pro Arg Arg Asn Ile Pro Pro Tyr Phe Val Ala Leu Val Pro Gln
                405                 410                 415

Glu Glu Glu Leu Asp Asp Gln Lys Ile Gln Val Thr Pro Pro Gly Phe
            420                 425                 430

Gln Leu Val Phe Leu Pro Phe Ala Asp Asp Lys Arg Lys Met Pro Phe
        435                 440                 445

Thr Glu Lys Ile Met Ala Thr Pro Glu Gln Val Gly Lys Met Lys Ala
450                 455                 460

Ile Val Glu Lys Leu Arg Phe Thr Tyr Arg Ser Asp Ser Phe Glu Asn
```

```
                465                 470                 475                 480
Pro Val Leu Gln Gln His Phe Arg Asn Leu Glu Ala Leu Ala Leu Asp
                        485                 490                 495
Leu Met Glu Pro Glu Gln Ala Val Asp Leu Thr Leu Pro Lys Val Glu
                400                 505                 510
Ala Met Asn Lys Arg Leu Gly Ser Leu Val Asp Glu Phe Lys Glu Leu
                515                 520                 525
Val Tyr Pro Pro Asp Tyr Asn Pro Glu Gly Lys Val Thr Lys Arg Lys
                530                 535                 540
His Asp Asn Glu Gly Ser Gly Ser Lys Arg Pro Lys Val Glu Tyr Ser
545                 550                 555                 560
Glu Glu Glu Leu Lys Thr His Ile Ser Lys Gly Thr Leu Gly Lys Phe
                565                 570                 575
Thr Val Pro Met Leu Lys Glu Ala Cys Arg Ala Tyr Gly Leu Lys Ser
                580                 585                 590
Gly Leu Lys Lys Gln Glu Leu Leu Glu Ala Leu Thr Lys His Phe Gln
                595                 600                 605
Asp

<210> SEQ ID NO 14
<211> LENGTH: 485
<212> TYPE: PRT
<213> ORGANISM: Artificial Sequence
<220> FEATURE:
<223> OTHER INFORMATION: Telomerase Ku

<400> SEQUENCE: 14

Met Val Arg Ser Gly Asn Lys Ala Ala Val Val Leu Cys Met Asp Val
1               5                   10                  15
Gly Phe Thr Met Ser Asn Ser Ile Pro Gly Ile Glu Ser Pro Phe Glu
                20                  25                  30
Gln Ala Lys Lys Val Ile Thr Met Phe Val Gln Arg Gln Val Phe Ala
                35                  40                  45
Glu Asn Lys Asp Glu Ile Ala Leu Val Leu Phe Gly Thr Asp Gly Thr
            50                  55                  60
Asp Asn Pro Leu Ser Gly Gly Asp Gln Tyr Gln Asn Ile Thr Val His
65              70                  75                  80
Arg His Leu Met Leu Pro Asp Phe Asp Leu Leu Glu Asp Ile Glu Ser
                85                  90                  95
Lys Ile Gln Pro Gly Ser Gln Gln Ala Asp Phe Leu Asp Ala Leu Ile
                100                 105                 110
Val Ser Met Asp Val Ile Gln His Glu Thr Ile Gly Lys Lys Phe Glu
                115                 120                 125
Lys Arg His Ile Glu Ile Phe Thr Asp Leu Ser Ser Arg Phe Ser Lys
                130                 135                 140
Ser Gln Leu Asp Ile Ile Ile His Ser Leu Lys Lys Cys Asp Ile Ser
145                 150                 155                 160
Glu Arg His Ser Ile His Trp Pro Cys Arg Leu Thr Ile Gly Ser Asn
                165                 170                 175
Leu Ser Ile Arg Ile Ala Ala Tyr Lys Ser Ile Leu Gln Glu Arg Val
                180                 185                 190
Lys Lys Thr Trp Thr Val Val Asp Ala Lys Thr Leu Lys Lys Glu Asp
                195                 200                 205
Ile Gln Lys Glu Thr Val Tyr Cys Leu Asn Asp Asp Asp Glu Thr Glu
                210                 215                 220
```

-continued

```
Val Leu Lys Glu Asp Ile Ile Gln Gly Phe Arg Tyr Gly Ser Asp Ile
225                 230                 235                 240

Val Pro Phe Ser Lys Val Asp Glu Glu Gln Met Lys Tyr Lys Ser Glu
            245                 250                 255

Gly Lys Cys Phe Ser Val Leu Gly Phe Cys Lys Ser Ser Gln Val Gln
        260                 265                 270

Arg Arg Phe Phe Met Gly Asn Gln Val Leu Lys Val Phe Ala Ala Arg
    275                 280                 285

Asp Asp Glu Ala Ala Val Ala Leu Ser Ser Leu Ile His Ala Leu
290                 295                 300

Asp Asp Leu Asp Met Val Ala Ile Val Arg Tyr Ala Tyr Asp Lys Arg
305                 310                 315                 320

Ala Asn Pro Gln Val Gly Val Ala Phe Pro His Ile Lys His Asn Tyr
            325                 330                 335

Glu Cys Leu Val Tyr Val Gln Leu Pro Phe Met Glu Asp Leu Arg Gln
        340                 345                 350

Tyr Met Phe Ser Ser Leu Lys Asn Ser Lys Lys Tyr Ala Pro Thr Glu
    355                 360                 365

Ala Gln Leu Asn Ala Val Asp Ala Leu Ile Asp Ser Met Ser Leu Ala
370                 375                 380

Lys Lys Asp Glu Lys Thr Asp Thr Leu Glu Asp Leu Phe Pro Thr Thr
385                 390                 395                 400

Lys Ile Pro Asn Pro Arg Phe Gln Arg Leu Phe Gln Cys Leu Leu His
            405                 410                 415

Arg Ala Leu His Pro Arg Glu Pro Leu Pro Pro Ile Gln Gln His Ile
        420                 425                 430

Trp Asn Met Leu Asn Pro Pro Ala Glu Val Thr Thr Lys Ser Gln Ile
    435                 440                 445

Pro Leu Ser Lys Ile Lys Thr Leu Phe Pro Leu Ile Glu Ala Lys Lys
450                 455                 460

Lys Asp Gln Val Thr Ala Gln Glu Ile Phe Gln Asp Asn His Glu Asp
465                 470                 475                 480

Gly Pro Thr Ala Lys
            485
```

<210> SEQ ID NO 15
<211> LENGTH: 10
<212> TYPE: DNA
<213> ORGANISM: Artificial Sequence
<220> FEATURE:
<223> OTHER INFORMATION: Sm consensus site

<400> SEQUENCE: 15 aattttttgga                                                         10

<210> SEQ ID NO 16
<211> LENGTH: 83
<212> TYPE: PRT
<213> ORGANISM: Artificial Sequence
<220> FEATURE:
<223> OTHER INFORMATION: Monomeric Sm - like protein (archaea)

<400> SEQUENCE: 16

```
Gly Ser Val Ile Asp Val Ser Ser Gln Arg Val Asn Val Gln Arg Pro
1               5                   10                  15

Leu Asp Ala Leu Gly Asn Ser Leu Asn Ser Pro Val Ile Ile Lys Leu
            20                  25                  30
```

```
Lys Gly Asp Arg Glu Phe Arg Gly Val Leu Lys Ser Phe Asp Leu His
         35                  40                  45

Met Asn Leu Val Leu Asn Asp Ala Glu Glu Leu Glu Asp Gly Glu Val
 50                  55                  60

Thr Arg Arg Leu Gly Thr Val Leu Ile Arg Gly Asp Asn Ile Val Tyr
 65                  70                  75                  80

Ile Ser Pro

<210> SEQ ID NO 17
<211> LENGTH: 25
<212> TYPE: DNA
<213> ORGANISM: Artificial Sequence
<220> FEATURE:
<223> OTHER INFORMATION: MS2 phage operator stem loop

<400> SEQUENCE: 17
gcgcacatga ggatcaccca tgtgc                                              25

<210> SEQ ID NO 18
<211> LENGTH: 117
<212> TYPE: PRT
<213> ORGANISM: Artificial Sequence
<220> FEATURE:
<223> OTHER INFORMATION: MS2 coat protein

<400> SEQUENCE: 18

Met Ala Ser Asn Phe Thr Gln Phe Val Leu Val Asp Asn Gly Gly Thr
 1               5                  10                  15

Gly Asp Val Thr Val Ala Pro Ser Asn Phe Ala Asn Gly Ile Ala Glu
             20                  25                  30

Trp Ile Ser Ser Asn Ser Arg Ser Gln Ala Tyr Lys Val Thr Cys Ser
         35                  40                  45

Val Arg Gln Ser Ser Ala Gln Asn Arg Lys Tyr Thr Ile Lys Val Glu
 50                  55                  60

Val Pro Lys Gly Ala Trp Arg Ser Tyr Leu Asn Met Glu Leu Thr Ile
 65                  70                  75                  80

Pro Ile Phe Ala Thr Asn Ser Asp Cys Glu Leu Ile Val Lys Ala Met
             85                  90                  95

Gln Gly Leu Leu Lys Asp Gly Asn Pro Ile Pro Ser Ala Ile Ala Ala
            100                 105                 110

Asn Ser Gly Ile Tyr
        115

<210> SEQ ID NO 19
<211> LENGTH: 26
<212> TYPE: DNA
<213> ORGANISM: Artificial Sequence
<220> FEATURE:
<223> OTHER INFORMATION: PP7 phage operator stem loop

<400> SEQUENCE: 19
ataaggagtt tatatggaaa ccctta                                             26

<210> SEQ ID NO 20
<211> LENGTH: 128
<212> TYPE: PRT
<213> ORGANISM: Artificial Sequence
<220> FEATURE:
<223> OTHER INFORMATION: PP7 coat protein (PCP)

<400> SEQUENCE: 20
```

Met Ser Lys Thr Ile Val Leu Ser Val Gly Glu Ala Thr Arg Thr Leu
1               5                   10                  15

Thr Glu Ile Gln Ser Thr Ala Asp Arg Gln Ile Phe Glu Glu Lys Val
            20                  25                  30

Gly Pro Leu Val Gly Arg Leu Arg Leu Thr Ala Ser Leu Arg Gln Asn
        35                  40                  45

Gly Ala Lys Thr Ala Tyr Arg Val Asn Leu Lys Leu Asp Gln Ala Asp
    50                  55                  60

Val Val Asp Cys Ser Thr Ser Val Cys Gly Glu Leu Pro Lys Val Arg
65                  70                  75                  80

Tyr Thr Gln Val Trp Ser His Val Thr Ile Val Ala Asn Ser Thr
                85                  90                  95

Glu Ala Ser Arg Lys Ser Leu Tyr Asp Leu Thr Lys Ser Leu Val Ala
            100                 105                 110

Thr Ser Gln Val Glu Asp Leu Val Val Asn Leu Val Pro Leu Gly Arg
        115                 120                 125

<210> SEQ ID NO 21
<211> LENGTH: 19
<212> TYPE: DNA
<213> ORGANISM: Artificial Sequence
<220> FEATURE:
<223> OTHER INFORMATION: SfMu Com stem loop

<400> SEQUENCE: 21
ctgaatgcct gcgagcatc                                              19

<210> SEQ ID NO 22
<211> LENGTH: 62
<212> TYPE: PRT
<213> ORGANISM: Artificial Sequence
<220> FEATURE:
<223> OTHER INFORMATION: SfMu Com binding protein

<400> SEQUENCE: 22

Met Lys Ser Ile Arg Cys Lys Asn Cys Asn Lys Leu Leu Phe Lys Ala
1               5                   10                  15

Asp Ser Phe Asp His Ile Glu Ile Arg Cys Pro Arg Cys Lys Arg His
            20                  25                  30

Ile Ile Met Leu Asn Ala Cys Glu His Pro Thr Glu Lys His Cys Gly
        35                  40                  45

Lys Arg Glu Lys Ile Thr His Ser Asp Glu Thr Val Arg Tyr
    50                  55                  60

<210> SEQ ID NO 23
<211> LENGTH: 110
<212> TYPE: DNA
<213> ORGANISM: Artificial Sequence
<220> FEATURE:
<223> OTHER INFORMATION: Rpo B RRDR Cluster I

<400> SEQUENCE: 23
gcagcagtga aagagttctt cggttccagc cagctgtctc agtttatgga ccagaacaac    60
ccgctgtctg agattacgca caaacgtcgt atctccgcac tcggcccagg              110

<210> SEQ ID NO 24
<211> LENGTH: 110
<212> TYPE: DNA
<213> ORGANISM: Artificial Sequence
<220> FEATURE:

<223> OTHER INFORMATION: Rpo B RRDR Cluster I

<400> SEQUENCE: 24
cctgggccga gtgcggagat acgacgtttg tgcgtaatct cagacagcgg gttgttctgg    60
tccataaact gagacagctg gctggaaccg aagaactctt tcactgctgc              110

<210> SEQ ID NO 25
<211> LENGTH: 36
<212> TYPE: PRT
<213> ORGANISM: Artificial Sequence
<220> FEATURE:
<223> OTHER INFORMATION: Rpo B RRDR Cluster I PROTEIN

<400> SEQUENCE: 25

Ala Ala Val Lys Glu Phe Phe Gly Ser Ser Gln Leu Ser Gln Phe Met
1               5                   10                  15

Asp Gln Asn Asn Pro Leu Ser Glu Ile Thr His Lys Arg Arg Ile Ser
            20                  25                  30

Ala Leu Gly Pro
        35

<210> SEQ ID NO 26
<211> LENGTH: 30
<212> TYPE: DNA
<213> ORGANISM: Artificial Sequence
<220> FEATURE:
<223> OTHER INFORMATION: Treated Rpo B RRDR Cluster I Ts4

<400> SEQUENCE: 26
acaaacgtcg tatcttcgca ctcggcccag                                    30

<210> SEQ ID NO 27
<211> LENGTH: 30
<212> TYPE: DNA
<213> ORGANISM: Artificial Sequence
<220> FEATURE:
<223> OTHER INFORMATION: Un-treated Rpo B RRDR Cluster I Ts4

<400> SEQUENCE: 27
acaaacgtcg tatctccgca ctcggcccag                                    30

<210> SEQ ID NO 28
<211> LENGTH: 10
<212> TYPE: PRT
<213> ORGANISM: Artificial Sequence
<220> FEATURE:
<223> OTHER INFORMATION: Treated Rpo B RRDR Cluster I Ts4

<400> SEQUENCE: 28

His Lys Arg Arg Ile Phe Ala Leu Gly Pro
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Un-treated Rpo B RRDR Cluster I Ts4

<400> SEQUENCE: 29

His Lys Arg Arg Ile Ser Ala Leu Gly Pro
1               5                   10

<210> SEQ ID NO 30

```
<211> LENGTH: 12
<212> TYPE: PRT
<213> ORGANISM: Artificial Sequence
<220> FEATURE:
<223> OTHER INFORMATION: Un-treated Rpo B RRDR Cluster I Ts3

<400> SEQUENCE: 30

Thr His Lys Arg Arg Ile Ser Ala Leu Gly Pro Gly
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Treated Rpo B RRDR Cluster I Ts4

<400> SEQUENCE: 31

Thr His Lys Arg Arg Ile Phe Ala Leu Gly Pro Gly
1               5                   10

<210> SEQ ID NO 32
<211> LENGTH: 36
<212> TYPE: DNA
<213> ORGANISM: Artificial Sequence
<220> FEATURE:
<223> OTHER INFORMATION: Un-treated Rpo B RRDR Cluster I Ts4

<400> SEQUENCE: 32
acgcacaaac gtcgtatctc cgcactcggc ccaggc                          36

<210> SEQ ID NO 33
<211> LENGTH: 9
<212> TYPE: PRT
<213> ORGANISM: Artificial Sequence
<220> FEATURE:
<223> OTHER INFORMATION: Un-treated scramble

<400> SEQUENCE: 33

Gly Ser Ser Gln Leu Ser Gln Phe Met
1               5

<210> SEQ ID NO 34
<211> LENGTH: 9
<212> TYPE: PRT
<213> ORGANISM: Artificial Sequence
<220> FEATURE:
<223> OTHER INFORMATION: Treated scramble

<400> SEQUENCE: 34

Gly Ser Ser Gln Leu Ser Arg Phe Met
1               5

<210> SEQ ID NO 35
<211> LENGTH: 27
<212> TYPE: DNA
<213> ORGANISM: Artificial Sequence
<220> FEATURE:
<223> OTHER INFORMATION: Un-treated scramble

<400> SEQUENCE: 35
ggttccagcc agctgtctca gtttatg                                    27

<210> SEQ ID NO 36
<211> LENGTH: 5
<212> TYPE: PRT
<213> ORGANISM: Artificial Sequence
```

-continued

```
<220> FEATURE:
<223> OTHER INFORMATION: Un-treated scramble

<400> SEQUENCE: 36

Arg Ile Ser Ala Leu
1               5

<210> SEQ ID NO 37
<211> LENGTH: 5
<212> TYPE: PRT
<213> ORGANISM: Artificial Sequence
<220> FEATURE:
<223> OTHER INFORMATION: Treated scramble

<400> SEQUENCE: 37

Arg Ile Phe Ala Leu
1               5

<210> SEQ ID NO 38
<211> LENGTH: 15
<212> TYPE: DNA
<213> ORGANISM: Artificial Sequence
<220> FEATURE:
<223> OTHER INFORMATION: Un-treated scramble

<400> SEQUENCE: 38
cgtatctccg cactc                                                    15

<210> SEQ ID NO 39
<211> LENGTH: 4
<212> TYPE: PRT
<213> ORGANISM: Artificial Sequence
<220> FEATURE:
<223> OTHER INFORMATION: Un-treated scramble

<400> SEQUENCE: 39

Gly Leu Ile Asn
1

<210> SEQ ID NO 40
<211> LENGTH: 4
<212> TYPE: PRT
<213> ORGANISM: Artificial Sequence
<220> FEATURE:
<223> OTHER INFORMATION: Treated scramble

<400> SEQUENCE: 40

Gly Leu Phe Asn
1

<210> SEQ ID NO 41
<211> LENGTH: 15
<212> TYPE: DNA
<213> ORGANISM: Artificial Sequence
<220> FEATURE:
<223> OTHER INFORMATION: Un-treated scramble

<400> SEQUENCE: 41
ggtctgatca actct                                                    15

<210> SEQ ID NO 42
<211> LENGTH: 51
<212> TYPE: DNA
<213> ORGANISM: Artificial Sequence
<220> FEATURE:
<223> OTHER INFORMATION: nfGFP sense
```

<400> SEQUENCE: 42 cctggccca ccctcgtgac caccctgacc tgcggcgtgc agtgcttcag c        51

<210> SEQ ID NO 43
<211> LENGTH: 51
<212> TYPE: DNA
<213> ORGANISM: Artificial Sequence
<220> FEATURE:
<223> OTHER INFORMATION: nfGFP anti-sense

<400> SEQUENCE: 43
gctgaagcac tgcacgccgc aggtcagggt ggtcacgagg gtgggccagg g        51

<210> SEQ ID NO 44
<211> LENGTH: 17
<212> TYPE: PRT
<213> ORGANISM: Artificial Sequence
<220> FEATURE:
<223> OTHER INFORMATION: nfGFP protein

<400> SEQUENCE: 44

Pro Trp Pro Thr Leu Val Thr Thr Leu Thr Cys Gly Val Gln Cys Phe
1               5                   10                  15

Ser

<210> SEQ ID NO 45
<211> LENGTH: 51
<212> TYPE: DNA
<213> ORGANISM: Artificial Sequence
<220> FEATURE:
<223> OTHER INFORMATION: HPGRT sense

<400> SEQUENCE: 45
ctgaaggggg gctataaatt ctttgctgac ctgctggatt acattaaagc a        51

<210> SEQ ID NO 46
<211> LENGTH: 51
<212> TYPE: DNA
<213> ORGANISM: Artificial Sequence
<220> FEATURE:
<223> OTHER INFORMATION: HPGRT anti-sense

<400> SEQUENCE: 46
tgctttaatg taatccagca ggtcagcaaa gaatttatag ccccccttca g        51

<210> SEQ ID NO 47
<211> LENGTH: 17
<212> TYPE: PRT
<213> ORGANISM: Artificial Sequence
<220> FEATURE:
<223> OTHER INFORMATION: HPGRT protein

<400> SEQUENCE: 47

Leu Lys Gly Gly Tyr Lys Phe Phe Ala Asp Leu Leu Asp Tyr Ile Lys
1               5                   10                  15

Ala

<210> SEQ ID NO 48
<211> LENGTH: 594
<212> TYPE: DNA
<213> ORGANISM: Homo sapiens

<400> SEQUENCE: 48
atggacagcc tcttgatgaa ccggaggaag tttctttacc aattcaaaaa tgtccgctgg        60

```
gctaagggtc ggcgtgagac ctacctgtgc tacgtagtga agaggcgtga cagtgctaca    120
tccttttcac tggactttgg ttatcttcgc aataagaacg gctgccacgt ggaattgctc    180
ttcctccgct acatctcgga ctgggaccta gaccctggcc gctgctaccg cgtcacctgg    240
ttcacctcct ggagcccctg ctacgactgt gcccgacatg tggccgactt ctgcgaggg     300 aaccccaacc tcagtctgag gatcttcacc gcgcgcctct acttctgtga ggaccgcaag    360
gctgagcccg aggggctgcg gcggctgcac cgcgccgggg tgcaaatagc catcatgacc    420
ttcaaagatt attttttactg ctggaatact tttgtagaaa accatgaaag aactttcaaa    480
gcctgggaag gctgcatga aaattcagtt cgtctctcca gacagcttcg gcgcatcctt    540
ttgcccctgt atgaggttga tgacttacga gacgcatttc gtactttggg actt          594
```

<210> SEQ ID NO 49
<211> LENGTH: 198
<212> TYPE: PRT
<213> ORGANISM: Homo sapiens
<400> SEQUENCE: 49

```
Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195
```

<210> SEQ ID NO 50
<211> LENGTH: 594
<212> TYPE: DNA
<213> ORGANISM: Artificial Sequence
<220> FEATURE:
<223> OTHER INFORMATION: encoding S38A mutant
<400> SEQUENCE: 50

```
atggacagcc tcttgatgaa ccggaggaag tttctttacc aattcaaaaa tgtccgctgg    60
gctaagggtc ggcgtgagac ctacctgtgc tacgtagtga agaggcgtga cgccgctaca    120
```

```
tccttttcac tggactttgg ttatcttcgc aataagaacg gctgccacgt ggaattgctc    180
ttcctccgct acatctcgga ctgggaccta gaccctggcc gctgctaccg cgtcacctgg    240
ttcacctcct ggagcccctg ctacgactgt gcccgacatg tggccgactt tctgcgaggg    300
aaccccaacc tcagtctgag gatcttcacc gcgcgcctct acttctgtga ggaccgcaag    360
gctgagcccg aggggctgcg gcggctgcac cgcgccgggg tgcaaatagc catcatgacc    420
ttcaaagatt attttactg ctggaatact tttgtagaaa accatgaaag aactttcaaa    480
gcctgggaag ggctgcatga aaattcagtt cgtctctcca gacagcttcg gcgcatcctt    540
ttgcccctgt atgaggttga tgacttacga gacgcatttc gtactttggg actt          594
```

<210> SEQ ID NO 51
<211> LENGTH: 198
<212> TYPE: PRT
<213> ORGANISM: Artificial Sequence
<220> FEATURE:
<223> OTHER INFORMATION: S38A mutant

<400> SEQUENCE: 51

```
Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ala Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195
```

<210> SEQ ID NO 52
<211> LENGTH: 1367
<212> TYPE: PRT
<213> ORGANISM: Artificial Sequence
<220> FEATURE:
<223> OTHER INFORMATION: Cas9 D10A Protein

<400> SEQUENCE: 52

```
Asp Lys Lys Tyr Ser Ile Gly Leu Ala Ile Gly Thr Asn Ser Val Gly
1               5                   10                  15
```

-continued

```
Trp Ala Val Ile Thr Asp Glu Tyr Lys Val Pro Ser Lys Lys Phe Lys
             20                  25                  30

Val Leu Gly Asn Thr Asp Arg His Ser Ile Lys Lys Asn Leu Ile Gly
             35                  40                  45

Ala Leu Leu Phe Asp Ser Gly Glu Thr Ala Glu Ala Thr Arg Leu Lys
 50                  55                  60

Arg Thr Ala Arg Arg Arg Tyr Thr Arg Arg Lys Asn Arg Ile Cys Tyr
 65                  70                  75                  80

Leu Gln Glu Ile Phe Ser Asn Glu Met Ala Lys Val Asp Asp Ser Phe
                     85                  90                  95

Phe His Arg Leu Glu Glu Ser Phe Leu Val Glu Glu Asp Lys Lys His
                 100                 105                 110

Glu Arg His Pro Ile Phe Gly Asn Ile Val Asp Glu Val Ala Tyr His
             115                 120                 125

Glu Lys Tyr Pro Thr Ile Tyr His Leu Arg Lys Lys Leu Val Asp Ser
         130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                     165                 170                 175

Asn Ser Asp Val Asp Lys Leu Phe Ile Gln Leu Val Gln Thr Tyr Asn
                 180                 185                 190

Gln Leu Phe Glu Glu Asn Pro Ile Asn Ala Ser Gly Val Asp Ala Lys
             195                 200                 205

Ala Ile Leu Ser Ala Arg Leu Ser Lys Ser Arg Arg Leu Glu Asn Leu
210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                 245                 250                 255

Leu Ala Glu Asp Ala Lys Leu Gln Leu Ser Lys Asp Thr Tyr Asp Asp
             260                 265                 270

Asp Leu Asp Asn Leu Leu Ala Gln Ile Gly Asp Gln Tyr Ala Asp Leu
         275                 280                 285

Phe Leu Ala Ala Lys Asn Leu Ser Asp Ala Ile Leu Leu Ser Asp Ile
290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                 325                 330                 335

Leu Val Arg Gln Gln Leu Pro Glu Lys Tyr Lys Glu Ile Phe Phe Asp
             340                 345                 350

Gln Ser Lys Asn Gly Tyr Ala Gly Tyr Ile Asp Gly Gly Ala Ser Gln
         355                 360                 365

Glu Glu Phe Tyr Lys Phe Ile Lys Pro Ile Leu Glu Lys Met Asp Gly
         370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                 405                 410                 415

Glu Leu His Ala Ile Leu Arg Arg Gln Glu Asp Phe Tyr Pro Phe Leu
             420                 425                 430

Lys Asp Asn Arg Glu Lys Ile Glu Lys Ile Leu Thr Phe Arg Ile Pro
```

```
            435                 440                 445
Tyr Tyr Val Gly Pro Leu Ala Arg Gly Asn Ser Arg Phe Ala Trp Met
450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                    485                 490                 495

Phe Asp Lys Asn Leu Pro Asn Glu Lys Val Leu Pro Lys His Ser Leu
                500                 505                 510

Leu Tyr Glu Tyr Phe Thr Val Tyr Asn Glu Leu Thr Lys Val Lys Tyr
            515                 520                 525

Val Thr Glu Gly Met Arg Lys Pro Ala Phe Leu Ser Gly Glu Gln Lys
        530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
                    565                 570                 575

Val Glu Ile Ser Gly Val Glu Asp Arg Phe Asn Ala Ser Leu Gly Thr
                580                 585                 590

Tyr His Asp Leu Leu Lys Ile Ile Lys Asp Lys Asp Phe Leu Asp Asn
            595                 600                 605

Glu Glu Asn Glu Asp Ile Leu Glu Asp Ile Val Leu Thr Leu Thr Leu
        610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
                    645                 650                 655

Gly Trp Gly Arg Leu Ser Arg Lys Leu Ile Asn Gly Ile Arg Asp Lys
                660                 665                 670

Gln Ser Gly Lys Thr Ile Leu Asp Phe Leu Lys Ser Asp Gly Phe Ala
            675                 680                 685

Asn Arg Asn Phe Met Gln Leu Ile His Asp Asp Ser Leu Thr Phe Lys
        690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                    725                 730                 735

Leu Gln Thr Val Lys Val Val Asp Glu Leu Val Lys Val Met Gly Arg
                740                 745                 750

His Lys Pro Glu Asn Ile Val Ile Glu Met Ala Arg Glu Asn Gln Thr
            755                 760                 765

Thr Gln Lys Gly Gln Lys Asn Ser Arg Glu Arg Met Lys Arg Ile Glu
        770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                    805                 810                 815

Asn Gly Arg Asp Met Tyr Val Asp Gln Glu Leu Asp Ile Asn Arg Leu
                820                 825                 830

Ser Asp Tyr Asp Val Asp His Ile Val Pro Gln Ser Phe Leu Lys Asp
            835                 840                 845

Asp Ser Ile Asp Asn Lys Val Leu Thr Arg Ser Asp Lys Asn Arg Gly
        850                 855                 860
```

```
Lys Ser Asp Asn Val Pro Ser Glu Glu Val Val Lys Met Lys Asn
865                 870                 875                 880

Tyr Trp Arg Gln Leu Leu Asn Ala Lys Leu Ile Thr Gln Arg Lys Phe
            885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
            915                 920                 925

His Val Ala Gln Ile Leu Asp Ser Arg Met Asn Thr Lys Tyr Asp Glu
            930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
            965                 970                 975

Ile Asn Asn Tyr His His Ala His Asp Ala Tyr Leu Asn Ala Val Val
            980                 985                 990

Gly Thr Ala Leu Ile Lys Lys Tyr Pro Lys Leu Glu Ser Glu Phe Val
            995                 1000                1005

Tyr Gly Asp Tyr Lys Val Tyr Asp Val Arg Lys Met Ile Ala Lys
    1010                1015                1020

Ser Glu Gln Glu Ile Gly Lys Ala Thr Ala Lys Tyr Phe Phe Tyr
    1025                1030                1035

Ser Asn Ile Met Asn Phe Phe Lys Thr Glu Ile Thr Leu Ala Asn
    1040                1045                1050

Gly Glu Ile Arg Lys Arg Pro Leu Ile Glu Thr Asn Gly Glu Thr
    1055                1060                1065

Gly Glu Ile Val Trp Asp Lys Gly Arg Asp Phe Ala Thr Val Arg
    1070                1075                1080

Lys Val Leu Ser Met Pro Gln Val Asn Ile Val Lys Lys Thr Glu
    1085                1090                1095

Val Gln Thr Gly Gly Phe Ser Lys Glu Ser Ile Leu Pro Lys Arg
    1100                1105                1110

Asn Ser Asp Lys Leu Ile Ala Arg Lys Lys Asp Trp Asp Pro Lys
    1115                1120                1125

Lys Tyr Gly Gly Phe Asp Ser Pro Thr Val Ala Tyr Ser Val Leu
    1130                1135                1140

Val Val Ala Lys Val Glu Lys Gly Lys Ser Lys Lys Leu Lys Ser
    1145                1150                1155

Val Lys Glu Leu Leu Gly Ile Thr Ile Met Glu Arg Ser Ser Phe
    1160                1165                1170

Glu Lys Asn Pro Ile Asp Phe Leu Glu Ala Lys Gly Tyr Lys Glu
    1175                1180                1185

Val Lys Lys Asp Leu Ile Ile Lys Leu Pro Lys Tyr Ser Leu Phe
    1190                1195                1200

Glu Leu Glu Asn Gly Arg Lys Arg Met Leu Ala Ser Ala Gly Glu
    1205                1210                1215

Leu Gln Lys Gly Asn Glu Leu Ala Leu Pro Ser Lys Tyr Val Asn
    1220                1225                1230

Phe Leu Tyr Leu Ala Ser His Tyr Glu Lys Leu Lys Gly Ser Pro
    1235                1240                1245

Glu Asp Asn Glu Gln Lys Gln Leu Phe Val Glu Gln His Lys His
    1250                1255                1260
```

Tyr Leu Asp Glu Ile Ile Glu Gln Ile Ser Glu Phe Ser Lys Arg
    1265                1270                1275

Val Ile Leu Ala Asp Ala Asn Leu Asp Lys Val Leu Ser Ala Tyr
    1280                1285                1290

Asn Lys His Arg Asp Lys Pro Ile Arg Glu Gln Ala Glu Asn Ile
    1295                1300                1305

Ile His Leu Phe Thr Leu Thr Asn Leu Gly Ala Pro Ala Ala Phe
    1310                1315                1320

Lys Tyr Phe Asp Thr Thr Ile Asp Arg Lys Arg Tyr Thr Ser Thr
    1325                1330                1335

Lys Glu Val Leu Asp Ala Thr Leu Ile His Gln Ser Ile Thr Gly
    1340                1345                1350

Leu Tyr Glu Thr Arg Ile Asp Leu Ser Gln Leu Gly Gly Asp
    1355                1360                1365

<210> SEQ ID NO 53
<211> LENGTH: 4101
<212> TYPE: DNA
<213> ORGANISM: Artificial Sequence
<220> FEATURE:
<223> OTHER INFORMATION: DNA encoding Cas9 D10A Protein

<400> SEQUENCE: 53
gataaaaagt attctattgg tttagccatc ggcactaatt ccgttggatg ggctgtcata      60
accgatgaat acaaagtacc ttcaaagaaa tttaaggtgt tggggaacac agaccgtcat     120
tcgattaaaa agaatcttat cggtgccctc ctattcgata gtggcgaaac ggcagaggcg     180
actcgcctga acgaaccgcg tcggagaagg tatacacgtc gcaagaaccg aatatgttac     240
ttacaagaaa ttttagcaa tgagatggcc aaagttgacg attctttctt tcaccgtttg     300
gaagagtcct tccttgtcga agaggacaag aaacatgaac ggcaccccat ctttggaaac     360
atagtagatg aggtggcata tcatgaaaag tacccaacga tttatcacct cagaaaaaag     420
ctagttgact caactgataa agcggacctg aggttaatct acttggctct tgcccatatg     480
ataaagttcc gtgggcactt tctcattgag ggtgatctaa atccggacaa ctcggatgtc     540
gacaaactgt tcatccagtt agtacaaacc tataatcagt tgtttgaaga accctata      600 aatgcaagtg gcgtggatgc gaaggctatt cttagcgccc gcctctctaa atcccgacgg     660
ctagaaaacc tgatcgcaca attcccggga gagaagaaaa tgggttgtt cggtaacctt     720 atagcgctct cactaggcct gacaccaaat tttaagtcga acttcgactt agctgaagat     780
gccaaattgc agcttagtaa ggacacgtac gatgacgatc tcgacaatct actggcacaa     840
attggagatc agtatgcgga cttatttttg gctgccaaaa accttagcga tgcaatcctc     900
ctatctgaca tactgagagt taatactgag attaccaagg cgccgttatc cgcttcaatg     960
atcaaaaggt acgatgaaca tcaccaagac ttgacacttc tcaaggccct agtccgtcag    1020
caactgcctg agaaatataa ggaaatattc tttgatcagt cgaaaaacgg gtacgcaggt    1080
tatattgacg gcggagcgag tcaagaggaa ttctacaagt ttatcaaacc catattagag    1140
aagatggatg gaacggaaga gttgcttgta aaactcaatc gcgaagatct actgcgaaag    1200
cagcggactt tcgacaacgg tagcattcca catcaaatcc acttaggcga attgcatgct    1260
atacttagaa ggcaggagga tttttatccg ttcctcaaag acaatcgtga aaagattgag    1320
aaaatcctaa cctttcgcat acctactat gtgggacccc tggccgagg gaactctcgg    1380 ttcgcatgga tgacaagaaa gtccgaagaa acgattactc catggaattt tgaggaagtt    1440

```
gtcgataaag gtgcgtcagc tcaatcgttc atcgagagga tgaccaactt tgacaagaat    1500
ttaccgaacg aaaaagtatt gcctaagcac agtttacttt acgagtattt cacagtgtac    1560
aatgaactca cgaaagttaa gtatgtcact gagggcatgc gtaaacccgc ctttctaagc    1620
ggagaacaga agaaagcaat agtagatctg ttattcaaga ccaaccgcaa agtgacagtt    1680
aagcaattga agaggacta ctttaagaaa attgaatgct tcgattctgt cgagatctcc    1740
ggggtagaag atcgatttaa tgcgtcactt ggtacgtatc atgacctcct aaagataatt    1800
aaagataagg acttcctgga taacgaagag aatgaagata tcttagaaga tatagtgttg    1860
actcttaccc tctttgaaga tcgggaaatg attgaggaaa gactaaaaac atacgctcac    1920
ctgttcgacg ataaggttat gaaacagtta aagaggcgtc gctatacggg ctggggacga    1980
ttgtcgcgga aacttatcaa cgggataaga gacaagcaaa gtggtaaaac tattctcgat    2040
tttctaaaga gcgacggctt cgccaatagg aactttatgc agctgatcca tgatgactct    2100
ttaaccttca aagaggatat acaaaaggca caggtttccg gacaagggga ctcattgcac    2160
gaacatattg cgaatcttgc tggttcgcca gccatcaaaa agggcatact ccagacagtc    2220
aaagtagtgg atgagctagt taaggtcatg ggacgtcaca aaccggaaaa cattgtaatc    2280
gagatggcac gcgaaaatca aacgactcag aagggggcaaa aaaacagtcg agagcggatg    2340
aagagaatag aagagggtat taaagaactg ggcagccaga tcttaaagga gcatcctgtg    2400 gaaaatacc aattgcagaa cgagaaactt tacctctatt acctacaaaa tggaagggac    2460
atgtatgttg atcaggaact ggacataaac cgtttatctg attacgacgt cgatcacatt    2520
gtaccccaat cctttttgaa ggacgattca atcgacaata aagtgcttac acgctcggat    2580
aagaaccgag ggaaaagtga caatgttcca agcgaggaag tcgtaaagaa aatgaagaac    2640
tattggcggc agctcctaaa tgcgaaactg ataacgcaaa gaaagttcga taacttaact    2700
aaagctgaga ggggtggctt gtctgaactt gacaaggccg gatttattaa acgtcagctc    2760
gtggaaaccc gccaaatcac aaagcatgtt gcacagatac tagattcccg aatgaatacg    2820
aaatacgacg agaacgataa gctgattcgg gaagtcaaag taatcacttt aaagtcaaaa    2880
ttggtgtcgg acttcagaaa ggattttcaa ttctataaag ttagggagat aaataactac    2940
caccatgcgc acgacgctta tcttaatgcc gtcgtaggga ccgcactcat taagaaatac    3000
ccgaagctag aaagtgagtt tgtgtatggt gattacaaag tttatgacgt ccgtaagatg    3060
atcgcgaaaa gcgaacagga gataggcaag gctacagcca atacttctt ttattctaac    3120 attatgaatt tctttaagac ggaaatcact ctggcaaacg gagagatacg caaacgacct    3180
ttaattgaaa ccaatgggga gacaggtgaa atcgtatggg ataagggccg ggacttcgcg    3240
acggtgagaa aagttttgtc catgccccaa gtcaacatag taaagaaaac tgaggtgcag    3300
accggagggt tttcaaagga atcgattctt ccaaaaagga atagtgataa gctcatcgct    3360
cgtaaaaagg actgggaccc gaaaaagtac ggtggcttcg atagccctac agttgcctat    3420
tctgtcctag tagtggcaaa agttgagaag ggaaaatcca agaaactgaa gtcagtcaaa    3480
gaattattgg ggataacgat tatggagcgc tcgtcttttg aaaagaaccc catcgacttc    3540
cttgaggcga aggttacaa ggaagtaaaa aaggatctca taattaaact accaaagtat    3600
agtctgtttg agttagaaaa tggccgaaaa cggatgttgg ctagcgccgg agagcttcaa    3660
aaggggaacg aactcgcact accgtctaaa tacgtgaatt tcctgtattt agcgtcccat    3720
tacgagaagt tgaaaggttc acctgaagat aacgaacaga agcaacttt tgttgagcag    3780 cacaaacatt atctcgacga aatcatagag caaatttcgg aattcagtaa gagagtcatc    3840
```

```
ctagctgatg ccaatctgga caaagtatta agcgcataca acaagcacag ggataaaccc    3900
atacgtgagc aggcggaaaa tattatccat ttgtttactc ttaccaacct cggcgctcca    3960
gccgcattca agtattttga cacaacgata gatcgcaaac gatacacttc taccaaggag    4020
gtgctagacg cgacactgat tcaccaatcc atcacgggat tatatgaaac tcggatagat    4080
ttgtcacagc ttgggggtga c                                              4101

<210> SEQ ID NO 54
<211> LENGTH: 157
<212> TYPE: DNA
<213> ORGANISM: Artificial Sequence
<220> FEATURE:
<223> OTHER INFORMATION: 2xMS2 RNA scaffold expression cassette

<400> SEQUENCE: 54
gttttagagc tagaaatagc aagttaaaat aaggctagtc cgttatcaac ttgaaaaagt      60
ggcaccgagt cggtgcggga gcacatgagg atcacccatg tgccacgagc gacatgagga    120
tcacccatgt cgctcgtgtt ccctttttt ctccgct                             157
```